United States Patent
Bryan et al.

(10) Patent No.: US 11,978,532 B2
(45) Date of Patent: May 7, 2024

(54) CROSS-VARIANT POLYGENIC PREDICTIVE DATA ANALYSIS

(71) Applicant: Optum Services (Ireland) Limited, Dublin (IE)

(72) Inventors: Kenneth Bryan, Dublin (IE); Megan O'Brien, Kildare (IE); David S. Monaghan, Dublin (IE); Chirag Chadha, Dublin (IE)

(73) Assignee: Optum Services (Ireland) Limited, Dublin (IE)

( * ) Notice: Subject to any disclaimer, the term of this patent is extended or adjusted under 35 U.S.C. 154(b) by 600 days.

(21) Appl. No.: 16/863,389

(22) Filed: Apr. 30, 2020

(65) Prior Publication Data
US 2021/0343408 A1    Nov. 4, 2021

(51) Int. Cl.
*G16B 20/00*     (2019.01)
*G06F 18/23213*  (2023.01)
*G16B 20/20*     (2019.01)
*G16B 20/40*     (2019.01)
*G16B 40/00*     (2019.01)
*G16H 20/00*     (2018.01)
(Continued)

(52) U.S. Cl.
CPC ....... *G16B 20/00* (2019.02); *G06F 18/23213* (2023.01); *G16B 20/20* (2019.02); *G16B 20/40* (2019.02); *G16B 40/00* (2019.02); *G16H 20/00* (2018.01); *G16H 50/20* (2018.01); *G16H 50/70* (2018.01)

(58) Field of Classification Search
CPC .......... G16H 10/00–80/00; G06K 1/00; G06K 2215/111; G06N 3/00–99/007
See application file for complete search history.

(56) References Cited

U.S. PATENT DOCUMENTS

| 7,653,491 B2 | 1/2010 | Schadt et al. |
| 9,984,147 B2 | 5/2018 | Long et al. |
| 2002/0045171 A1 | 4/2002 | Comings |

(Continued)

FOREIGN PATENT DOCUMENTS

| CN | 104812947 A | 7/2015 | |
| CN | 107710185 A * | 2/2018 | ............. G06F 19/24 |

(Continued)

OTHER PUBLICATIONS

Monti et al., "Consensus Clustering: A Resampling-Based Method for Class Discovery and Visualization of Gene Expression Microarray Data," Machine Learning, 52, 91-118, 2003. (Year: 2003).*

(Continued)

*Primary Examiner* — Jonathon A. Szumny
(74) *Attorney, Agent, or Firm* — ALSTON & BIRD LLP

(57) ABSTRACT

There is a need for more effective and efficient predictive data analysis solutions for processing genetic sequencing data. This need can be addressed by, for example, techniques for performing predictive data analysis based on genetic sequences that utilize at least one of cross-variant polygenic risk modeling using genetic risk profiles, cross-variant polygenic risk modeling using functional genetic risk profiles, per-condition polygenic clustering operations, cross-condition polygenic predictive inferences, and cross-condition polygenic diagnoses.

18 Claims, 33 Drawing Sheets

(51) Int. Cl.
*G16H 50/20* (2018.01)
*G16H 50/70* (2018.01)

(56) References Cited

U.S. PATENT DOCUMENTS

| | | | |
|---|---|---|---|
| 2003/0040002 | A1 | 2/2003 | Ledley |
| 2003/0162207 | A1 | 8/2003 | Comings et al. |
| 2008/0154514 | A1* | 6/2008 | Magness ............... G16H 10/60 |
| | | | 702/19 |
| 2009/0299645 | A1 | 12/2009 | Colby et al. |
| 2009/0307181 | A1* | 12/2009 | Colby .................... G16B 20/10 |
| | | | 706/54 |
| 2013/0013213 | A1 | 1/2013 | Worthey et al. |
| 2013/0231404 | A1 | 9/2013 | Segal |
| 2015/0066378 | A1 | 3/2015 | Robison et al. |
| 2015/0356243 | A1 | 12/2015 | Andreassen et al. |
| 2016/0068915 | A1 | 3/2016 | Kennedy et al. |
| 2016/0092631 | A1 | 3/2016 | Yandell et al. |
| 2016/0314245 | A1 | 10/2016 | Silver et al. |
| 2016/0371431 | A1* | 12/2016 | Haque .................... G06N 7/01 |
| 2017/0255743 | A1* | 9/2017 | Torkamani ............ G16B 50/00 |
| 2018/0032666 | A1 | 2/2018 | Sun et al. |
| 2018/0060482 | A1* | 3/2018 | Nadauld ................ G06N 20/00 |
| 2018/0107785 | A1 | 4/2018 | Torkamani et al. |
| 2019/0017119 | A1 | 1/2019 | Khera et al. |
| 2019/0019083 | A1* | 1/2019 | Trunck .................... G06N 3/04 |
| 2019/0345566 | A1 | 11/2019 | Khera et al. |
| 2020/0027557 | A1 | 1/2020 | Karow et al. |
| 2020/0097835 | A1 | 3/2020 | Silver et al. |
| 2020/0251193 | A1 | 8/2020 | White et al. |
| 2020/0299771 | A1 | 9/2020 | Snyder et al. |
| 2020/0342955 | A1* | 10/2020 | Guo ...................... G16B 20/00 |

FOREIGN PATENT DOCUMENTS

| | | | |
|---|---|---|---|
| KR | 10-1805597 B1 | 1/2018 | |
| WO | 2010/142713 A1 | 12/2010 | |
| WO | 2011/038155 A2 | 3/2011 | |
| WO | 2015/184249 A2 | 12/2015 | |
| WO | 2017/087206 A1 | 5/2017 | |
| WO | 2019/070634 A1 | 4/2019 | |
| WO | WO-2019139950 A1 * | 7/2019 | ............ G06F 17/18 |
| WO | 2019/169049 A1 | 9/2019 | |
| WO | WO-2019166792 A1 * | 9/2019 | ........... G06K 9/6297 |
| WO | 2019/195638 A1 | 10/2019 | |
| WO | WO-2021094622 A2 * | 5/2021 | ............ G16B 20/00 |

OTHER PUBLICATIONS

Chaudhary et al., "Deep Learning-Based Multi-Omics Integration Robustly Predicts Survival in Liver Cancer," Clin Cancer Res; 24(6) Mar. 15, 2018. doi: 10.1158/1078-0432.CCR-17-0853 (Year: 2018).*

Kruppa et al., "Risk estimation and risk prediction using machine-learning methods," Hum Genet (2012) 131:1639-1654; DOI 10.1007/s00439-012-1194-y. (Year: 2012).*

Hofree, Matan et al. "Network-Based Stratification of Tumor Mutations," Nature Methods, vol. 10, No. 11, Nov. 2013, (11 pages). DOI: 10.1038/NMETH.2651.

Pei, Kexin et al. "Towards Practical Verification of Machine Learning: The Case of Computer Vision Systems," arXiv:1712.01785v3, Dec. 16, 2017, pp. 1-16.

Wu, Jia et al. "Unsupervised Clustering of Quantitative Image Phenotypes Reveals Breast Cancer Subtypes With Distinct Prognoses and Molecular Pathways," Clinical Cancer Research, vol. 23, No. 13, Jul. 1, 2017, pp. 3334-3342. DOI: 10.1158/1078-0432.CCR-16-2415.

Curtis, David. "A Weighted Burden Test Using Logistic Regression for Integrated Analysis of Sequence Variants, Copy Number Variants and Polygenic Risk Score," European Journal of Human Genetics, vol. 27, pp. 114-124 (Year: 2019), (ePublished: Sep. 26, 2018), DOI: 10.1038/s41431-018-0272-6.

Inouye, Michael et al., "Genomic Risk Prediction of Coronary Artery Disease in 480,000 Adults Implications for Primary Prevention," Journal of the American College of Cardiology, vol. 72, No. 16, Oct. 16, 2018, pp. 1883-1893.

NonFinal Office Action for U.S. Appl. No. 16/863,283, dated Apr. 22, 2022, (32 pages), United States Patent and Trademark Office, US.

Pare, Guillaume et al. "A Machine-Learning Heuristic to Improve Gene Score Prediction of Polygenic Traits," Scientific Reports, vol. 7, No. 12665, Oct. 4, 2017, pp. 1-11, DOI: 10.1038/s41598-017-13056-1.

Corrected Notice of Allowability for U.S. Appl. No. 16/863,362, dated Jul. 20, 2022, (6 pages), United States Patent and Trademark Office, Alexandria, Virginia, US.

NonFinal Office Action for U.S. Appl. No. 16/863,427, dated Jul. 5, 2022, (19 pages), United States Patent and Trademark Office, US.

Notice of Allowance and Fee(s) Due for U.S. Appl. No. 16/863,362, dated Jun. 9, 2022, (21 pages), United States Patent and Trademark Office, US.

Notice of Allowance and Fee(s) Due for U.S. Appl. No. 16/863,427, dated Oct. 17, 2022, (9 pages), United States Patent and Trademark Office, US.

Notice of Allowance and Fee(s) Due for U.S. Appl. No. 16/863,283, dated Nov. 14, 2022, (11 pages), United States Patent and Trademark Office, US.

NonFinal Office Action for U.S. Appl. No. 17/930,438, dated May 19, 2023, (7 pages), United States Patent and Trademark Office, US.

Restriction Requirement for U.S. Appl. No. 16/863,403, dated May 10, 2023, 5 pages, United States Patent and Trademark Office, US.

Notice of Allowance and Fees Due for U.S. Appl. No. 16/863,403, dated Dec. 20, 2023, (7 pages), United States Patent and Trademark Office, US.

\* cited by examiner

CROSS-VARIANT POLYGENIC PREDICTIVE DATA ANALYSIS

BACKGROUND

Various embodiments of the present invention address technical challenges related to performing predictive data analysis based on genetic sequences. Various embodiments of the present invention disclose innovative techniques for performing predictive data analysis based on genetic sequences by using cross-variant polygenic risk data objects.

BRIEF SUMMARY

In general, embodiments of the present invention provide methods, apparatuses, systems, computing devices, computing entities, and/or the like for performing predictive data analysis based on genetic sequences. Various embodiments of the present invention disclose techniques for performing predictive data analysis based on genetic sequences, where the noted techniques utilize at least one of cross-variant polygenic risk modeling using genetic risk profiles, cross-variant polygenic risk modeling using functional genetic risk profiles, per-condition polygenic clustering operations, cross-condition polygenic predictive inferences, and cross-condition polygenic diagnoses.

In accordance with one aspect, a method is provided. In one embodiment, the method comprises generating, for each genetic variant of a plurality of genetic variants that is associated with a chromosome of a plurality of chromosomes, a per-variant genetic risk score of a plurality of per-variant genetic risk scores based on: (i) a per-variant risk probability value for the genetic variant in relation to a target medical condition that is selected from a plurality of per-variant risk probability values for a plurality of genetic variants, and (ii) a per-variant allele count for the genetic variant in relation to a target individual that is selected from a plurality of per-variant allele counts for the plurality of genetic variants; generating a genetic risk profile for the plurality of genetic variants, wherein: (i) the genetic risk profile comprises one or more per-chromosome profile segments each associated with a chromosome of the plurality of chromosomes, and (ii) each per-chromosome profile segment of the one or more per-chromosome profile segments that is associated with a respective chromosome of the plurality of chromosomes comprises each per-variant genetic risk score for a genetic variant in a subset of the plurality of genetic variants that is associated with the respective chromosome; and performing one or more prediction-based actions based on the genetic risk profile.

In one embodiment, the method comprises generating, for each genetic variant of a plurality of genetic variants, a per-variant genetic risk score of a plurality of per-variant genetic risk scores based on: (i) a per-variant risk probability value for the genetic variant in relation to a target medical condition that is selected from a plurality of per-variant risk probability values, and (ii) a per-variant allele count for the genetic variant in relation to the target individual that is selected from a plurality of per-variant allele counts; generating a functional genetic risk profile for the plurality of genetic variants, wherein: (i) the functional genetic risk profile comprises a plurality of per-functional-grouping segments each associated with a functional grouping of a plurality of functional groupings, and (ii) each per-functional-grouping profile segment of the plurality of per-functional-grouping profile segments that is associated with a respective functional grouping of the plurality of functional groupings comprises each per-variant genetic risk score for a genetic variant in a subset of the plurality of genetic variants that is associated with the respective functional grouping; and performing one or more prediction-based actions based on the functional genetic risk profile.

In one embodiment, the method comprises identifying a plurality of cross-variant polygenic risk data objects for each individual of a plurality of individuals in relation to a target medical condition, wherein each cross-variant polygenic risk data object of the plurality of cross-variant polygenic risk data objects is associated with a set of modeled genetic variants; for each cross-variant polygenic risk data object of the plurality of cross-variant polygenic risk data objects, generating one or more per-object feature values corresponding to one or more clustering features, wherein the one or more clustering features are determined based on each set of modeled genetic variants for a cross-variant polygenic risk data object of the plurality of cross-variant polygenic risk data objects; generating a polygenic clustering space based on each one or more per-object feature values for a cross-variant polygenic risk data object of the plurality of cross-variant polygenic risk data objects; generating one or more inferred sub-conditions for the target medical condition based on the polygenic clustering space; and performing one or more prediction-based actions based on the one or more inferred sub-conditions.

In one embodiment, the method comprises identifying one or more primary cross-variant polygenic risk data objects for a primary medical condition; identifying one or more secondary cross-variant polygenic risk data objects for a secondary medical condition; generating a cross-condition polygenic similarity measure between the primary medical condition and the secondary medical condition based on comparing the one or more primary cross-variant polygenic risk data objects and the one or more secondary cross-variant polygenic risk data objects; and performing a prediction-based action based on the cross-condition polygenic similarity measure.

In one embodiment, the method comprises identifying one or more undiagnosed cross-variant polygenic risk data objects for an undiagnosed individual with respect to an undiagnosed medical condition; identifying, for each diagnosed individual of one or more diagnosed individuals that is associated with a diagnosed medical condition of one or more diagnosed conditions, one or more diagnosed cross-variant polygenic risk data objects of a plurality of diagnosed cross-variant polygenic risk data objects; for each diagnosed individual of one or more diagnosed individuals, generating a cross-condition polygenic similarity measure based on comparing the one or more diagnosed cross-variant polygenic risk data objects for the diagnosed individual and the one or more undiagnosed cross-variant polygenic risk data objects; generating an inferred diagnosis for the undiagnosed individual based on each cross-condition polygenic similarity measure for a diagnosed individual of one or more diagnosed individuals; and performing one or more prediction-based actions based on the inferred diagnosis.

In accordance with another aspect, a computer program product is provided. The computer program product may comprise at least one computer-readable storage medium having computer-readable program code portions stored therein, the computer-readable program code portions comprising executable portions configured to perform the operations at least one of the methods described above.

In accordance with yet another aspect, an apparatus comprising at least one processor and at least one memory, including computer program code, is provided. In one embodiment, the at least one memory and the computer program code may be configured to, with the processor, cause the apparatus to perform the operations at least one of the methods described above.

BRIEF DESCRIPTION OF THE DRAWINGS

Figure 1:
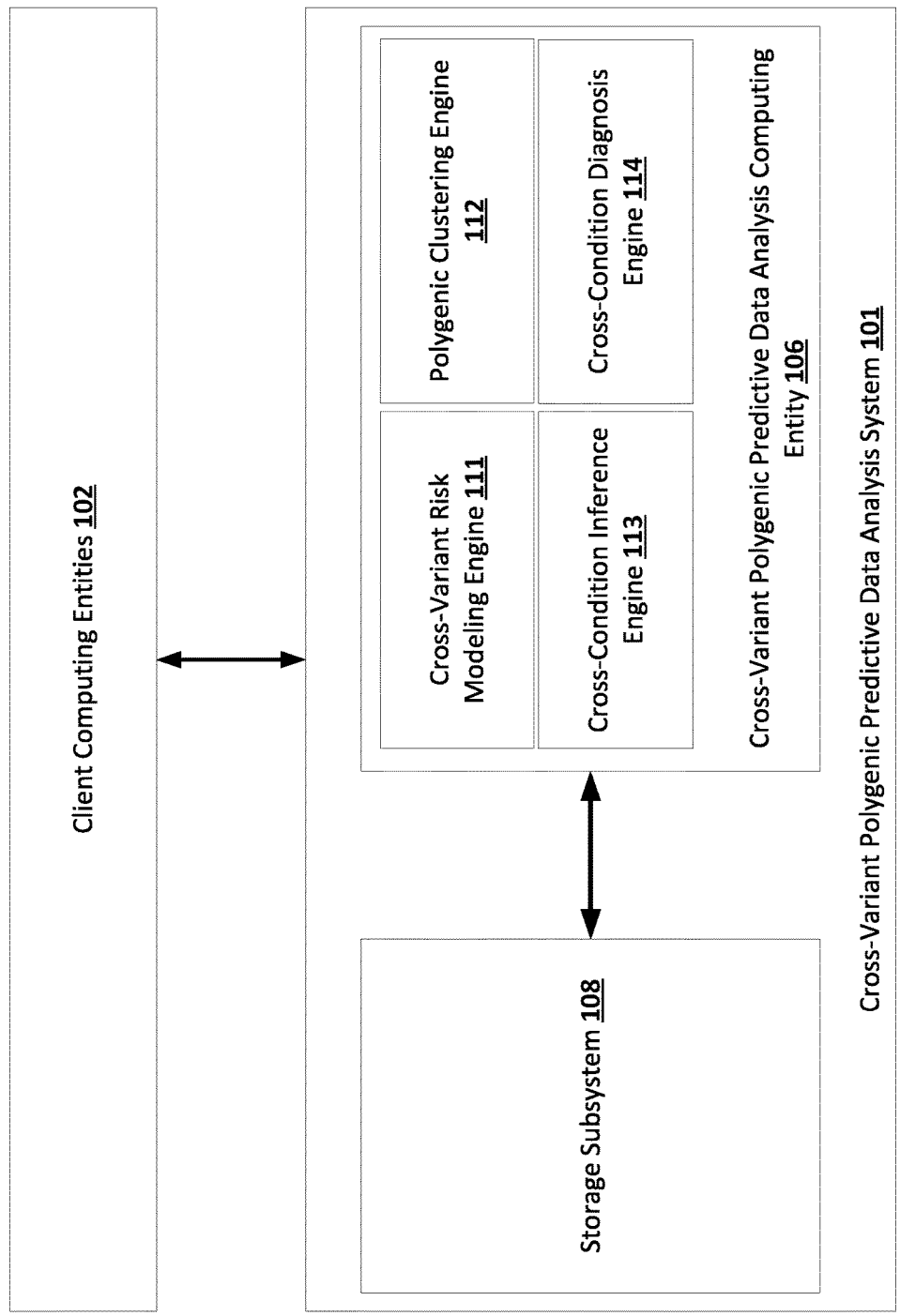

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
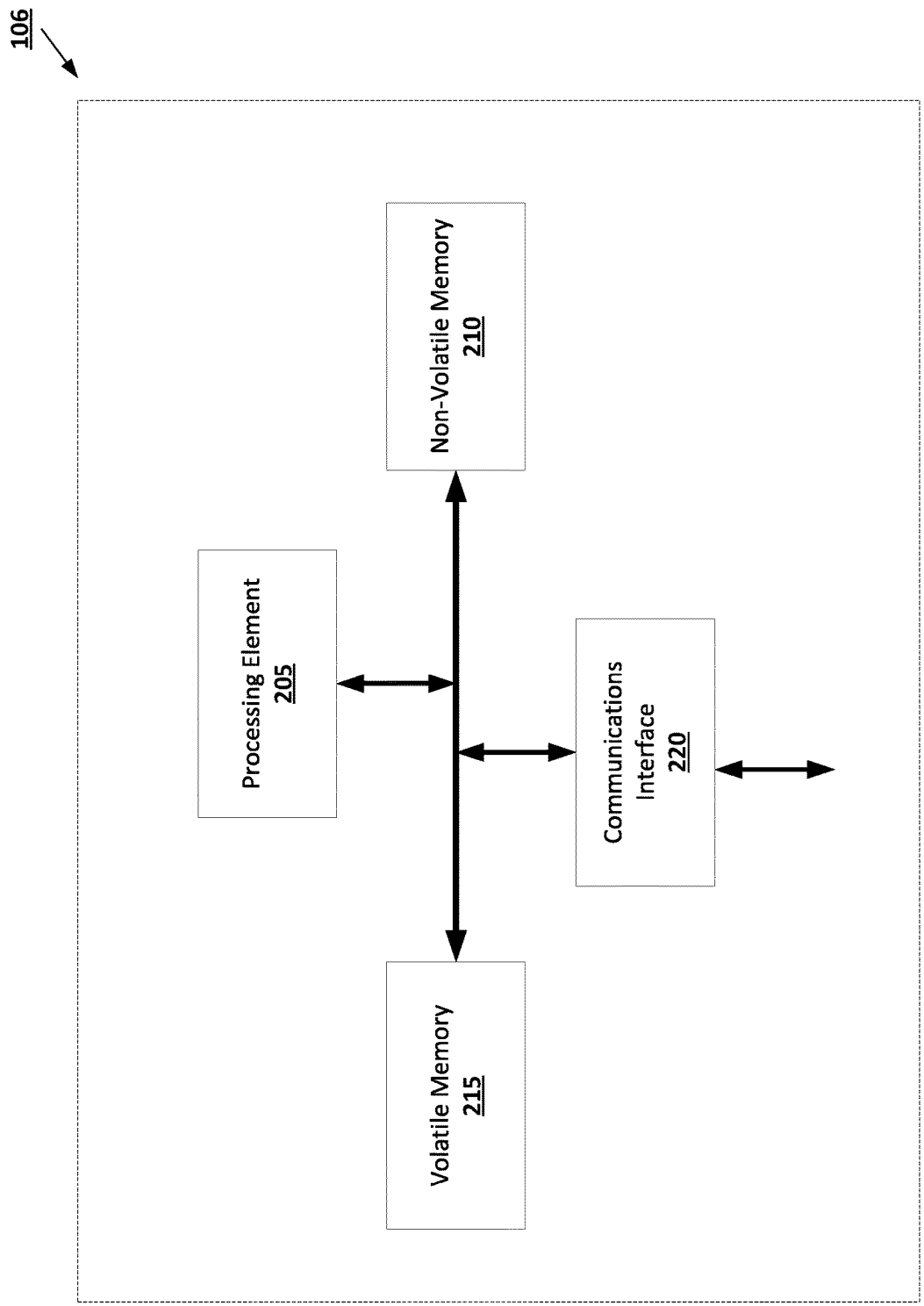

FIG. 2 provides an example cross-variant polygenic predictive data analysis computing entity in accordance with some embodiments discussed herein.

Figure 3:
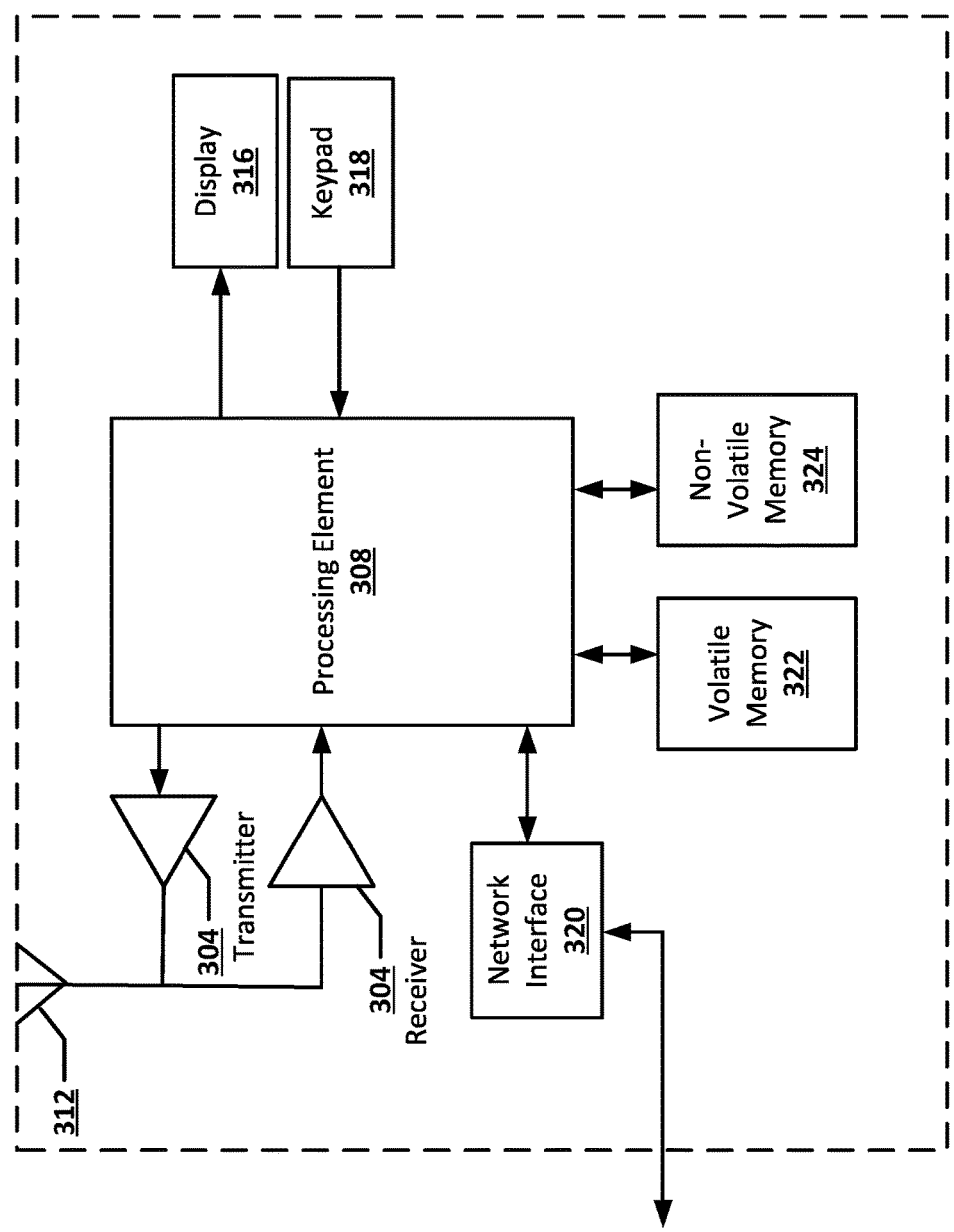

FIG. 3 provides an example client computing entity in accordance with some embodiments discussed herein.

Figure 4:
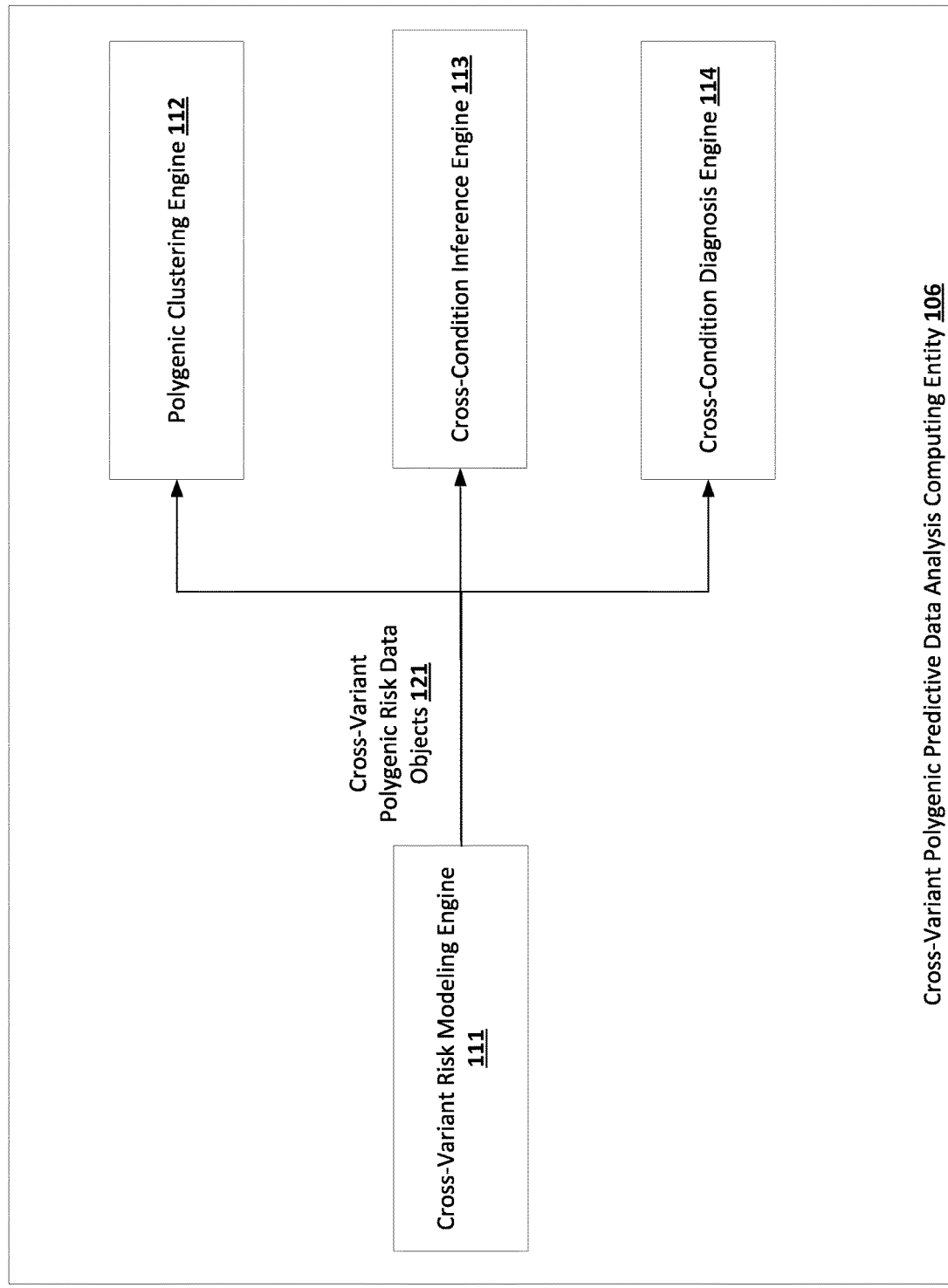

FIG. 4 is a data flow diagram of an example process for performing cross-variant polygenic predictive data analysis in accordance with some embodiments discussed herein.

Figure 5:
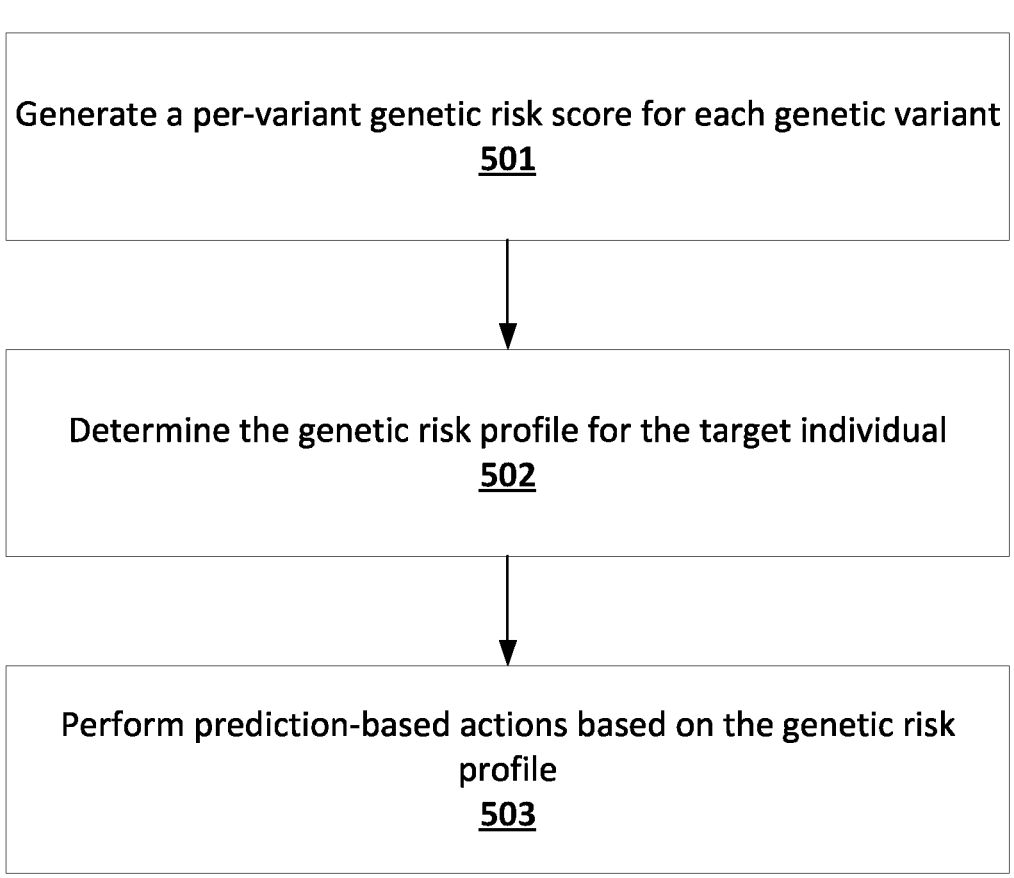

FIG. 5 provides an operational example of generating a genetic risk profile for a target individual with respect to a target medical condition in accordance with some embodiments discussed herein.

Figure 6:
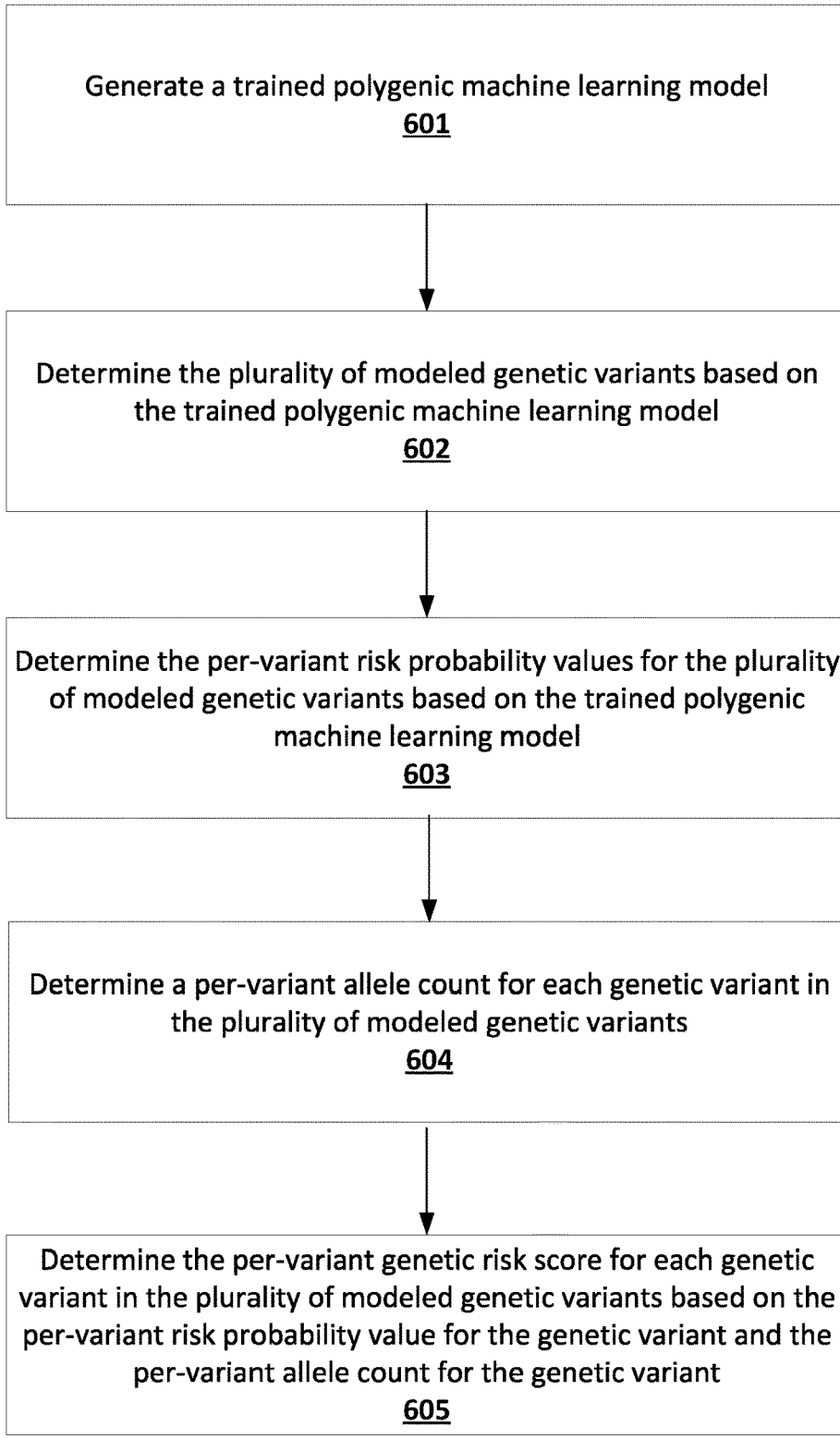

FIG. 6 is a flowchart diagram of an example process for generating per-variant genetic risk scores that relate to a genetic risk profile in accordance with some embodiments discussed herein.

Figure 7:
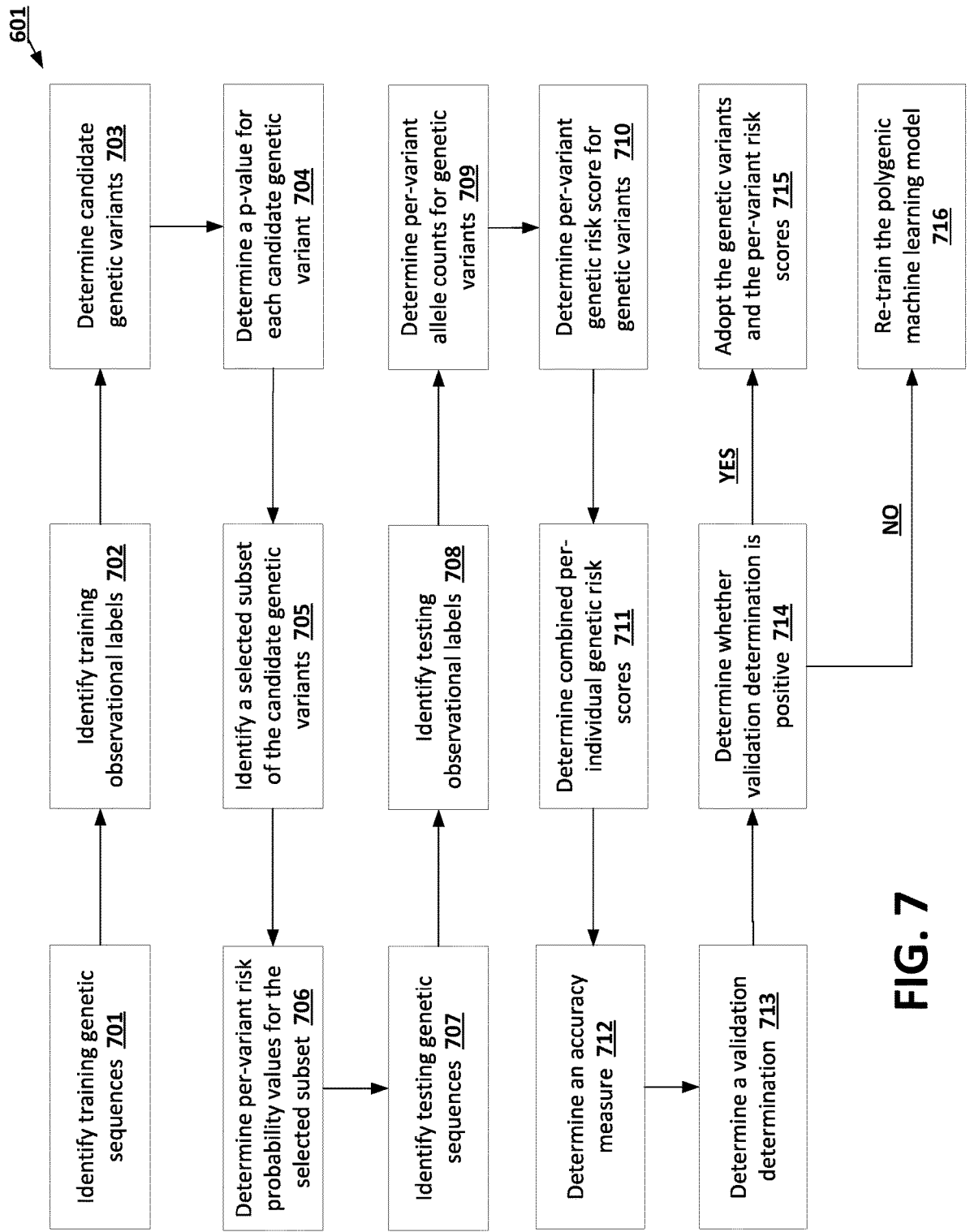

FIG. 7 is a flowchart diagram of an example process for generating a trained polygenic machine learning model in accordance with some embodiments discussed herein.

Figure 8:
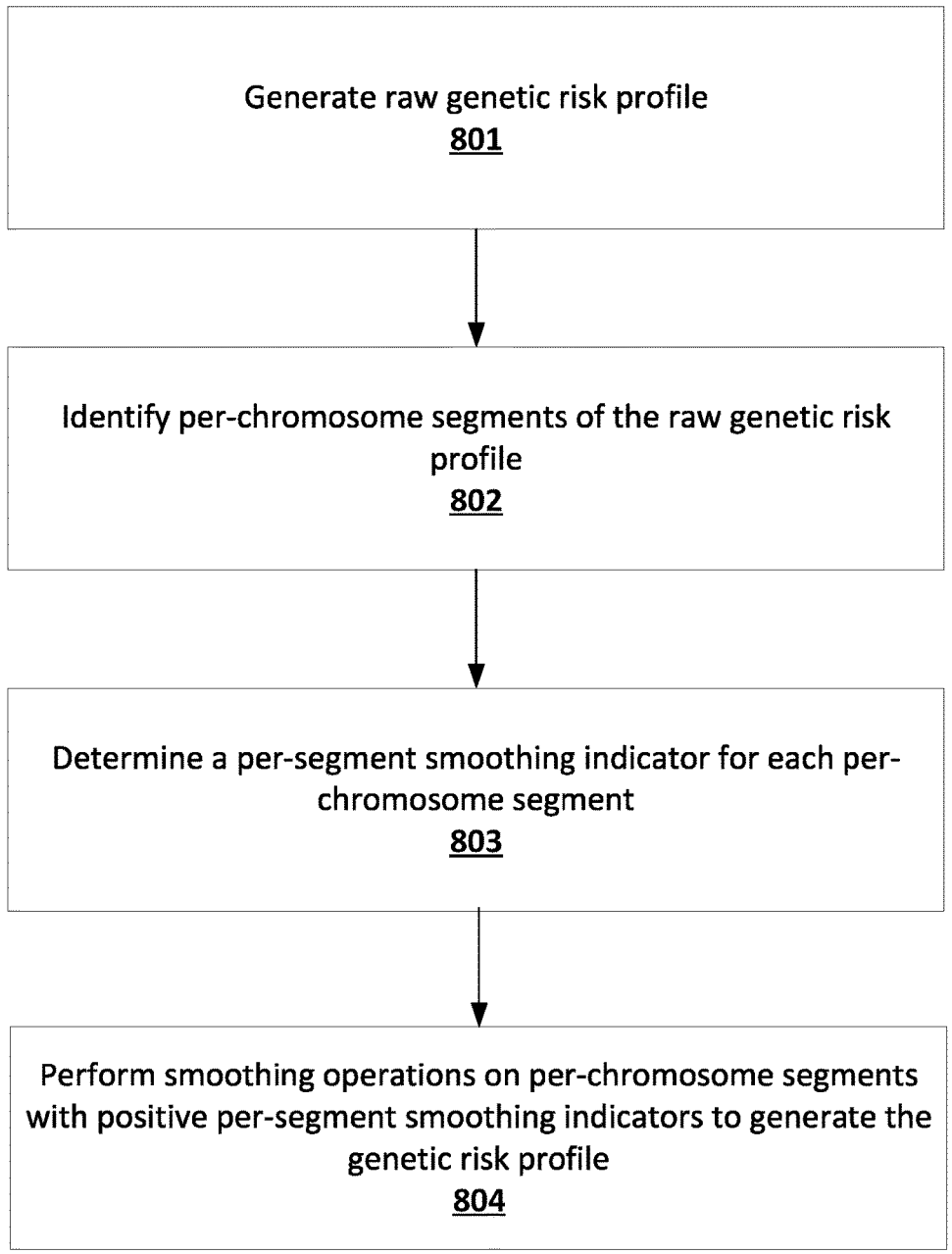

FIG. 8 is a flowchart diagram of an example process for generating a genetic risk profile in accordance with some embodiments discussed herein.

Figure 9:
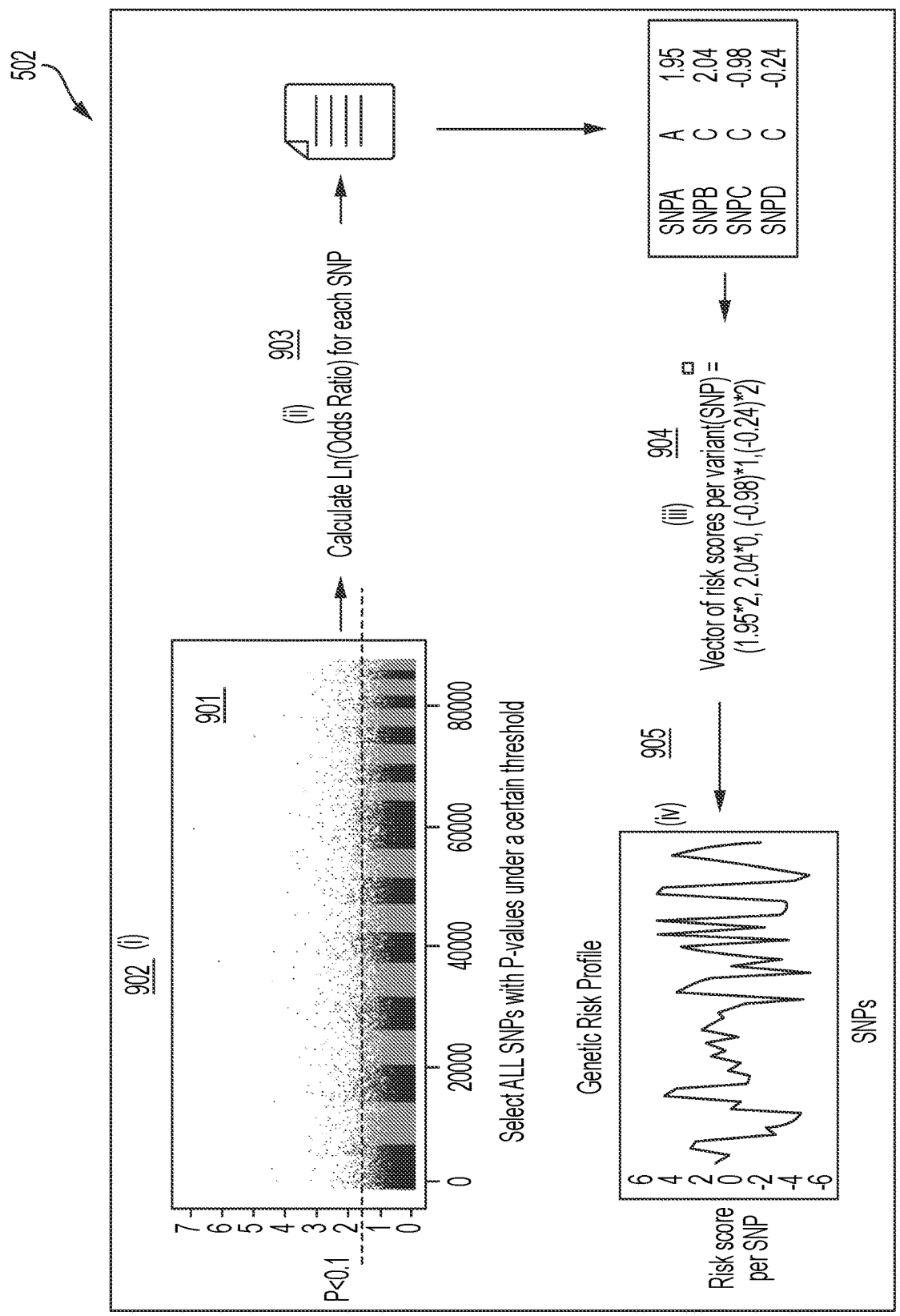

FIG. 9 provides an operational example of an example process for generating a genetic risk profile in accordance with some embodiments discussed herein.

Figure 10:
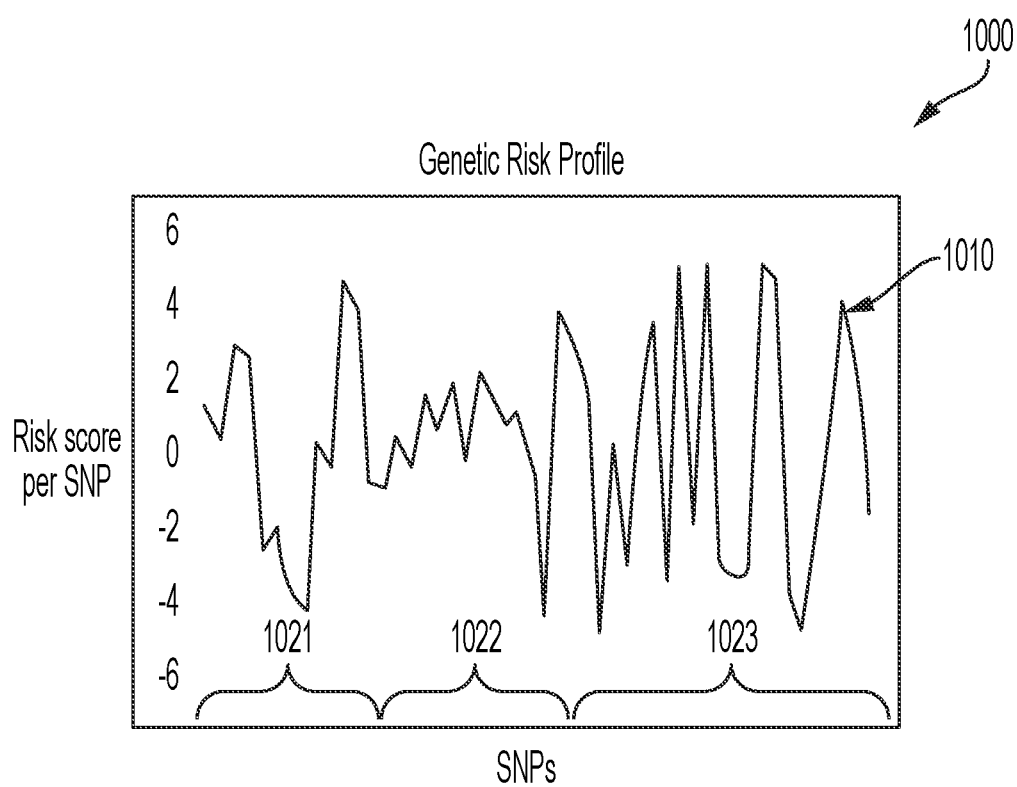

FIG. 10 provides an operational example of a chromosome-based predictive output interface in accordance with some embodiments discussed herein.

Figure 11:
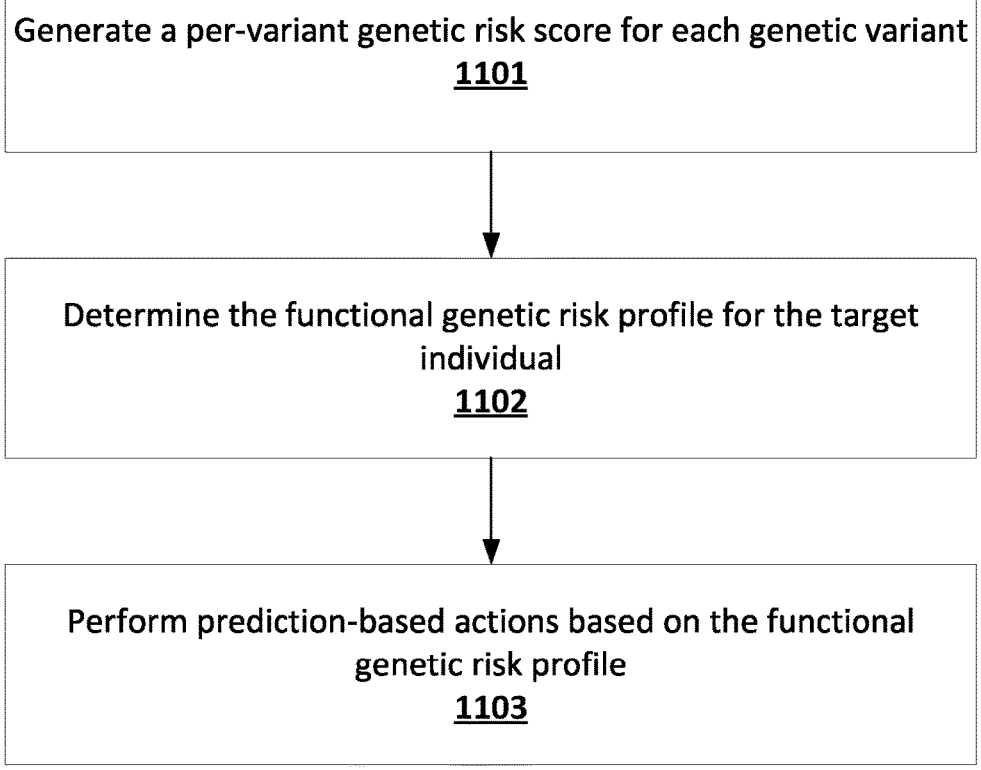

FIG. 11 is a flowchart diagram of an example process for generating a functional genetic risk profile for a target individual with respect to a target medical condition in accordance with some embodiments discussed herein.

Figure 12:
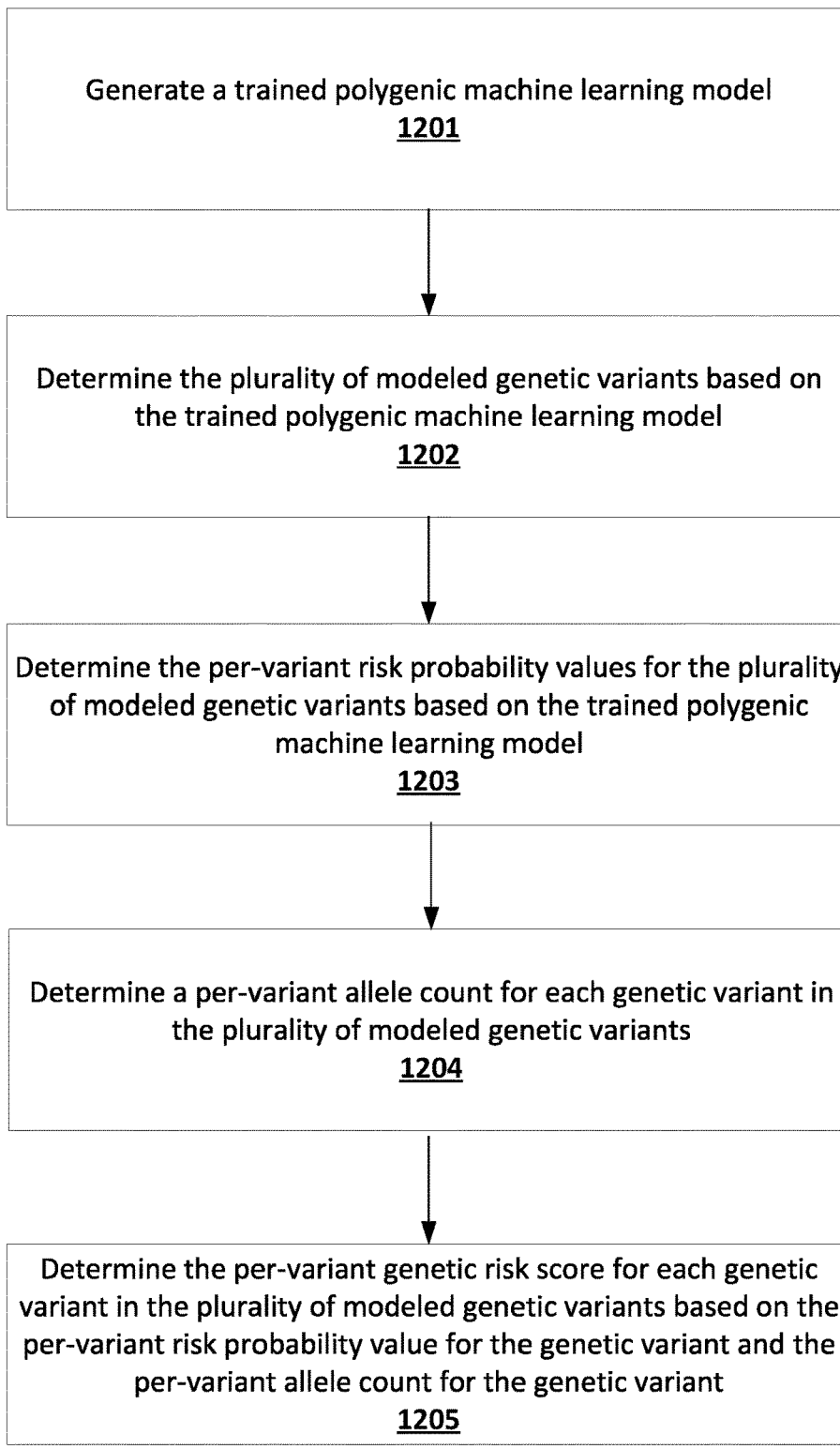

FIG. 12 is a flowchart diagram of an example process for generating per-variant genetic risk scores that relate to a functional genetic risk profile in accordance with some embodiments discussed herein.

Figure 13:
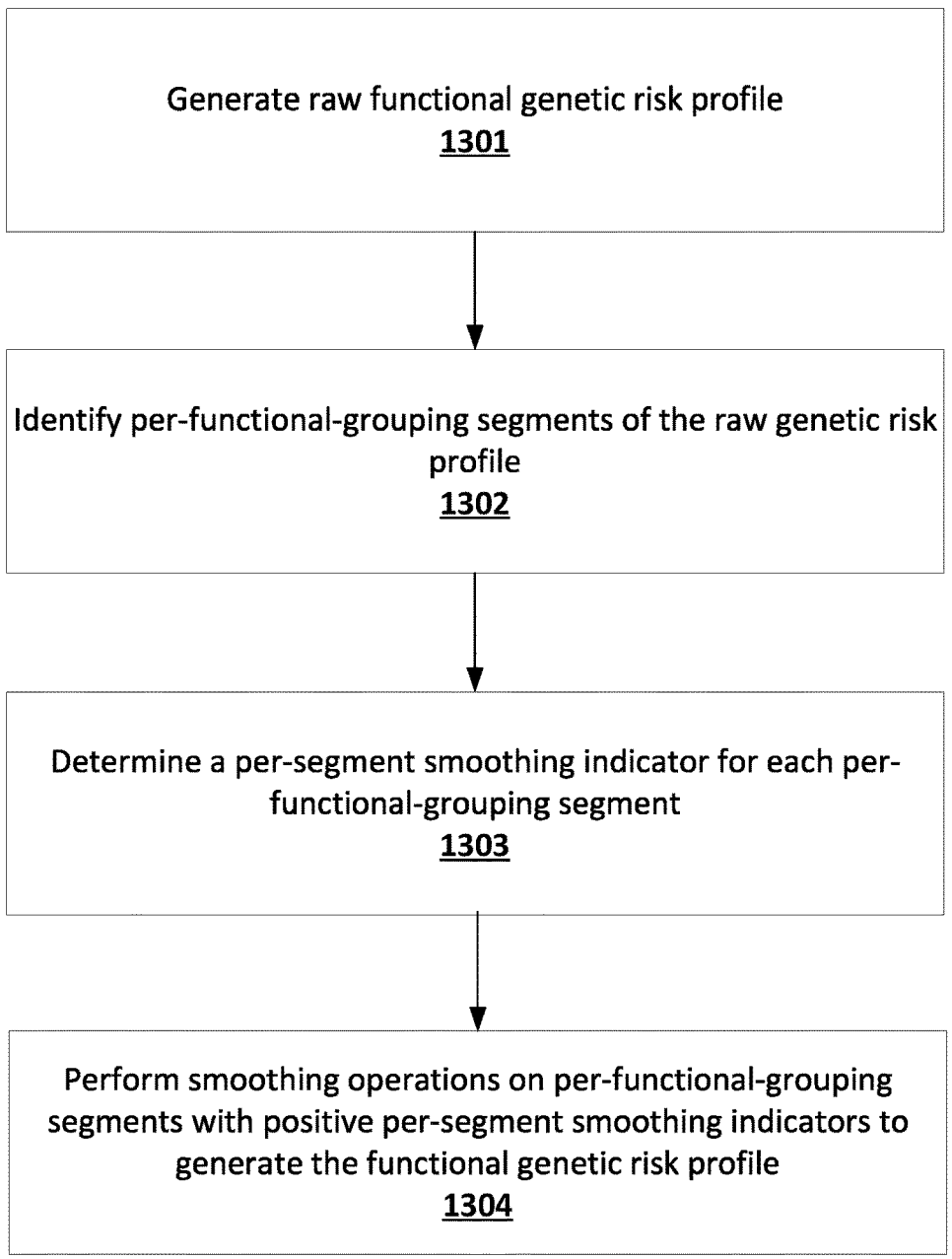

FIG. 13 is a flowchart diagram of an example process for generating a functional genetic risk profile in accordance with some embodiments discussed herein.

Figure 14:
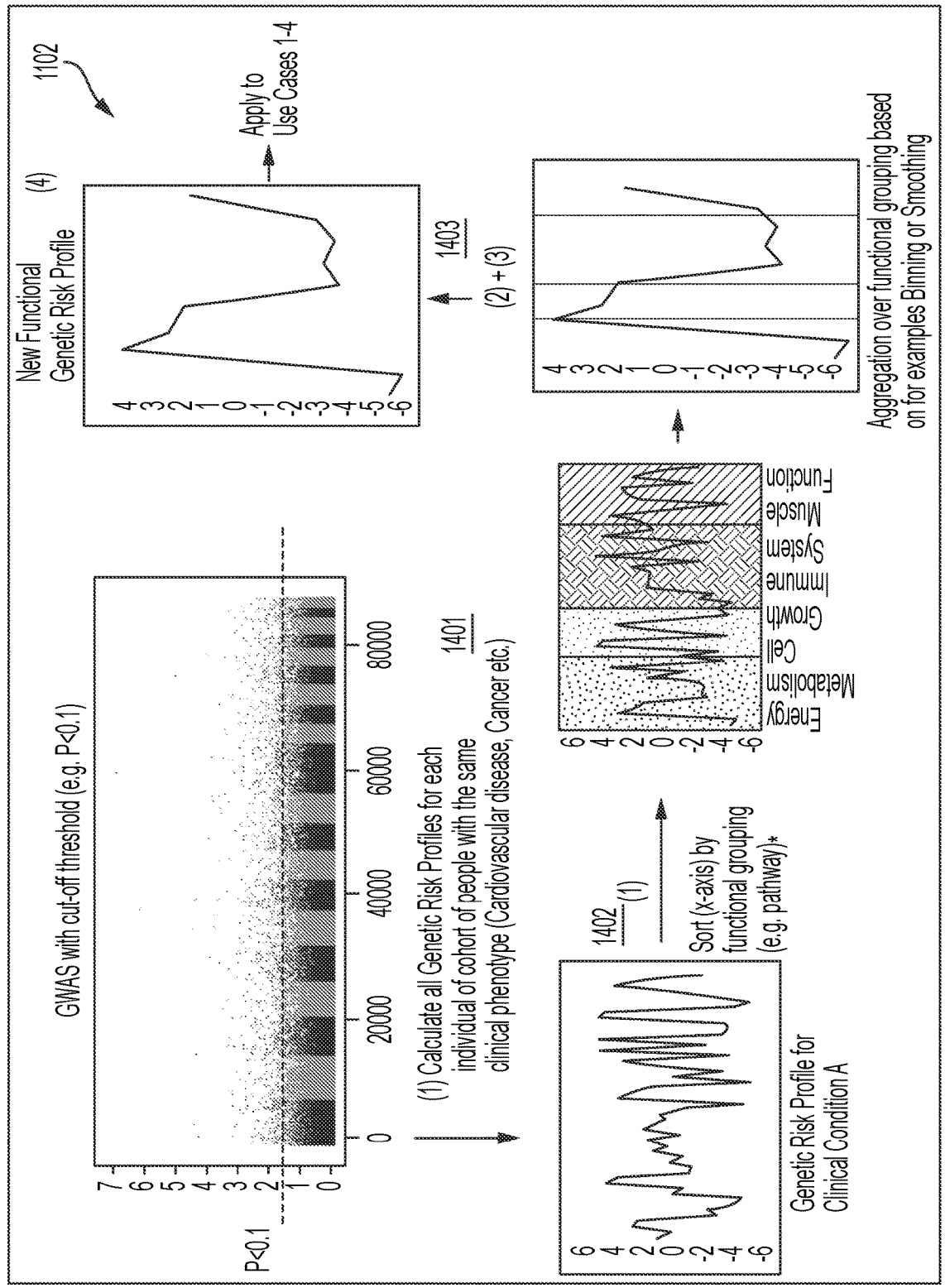

FIG. 14 provides an operational example of an example process for generating a functional genetic risk profile in accordance with some embodiments discussed herein.

Figure 15:
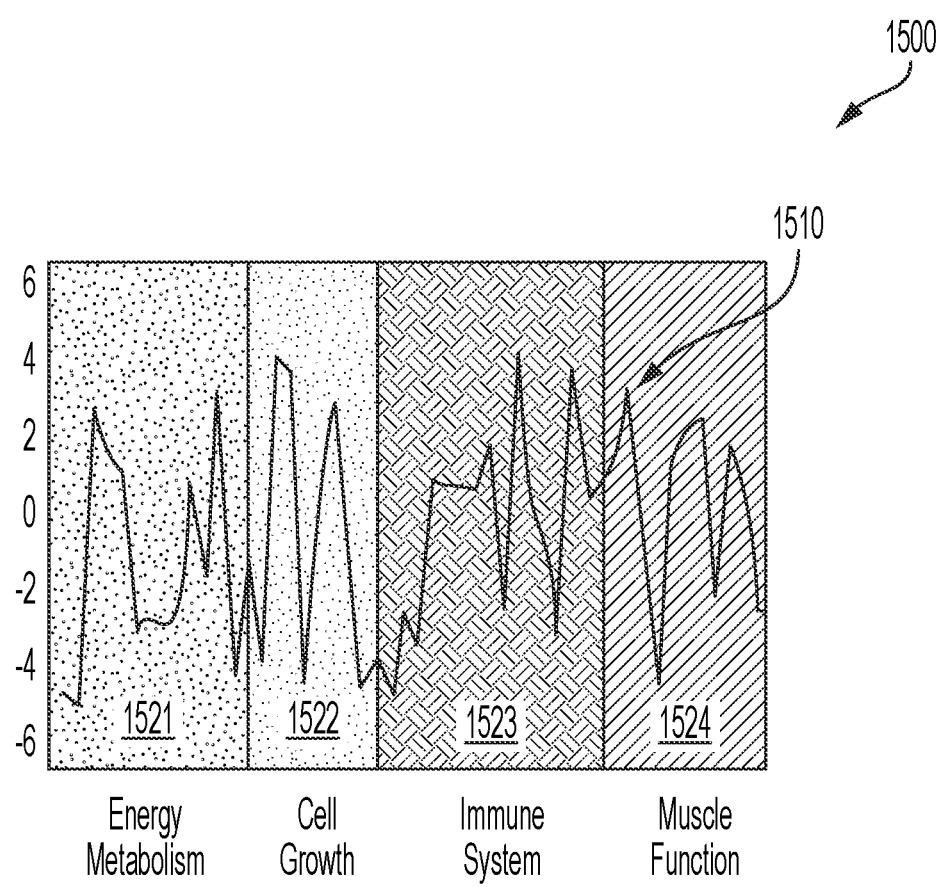

FIG. 15 provides an operational example of a functional-grouping-based predictive output interface in accordance with some embodiments discussed herein.

Figure 16:
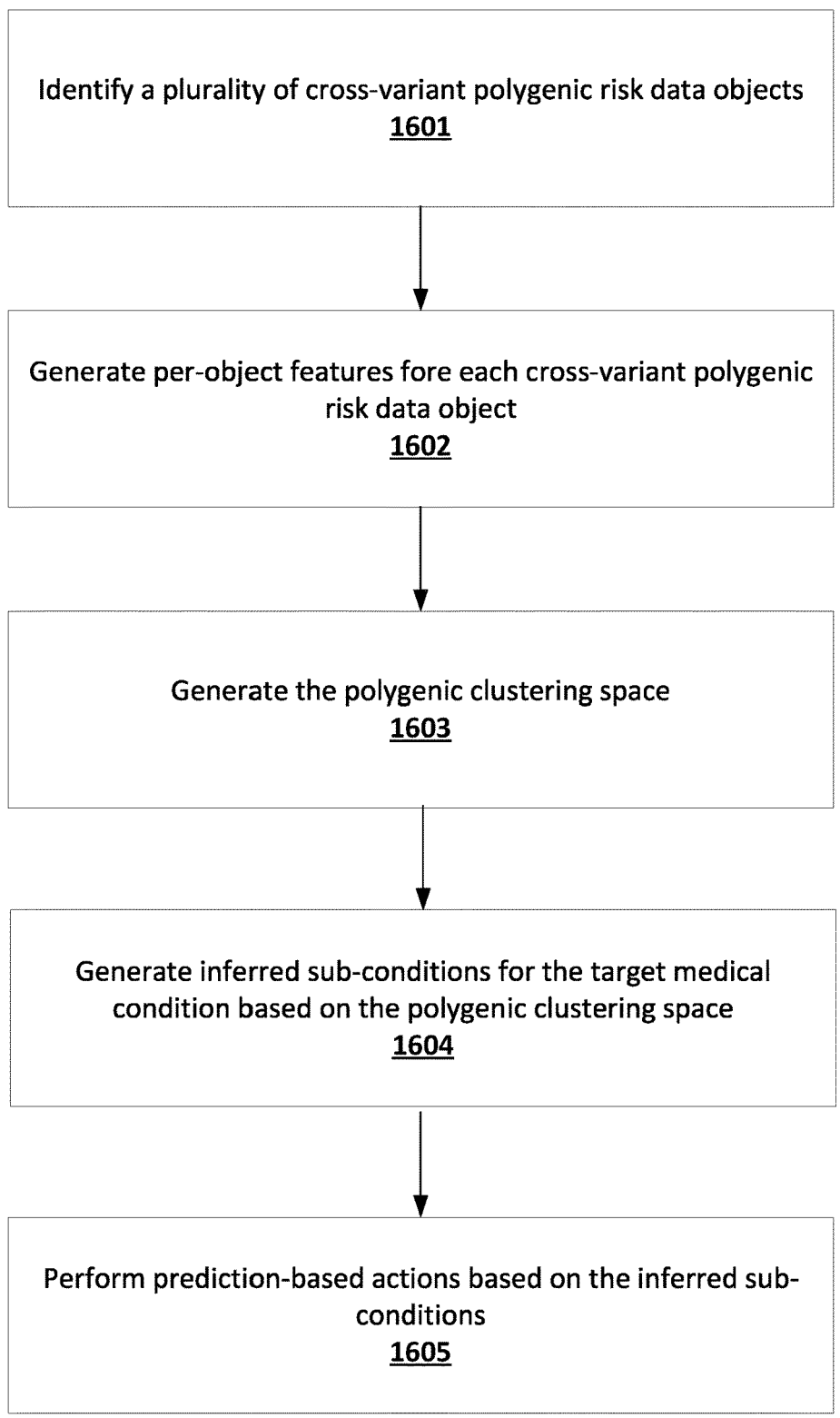

FIG. 16 is a flowchart diagram of an example process for performing per-condition polygenic clustering of a plurality of individuals associated with a target medical condition in accordance with some embodiments discussed herein.

Figure 17:
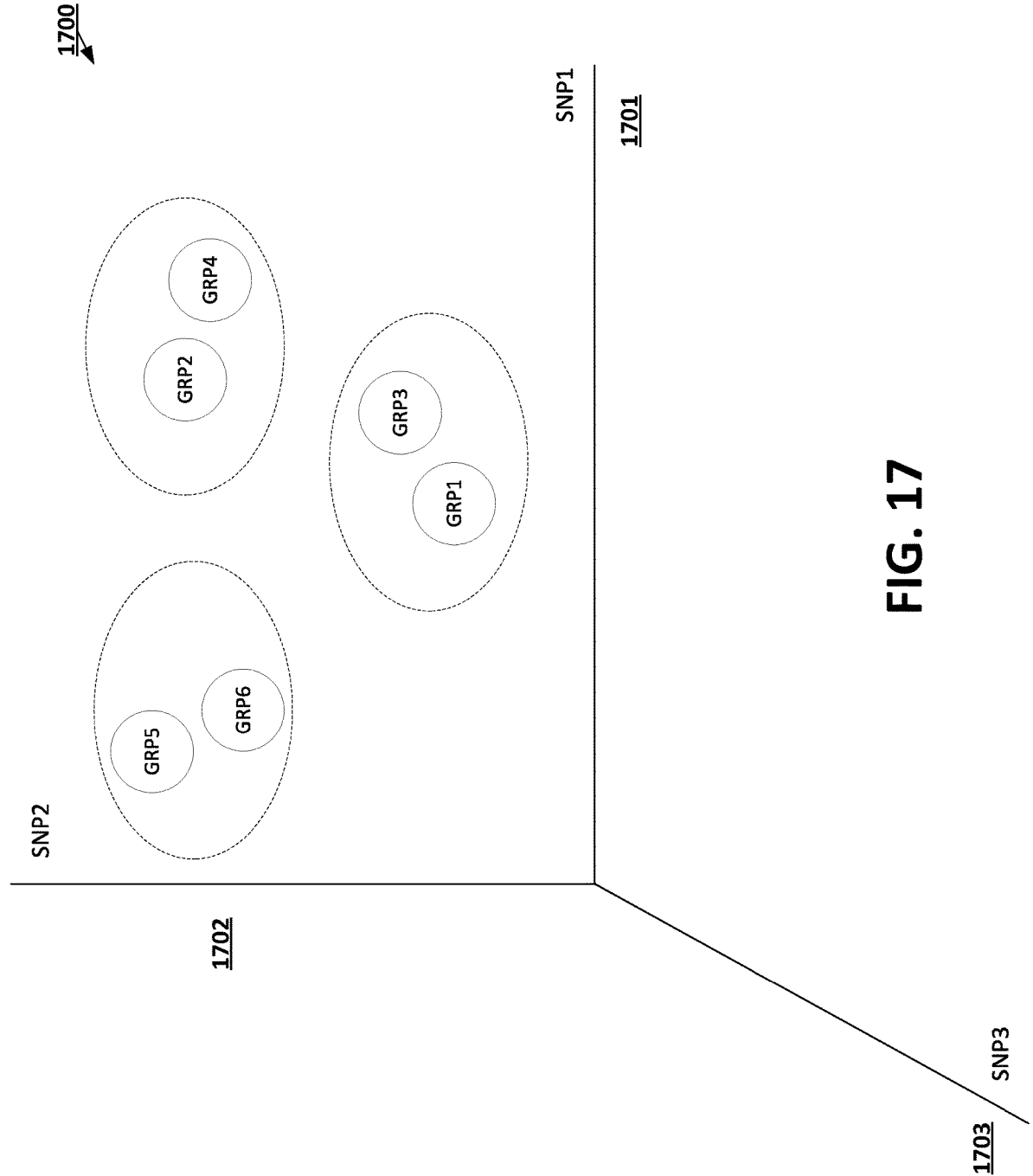

FIG. 17 provides an operational example of a polygenic clustering space in accordance with some embodiments discussed herein.

Figure 18:
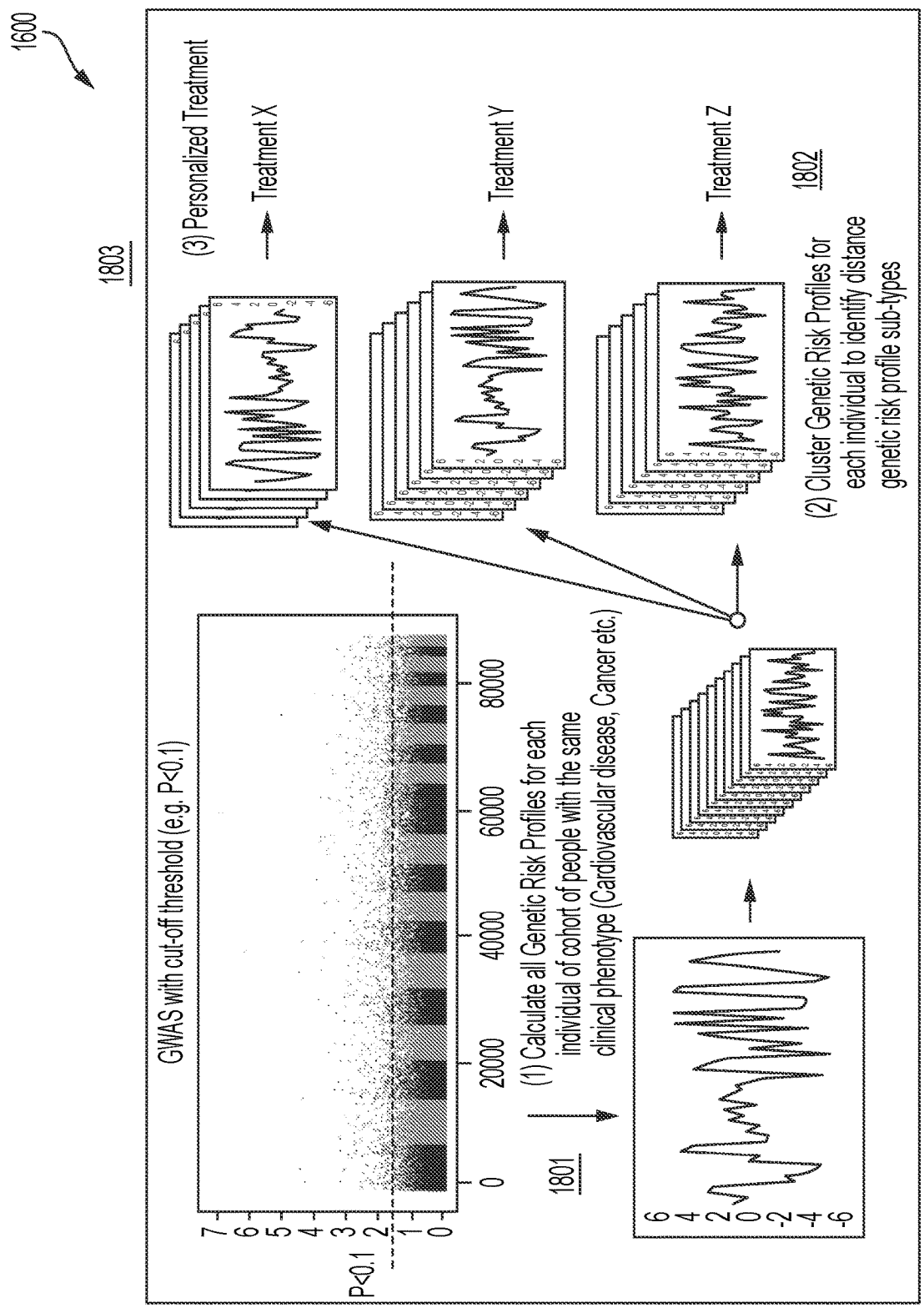

FIG. 18 provides an operational example of an example process for performing per-condition polygenic clustering with some embodiments discussed herein.

Figure 19:
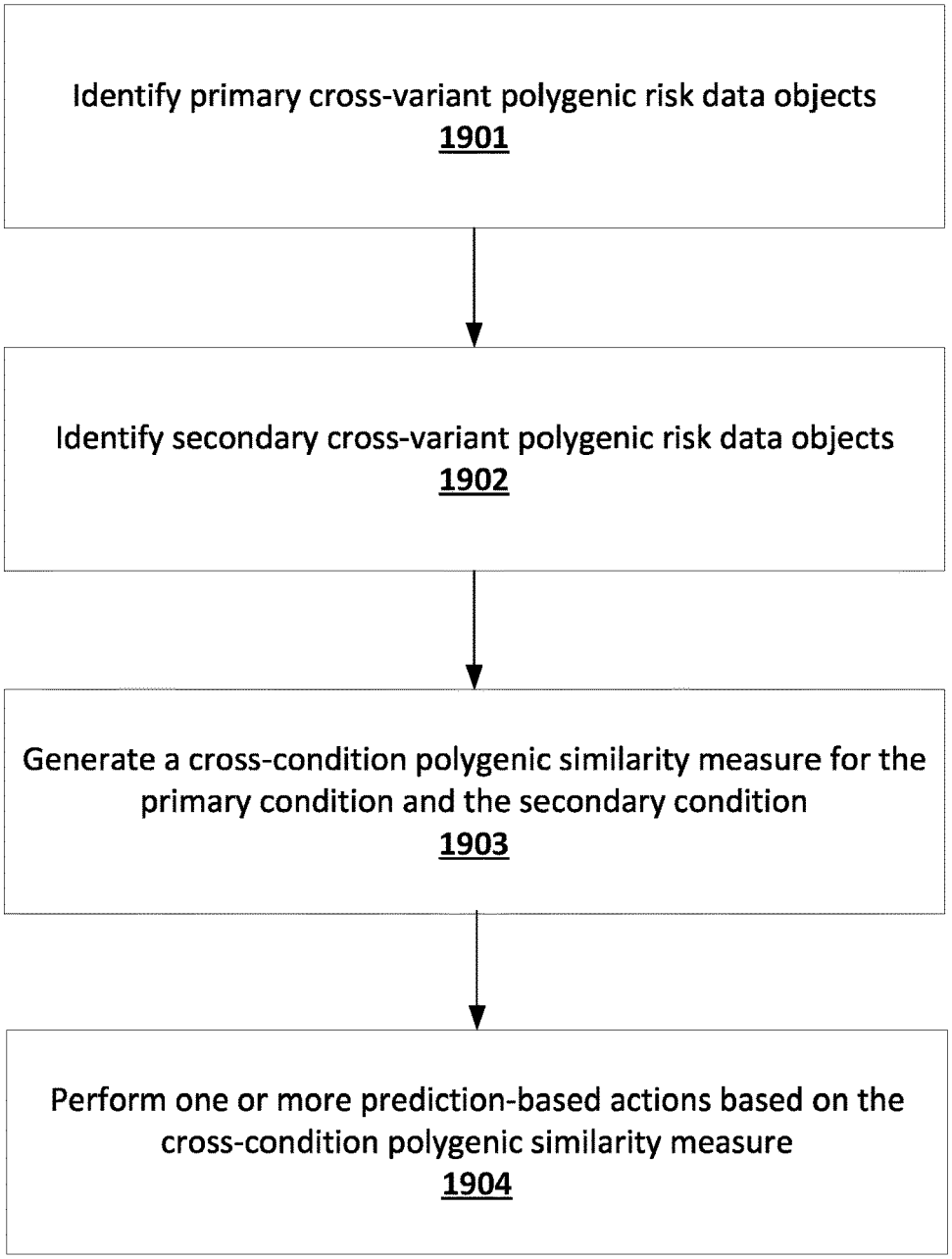

FIG. 19 is a flowchart diagram of an example process for performing cross-condition polygenic predictive inference with respect to a primary medical condition and a secondary medical condition in accordance with some embodiments discussed herein.

Figure 20:
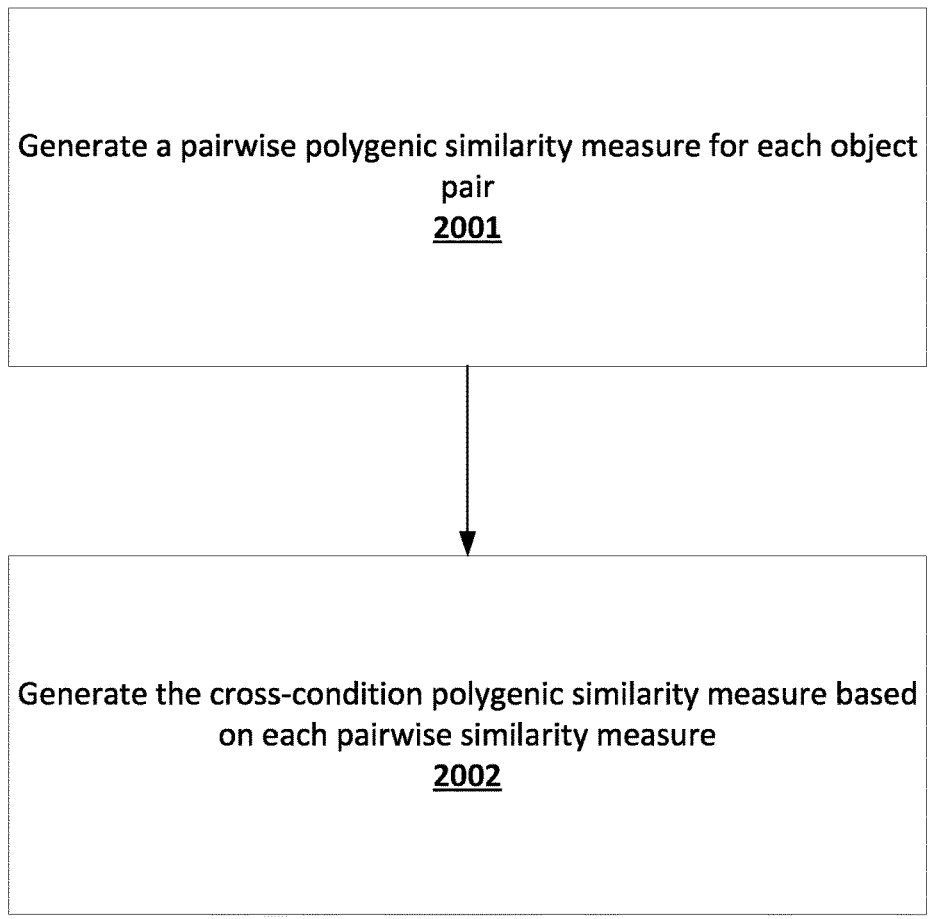

FIG. 20 is a flowchart diagram of an example process for generating a cross-condition polygenic similarity measure in accordance with some embodiments discussed herein.

Figure 21:
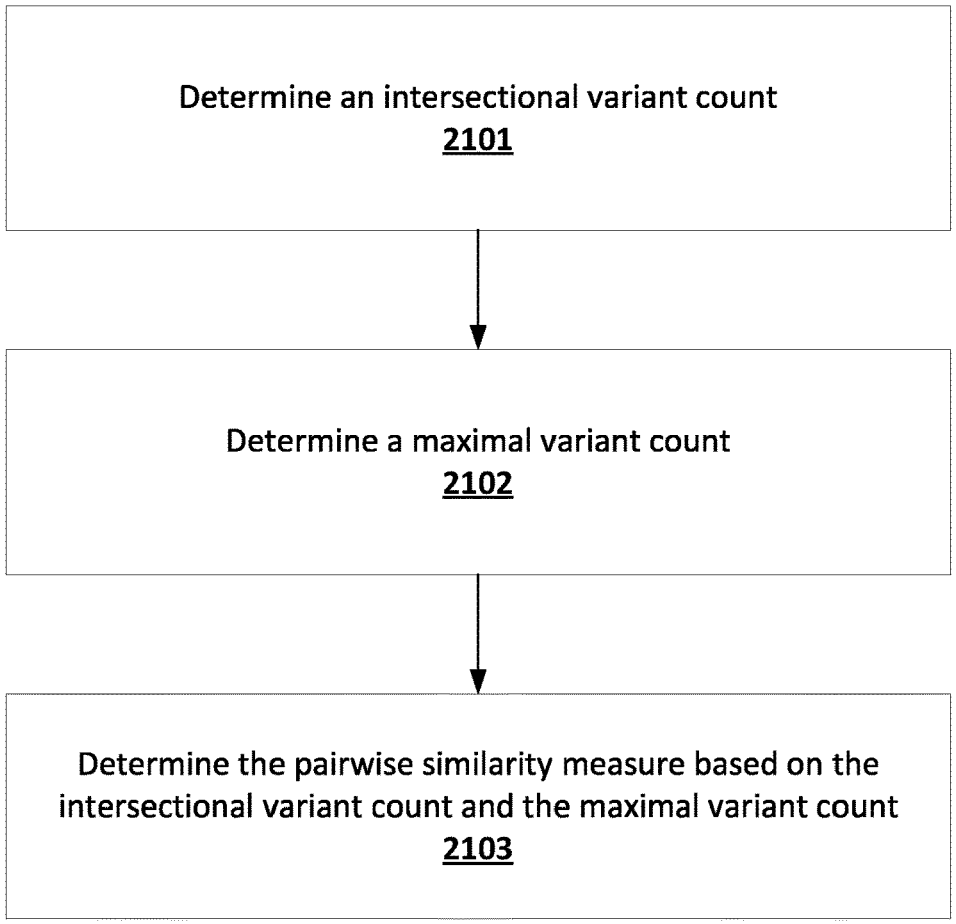

FIG. 21 is a flowchart diagram of an example process for determining a pairwise similarity measure for a pair of cross-variant polygenic risk data objects using maximal variant counts in accordance with some embodiments discussed herein.

Figure 22:
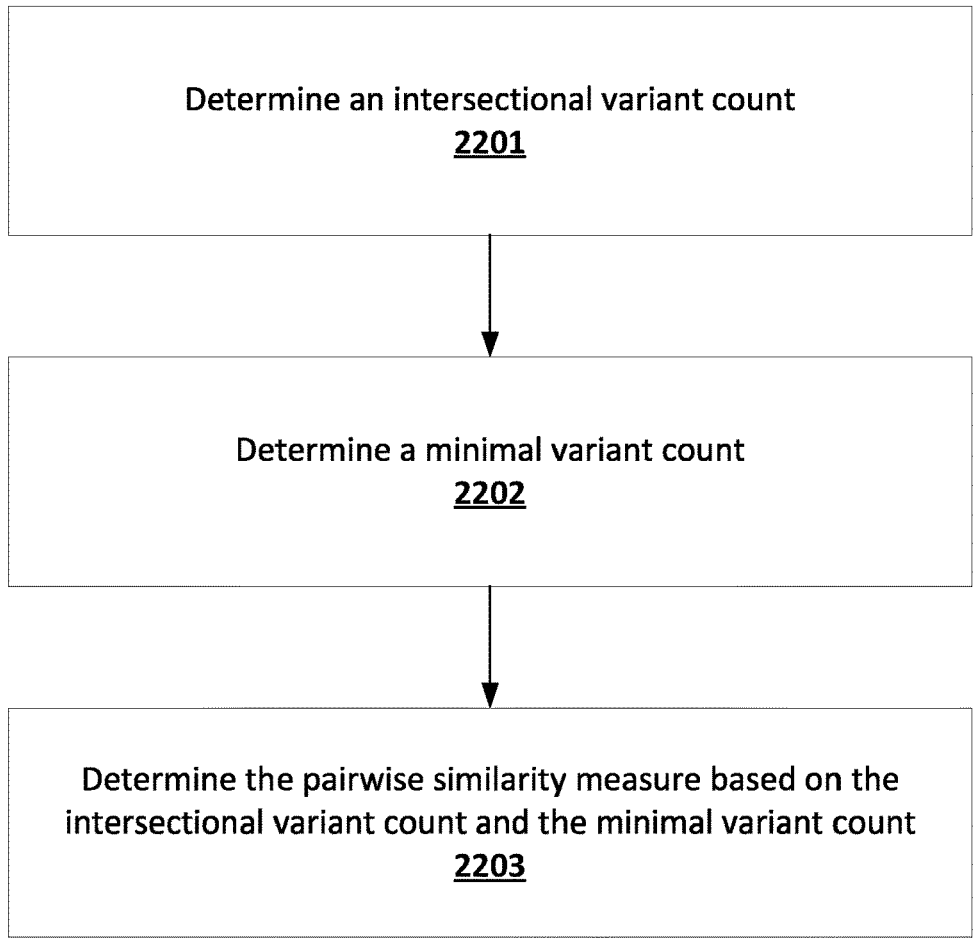

FIG. 22 is a flowchart diagram of an example process for determining a pairwise similarity measure for a pair of cross-variant polygenic risk data objects using minimal variant counts in accordance with some embodiments discussed herein.

Figure 23:
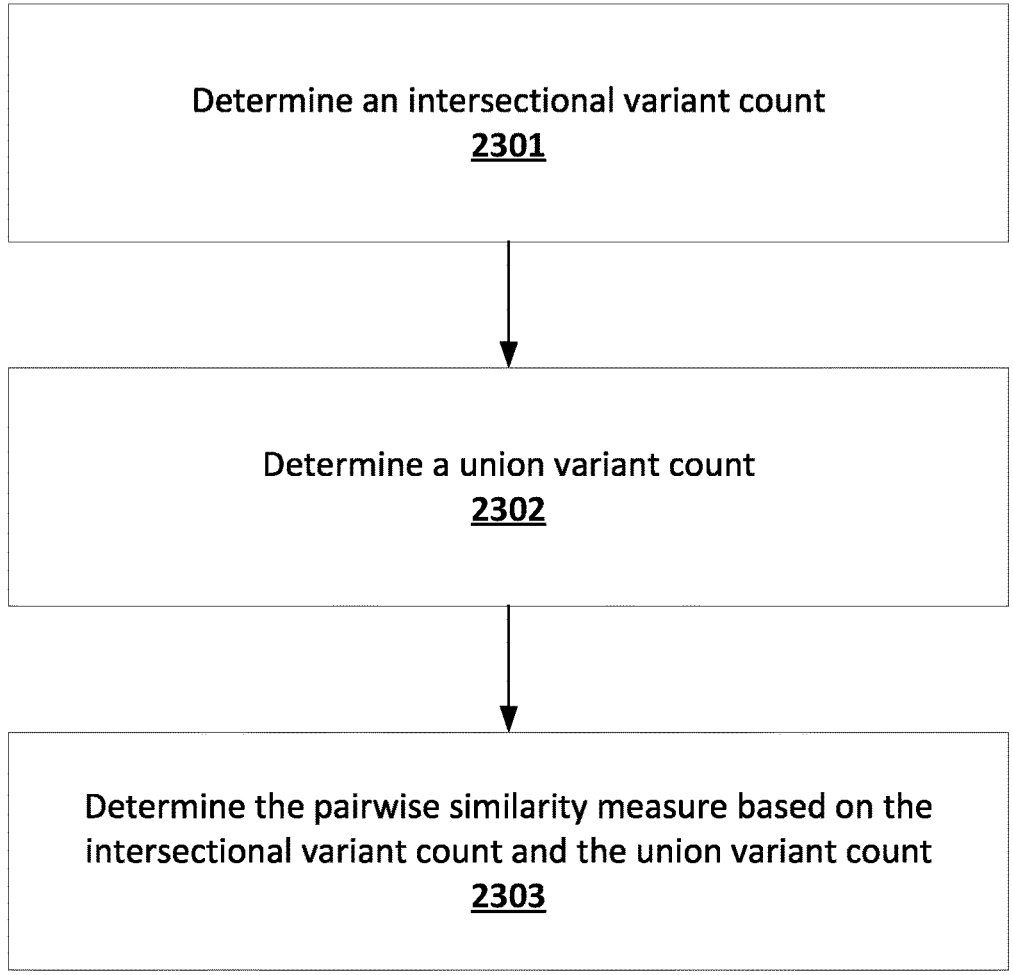

FIG. 23 is a flowchart diagram of an example process for determining a pairwise similarity measure for a pair of cross-variant polygenic risk data objects using union variant counts in accordance with some embodiments discussed herein.

Figure 24:
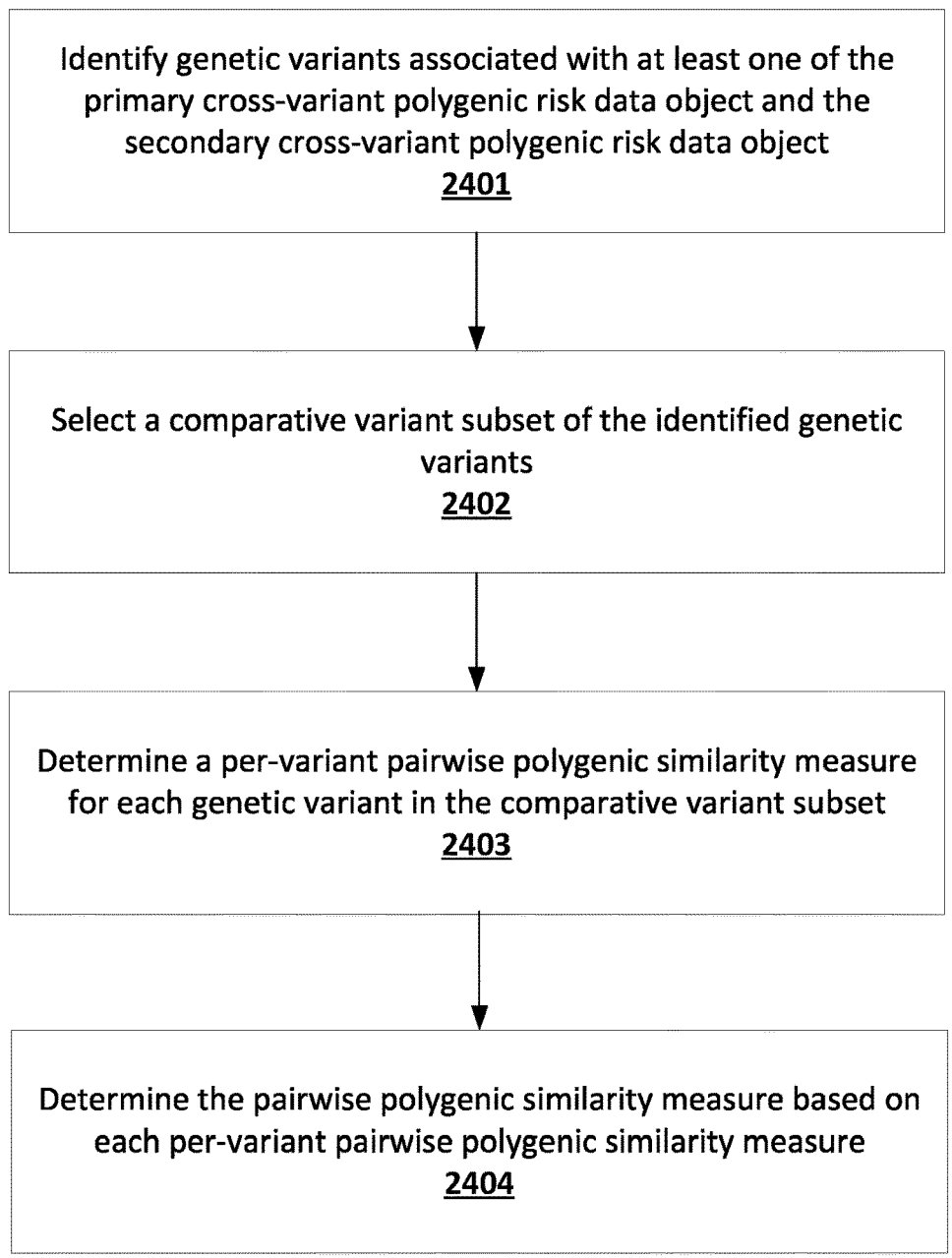

FIG. 24 is a flowchart diagram of an example process for determining a pairwise similarity measure for a pair of cross-variant polygenic risk data objects using per-variant genetic risk scores for genetic variants in a comparative variant subset in accordance with some embodiments discussed herein.

Figure 25:
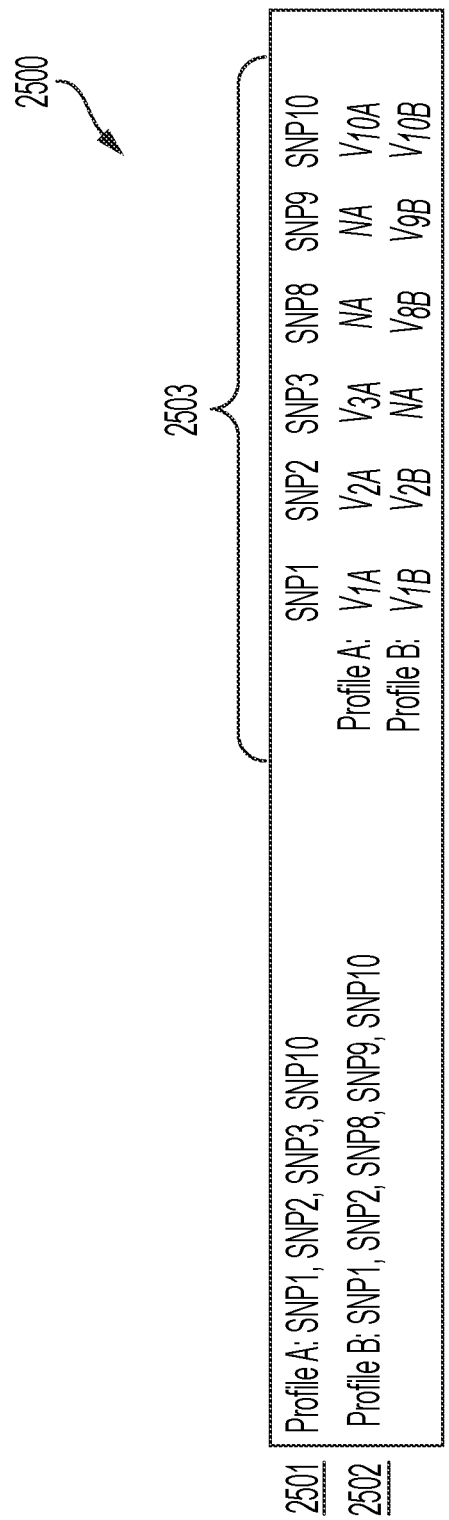

FIG. 25 provides an operational example of a per-variant pairwise polygenic similarity data object in accordance with some embodiments discussed herein.

Figure 26A:
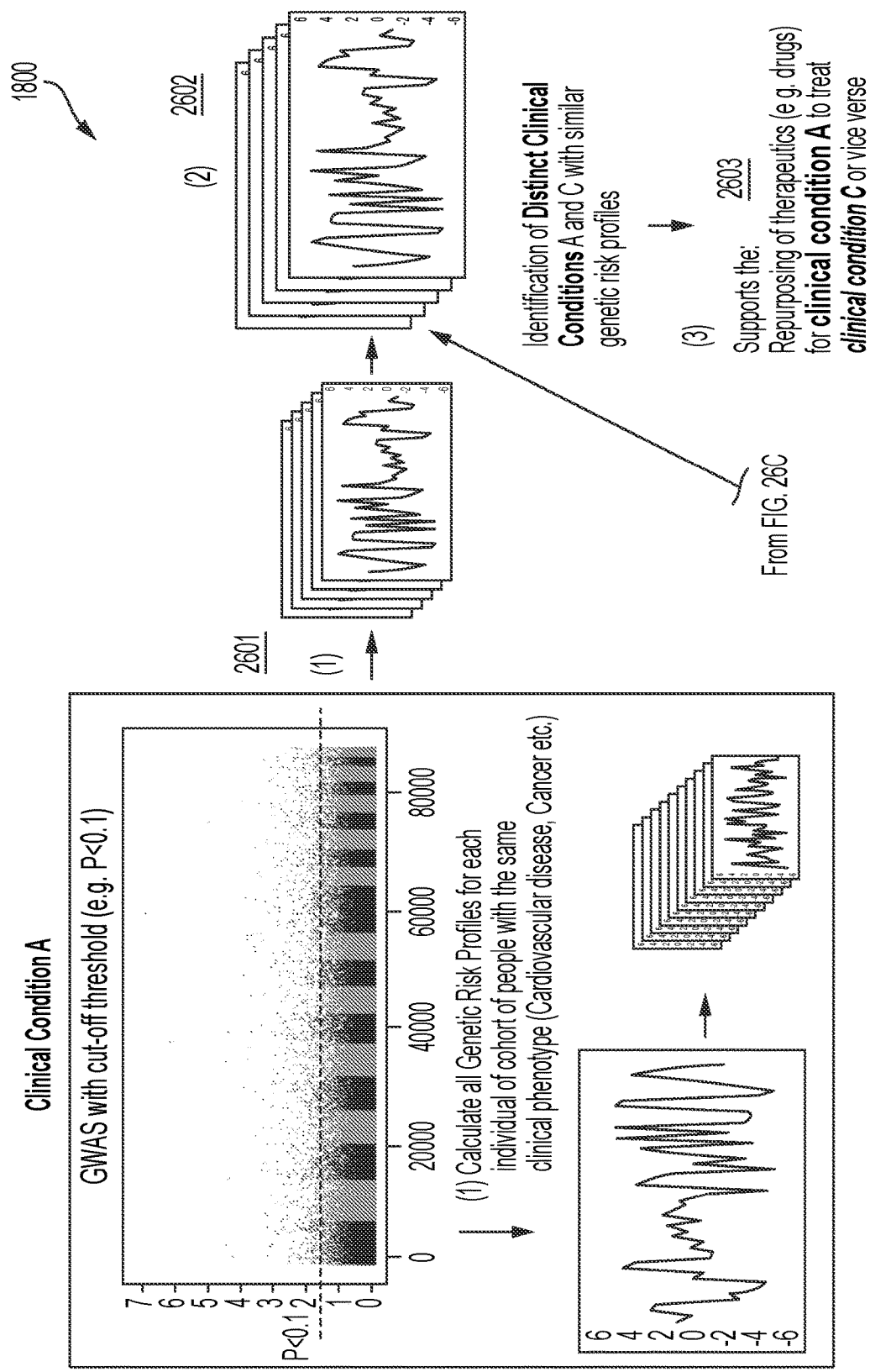
Figure 26B:
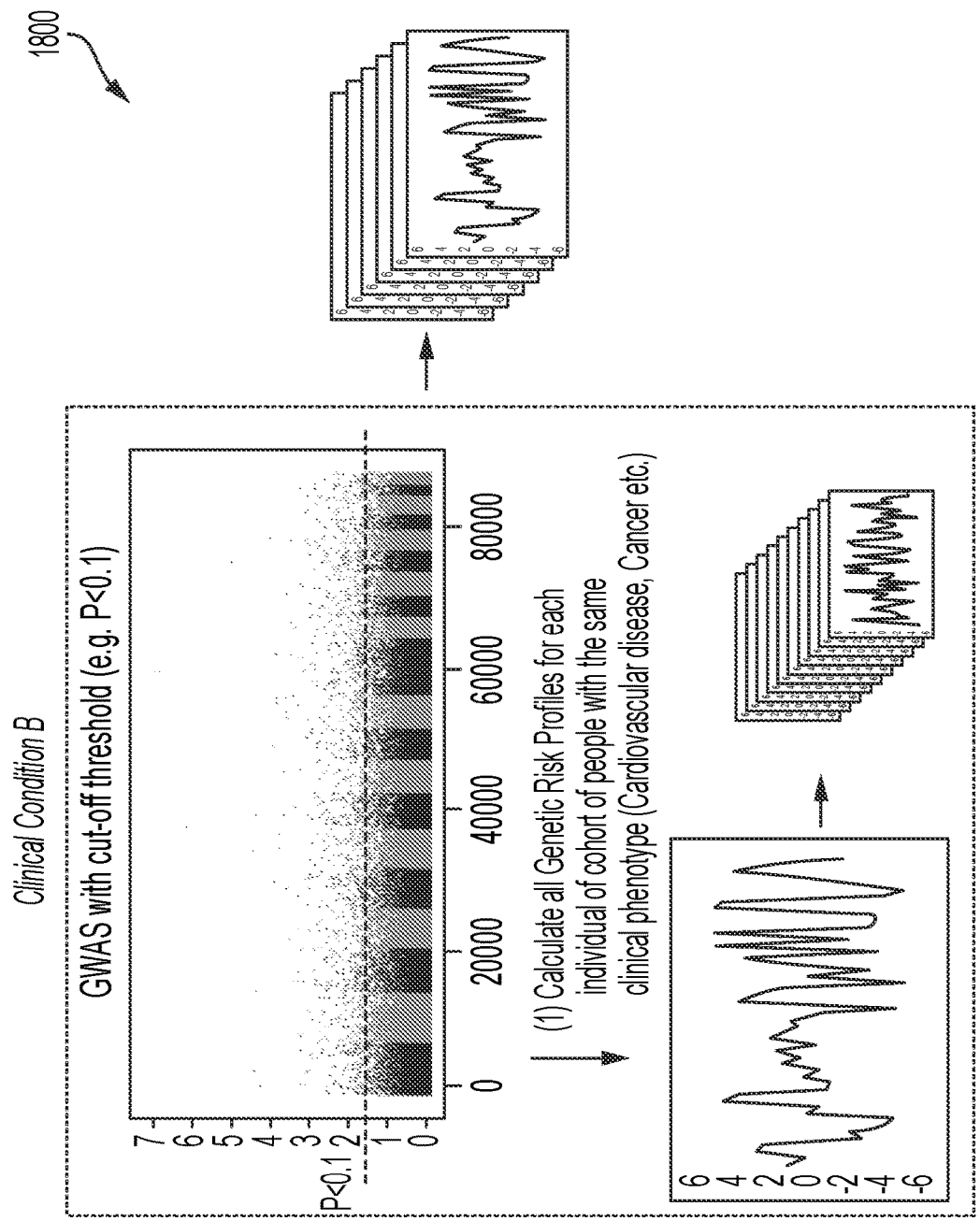
Figure 26C:
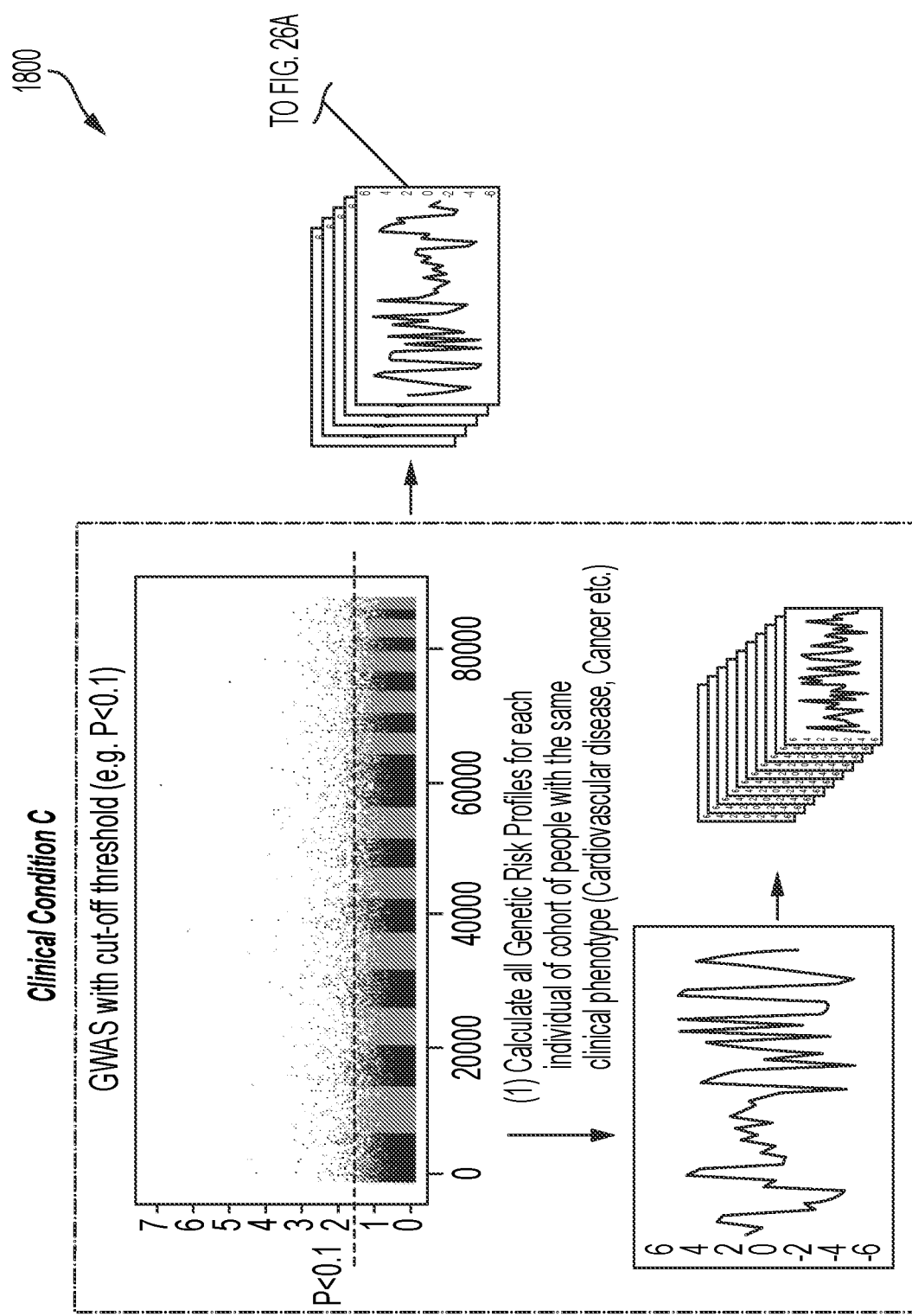

FIGS. 26A, 26B, and 26C provide an operational example of an example process for performing cross-condition polygenic predictive inference in accordance with some embodiments discussed herein.

Figure 27:
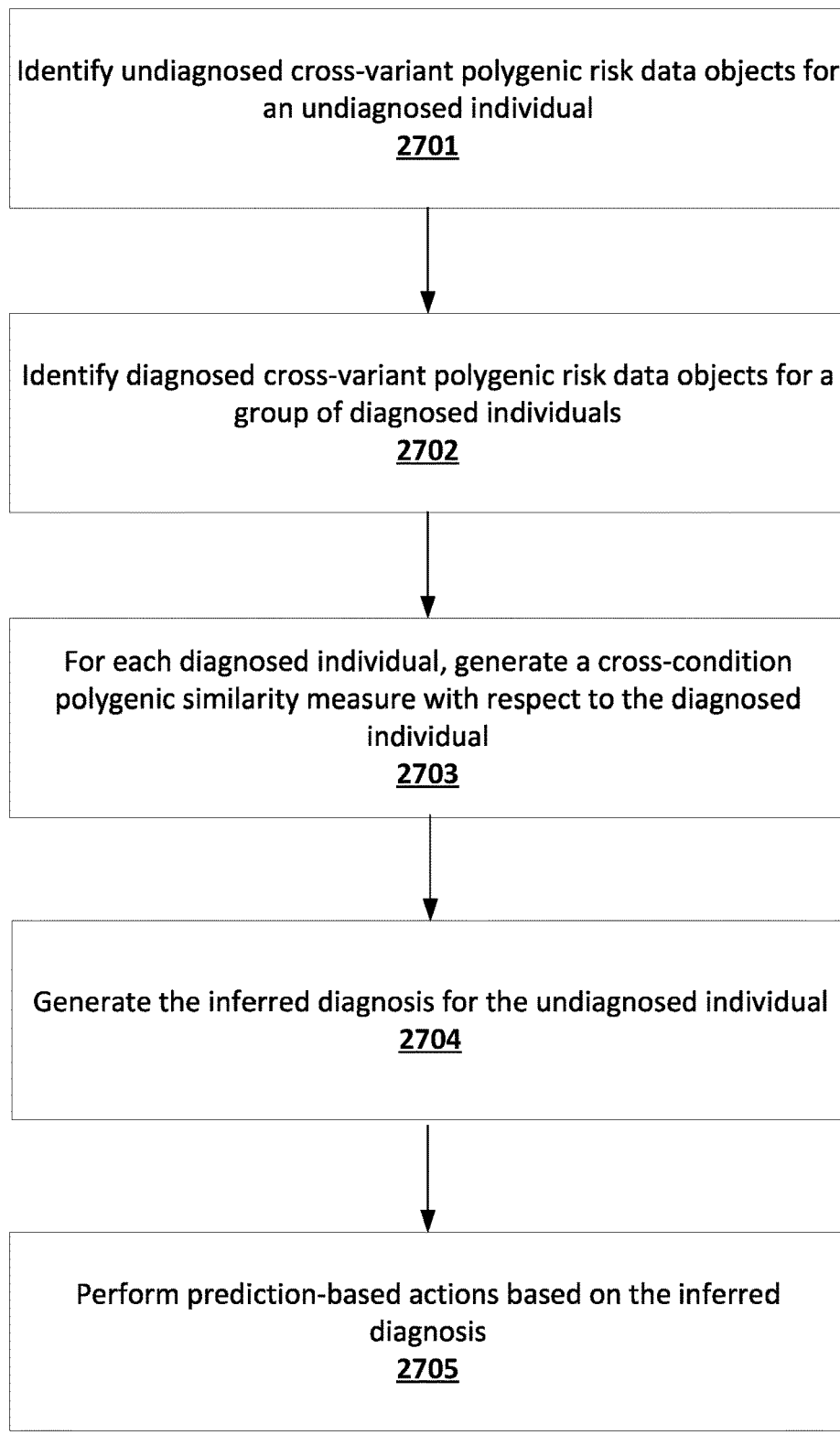
Figure 28A:
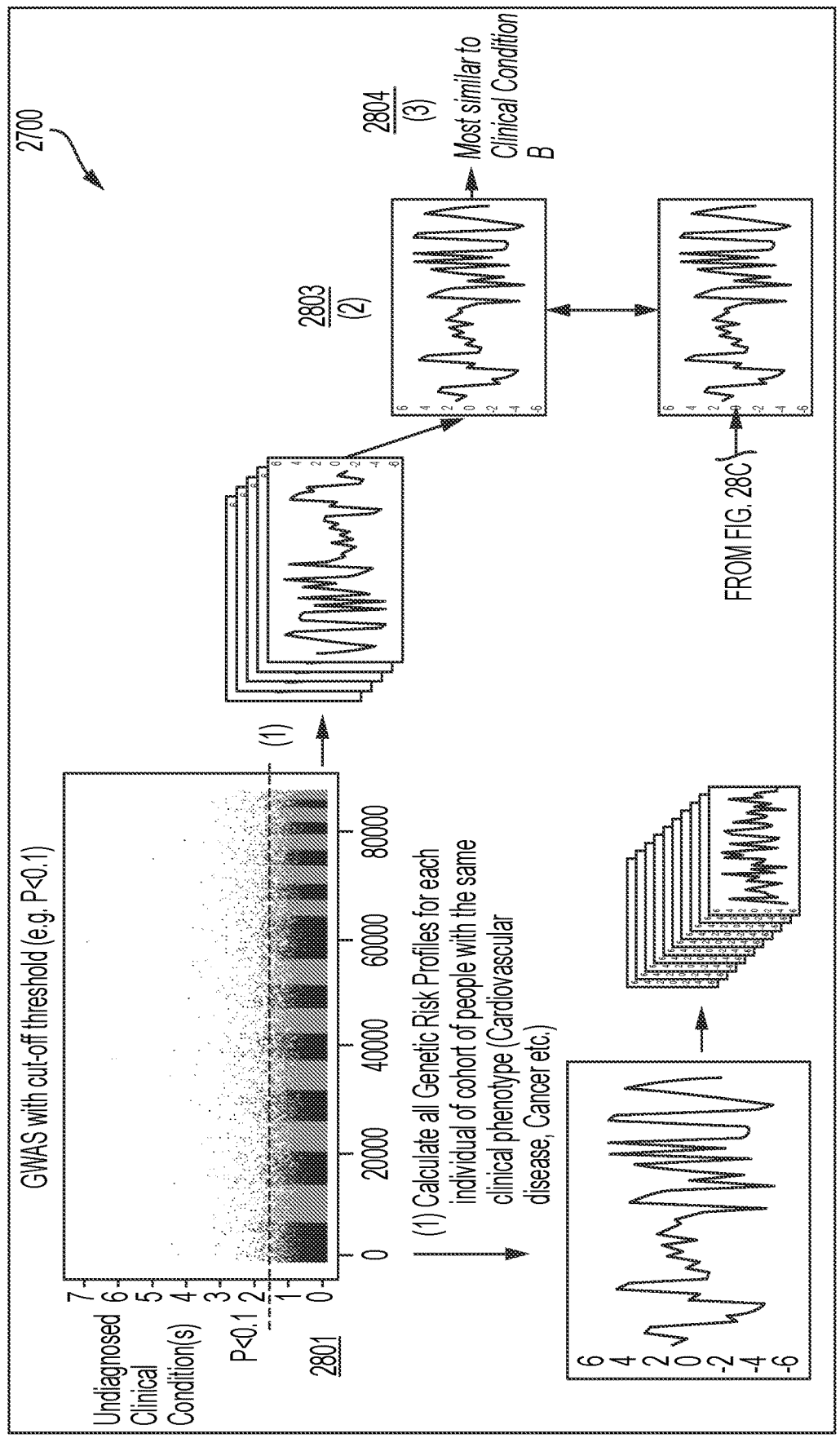
Figure 28B:
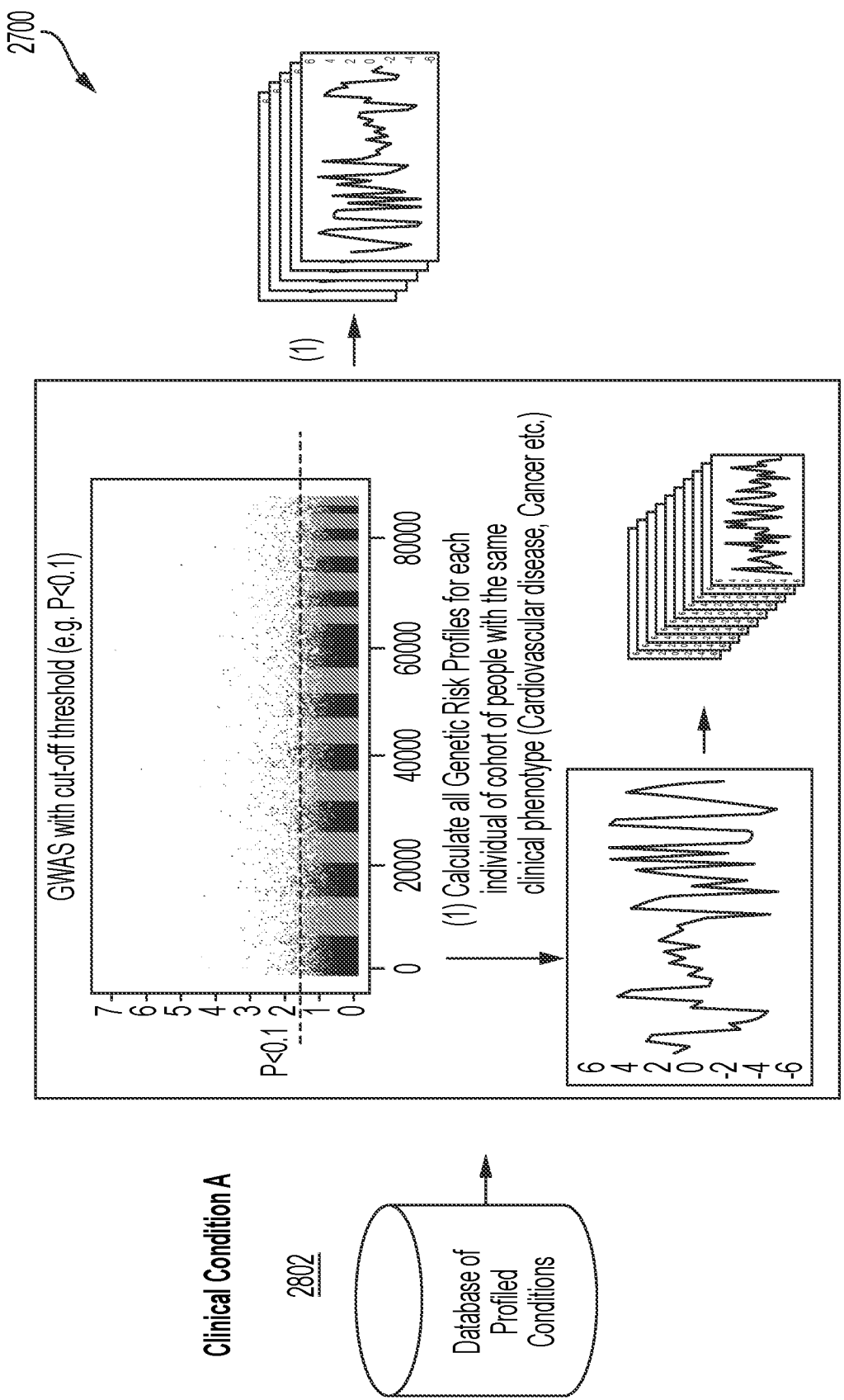
Figure 28C:
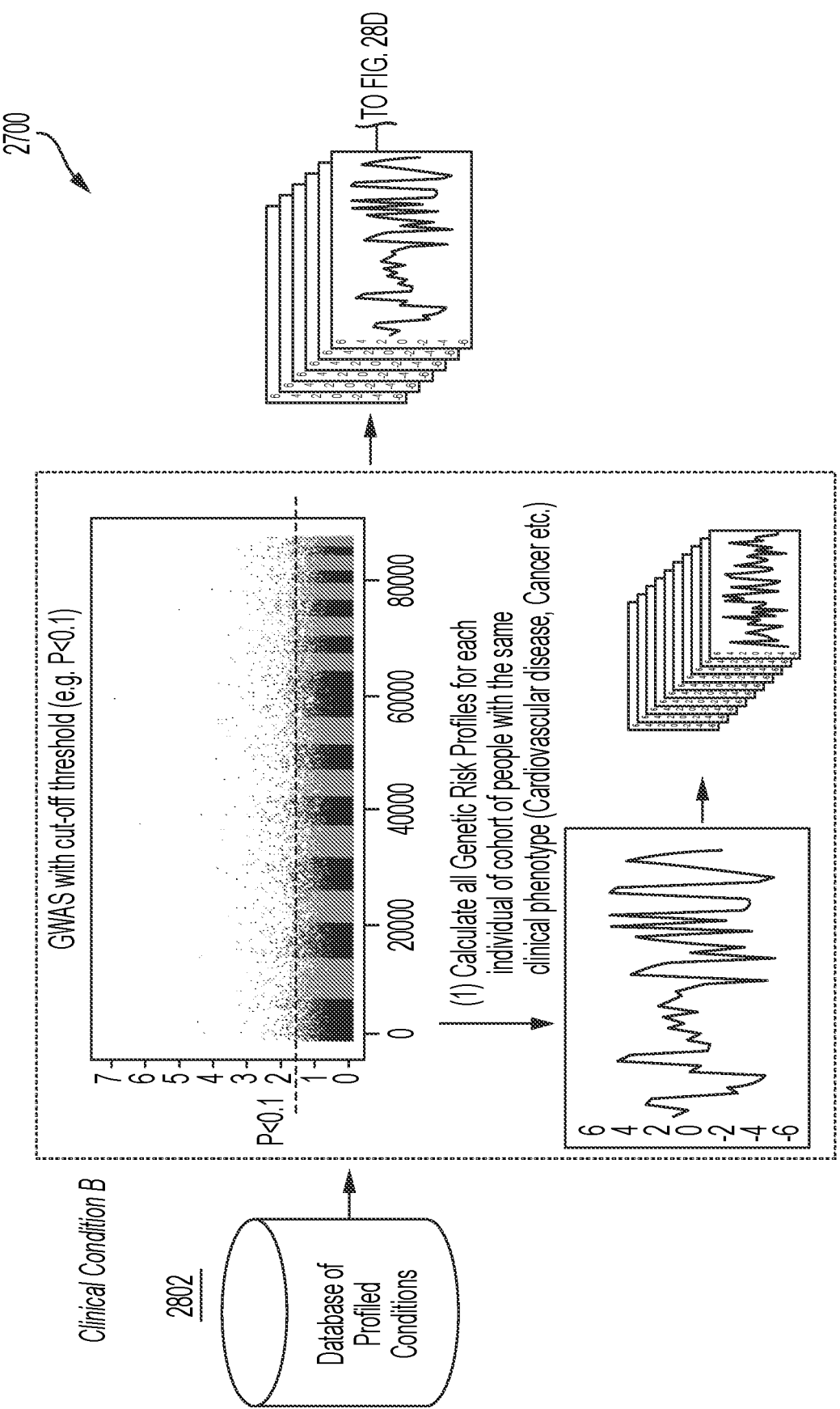
Figure 28D:
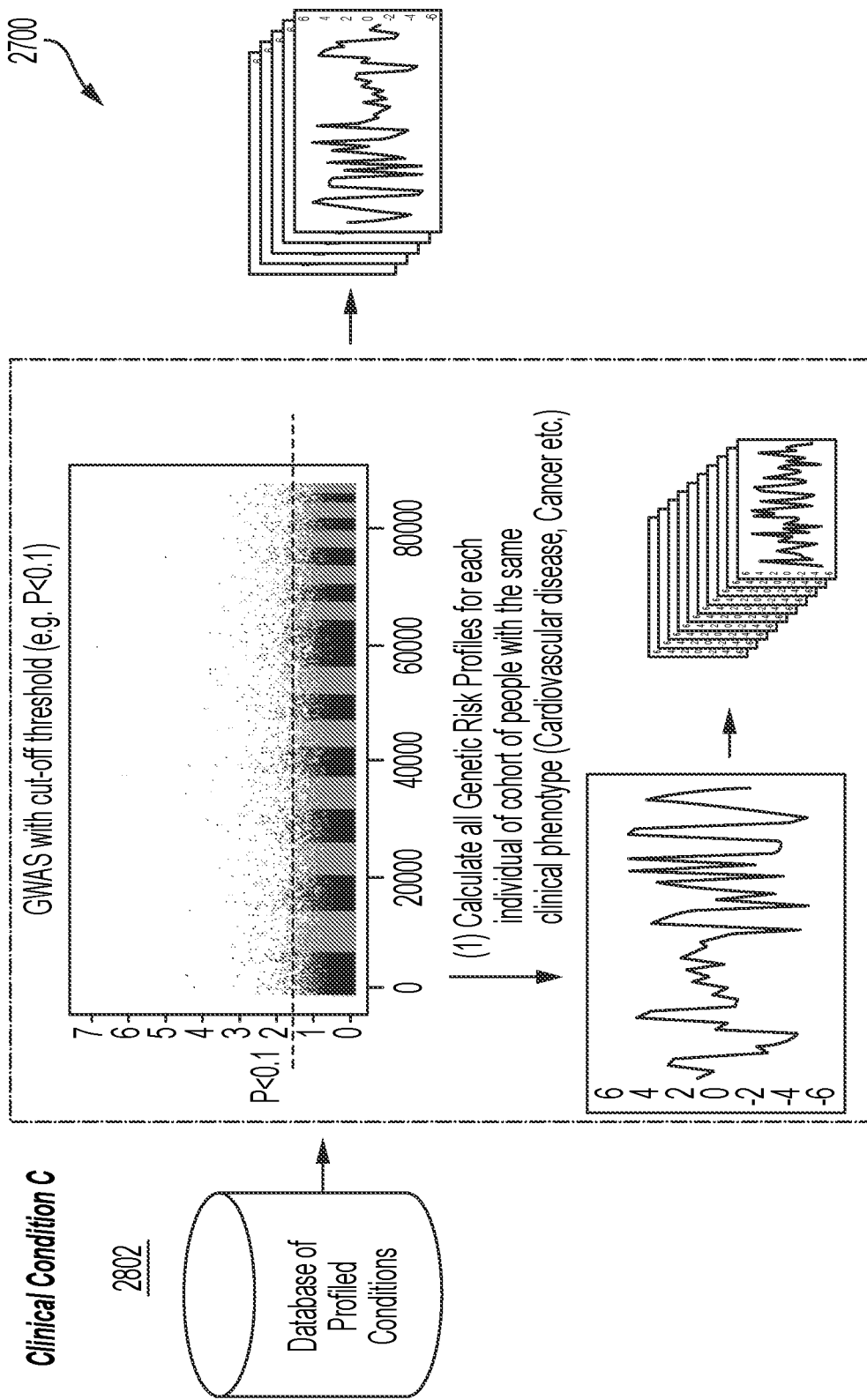

FIG. 27 is a flowchart diagram of an example process for performing cross-condition polygenic diagnosis of an undiagnosed individual in accordance with some embodiments discussed herein.

FIGS. 28A, 28B, 28C, and 28D provide an operational example of an example process for performing cross-condition polygenic predictive inference in accordance with some embodiments discussed herein.

DETAILED DESCRIPTION

Various embodiments of the present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW

Various embodiments of the present invention disclose techniques for performing various polygenic predictive data analysis operations that improve accuracy and reliability of those polygenic predictive data analysis operations, and allows for greater insight and value to be derived from the predictive data analysis results, by utilizing cross-variant polygenic risk modeling data as input to the noted polygenic predictive data analysis operations. The inventors have discovered that various existing polygenic predictive data analysis systems suffer from substantial accuracy and reliability challenges because they map relationships between genetic sequences of particular individuals and target medical conditions across major segments of genetic makeup of the noted individuals, such as across the entirety of genetic sequences of each individual. For example, various existing polygenic predictive data analysis systems utilize polygenic risk score (PRS) measures that typically analyze genetic variation across a large number of single-nucleotide polymorphisms (SNPs) and in doing so lose valuable information about interaction of individual SNPs with target medical conditions if those individual interactions are not statistically powerful enough to have a meaningful effect on the value of a holistic measure such as PRS. By utilizing cross-variant polygenic risk modeling data that independently describe per-genetic-variant correlations between genetic variants of an individual and target medical conditions in order to perform polygenic predictive data analysis, various embodiments of the present invention improve the accuracy and reliability of various existing polygenic predictive data analysis systems, allows for greater insight and value to be derived from the predictive data analysis result, and make important technical contributions to the field of polygenic predictive data analysis.

Furthermore, various embodiments of the present invention disclose techniques for performing various polygenic predictive data analysis operations that improve computational efficiency of those polygenic predictive data analysis operations by inferring contributions of individual genetic variants (e.g., individual SNPs) to occurrence likelihoods of target medical conditions from intermediate outputs of processes that are used to calculate holistic polygenic risk measures such as the PRS measure. For example, various embodiments of the present invention utilize log of odds ratios generated during the PRS generation process in order to generate per-variant genetic risk scores that can in turn be used to generate cross-variant polygenic risk data objects. By inferring per contributions of individual genetic variants to target medical conditions from intermediate outputs of processes that are used to calculate holistic polygenic risk measures, various embodiments of the present invention avoid the need to perform resource-intensive statistical operations in order to generate cross-variant polygenic risk data objects that can in turn be used to perform a variety of cross-variant polygenic data analysis operations. In doing so, various embodiments of the present invention improve the computational efficiency of various existing polygenic predictive data analysis systems and make additional important technical contributions to the field of polygenic predictive data analysis.

Moreover, various embodiments of the present invention disclose techniques for performing various polygenic predictive data analysis operations that improve run-time efficiency of those polygenic predictive data analysis systems by reducing the amount of runtime input needed to perform cross-variant polygenic predictive data analysis. For example, when generating a genetic risk profile and/or a functional genetic risk profile for a particular individual, model definition data generated during training time clarifies the SNPs whose allele counts within the genome of the particular individual should be monitored as well as per-variant genetic risk scores for the noted SNPs. This reduces the need for retrieving and/or generating correlated genetic variant identification data and per-variant genetic risk score data during an ongoing polygenic predictive data analysis inference. Using this technique and related techniques discussed throughout the present document, a polygenic predictive data analysis can reduce the amount of data retrieval and genetic sequence processing operations that needs to be performed during processing of an active request for real-time polygenic predictive data analysis. In doing so, various embodiments of the present invention improve runtime efficiency of various existing polygenic predictive data analysis systems and make further important technical contributions to the field of polygenic predictive data analysis.

While various embodiments discussed in the present document limit the discussion of cross-variant polygenic predictive data analysis operations to one or more of cross-variant polygenic risk modeling operations, per-condition polygenic clustering operations, cross-condition polygenic predictive inference operations, and cross-condition polygenic diagnosis operations, a person of ordinary skill in the relevant technology will recognize that the cross-variant polygenic predictive data analysis concepts discussed herein may be used to infer any health-related conclusion and/or any disease-related conclusion based on genetic makeup of one or more monitored individuals (e.g., genetic sequences of a population of monitored individuals).

II. DEFINITIONS

The term "genetic variant" refers to a data object that describes a variation in human genome. Examples of genetic variants include data objects that describe alleles, SNPs, single-nucleotide variant (SNVs). While various embodiments of the present invention are described with reference to SNPs, a person of ordinary skill in the relevant technology will recognize that the techniques disclosed herein can be used to model polygenic risk and/or perform polygenic prediction across any genetic variant units.

The term "functional grouping" refers to a data object that describes, for one or more genetic variants that are associated with the particular functional grouping, a designation of a common bodily function that the genetic variants affect. For example, a functional grouping may describe the bodily function affected by a group of corresponding SNPs that are associated with the functional grouping. Examples of functional groupings include functional groupings that are configured to classify SNPs based on primary biological pathways that the noted SNPs contribute to, functional groupings that classify SNPs based on protein complexes that the noted SNPs contribute to producing, and/or the like. In some embodiments, the functional groupings maintained by a polygenic predictive data analysis system include a functional grouping of SNPs that affect energy and metabolism operations, a functional grouping of SNPs that affect cell growth operations, a functional grouping of SNPs that affect immune system operations, and a functional grouping of SNPs that affect muscular operations. In some embodiments, assigning a genetic variant to a functional grouping includes assigning the genetic variant to a gene (e.g., the closest gene for the genetic variant and/or the parent gene for the genetic variant) and assigning the gene to a functional grouping.

The term "chromosome grouping" refers to a data object that describes, for a corresponding genetic variant that is associated with the particular chromosome grouping, a designation of the chromosome that the genetic variant is associated with. For example, the chromosome grouping may describe the chromosome that the SNP is part of. Chromosome groupings may be used to classify SNPs based on chromosome associations of the noted SNPs.

The term "per-variant genetic risk score" refers to a data object that describes an estimated level of contribution of a corresponding genetic variant to occurrence of a corresponding target medical condition in a corresponding individual. For example, the per-variant genetic risk score for a corresponding SNP, a corresponding individual, and a corresponding medical condition may describe a likelihood that the corresponding SNP may contribute to likelihood of occurrence of the corresponding medical condition (e.g., occurrence of a particular type of cancer) in the corresponding individual. In some embodiments, the per-variant genetic risk score for a particular SNP is determined based on intermediate output of a PRS generation process. In some embodiments, the per-variant genetic risk score for a particular individual and a particular SNP is determined by combining (e.g., multiplying) the per-variant risk probability value for the particular SNP and the per-variant allele count for the particular SNP with respect to the particular individual.

The term "per-variant risk probability value" refers to a data object that describes an estimated level of contribution of a corresponding genetic variant to occurrence of a corresponding target medical condition across a group of monitored individuals (e.g., a population of individuals some of whom are labeled as suffering from the corresponding target medical condition and others of whom are labeled as not suffering from the corresponding target medical condition). For example, the per-variant risk probability value for a particular SNP may describe an estimated likelihood that existence of the particular SNP in the genome of a particular individual may contribute to occurrence of a particular clinical condition (e.g., to occurrence of a particular type of cancer). In some embodiments, the per-variant risk probability value for a particular SNP is determined based on a log of odds ratio of the particular SNP across a group of individuals with respect to occurrence of a corresponding medical condition. In some embodiments, the per-variant risk probability value for a particular SNP is determined based on p-value of occurrence of the particular SNP with respect to a corresponding target medical condition.

The term "per-variant allele count" refers to a data object that describes a relative frequency of alleles associated with a corresponding genetic variant within genome of a corresponding individual. For example, the per-variant allele count for a particular SNP may describe a relative frequency of alleles that correspond to base choices of the particular SNP within genome of the corresponding individual. In some embodiments, the per-variant allele count of a particular SNP is determined based on the zygosity value of the particular SNP. For example, the per-variant allele count for a particular SNP may describe that the allele associated with the particular SNP is homozygous, heterozygous, hemizygous, or nullizygous.

The term "cross-variant polygenic risk data object" refers to a data object that describes per-variant genetic risk scores of a corresponding set of correlated genetic variants in a corresponding individual and with respect to a corresponding medical condition. For example, a cross-variant polygenic risk data object may describe per-variant genetic risk scores (e.g., log of odds ratios) of a group of SNPs whose computed p-values with respect to a particular type of cancer fall below a p-value threshold, where the per-variant genetic risk scores may be determined based on per-variant genetic risk scores of the group of SNPs across a population of individuals as well as genetic occurrence frequencies of the group of SNPs in a corresponding individual. In some embodiments, at least a portion of a cross-variant polygenic risk data object SNP is determined based on intermediate outputs of a PRS generation process. Examples of cross-variant polygenic risk data objects include genetic risk profiles and functional genetic risk profiles, as further described below.

The term "genetic risk profile" refers to a data object that describes per-variant genetic risk scores associated with a group of genetic variants based on a chromosome-based grouping of the group of genetic variants. For example, the genetic risk profile may describe per-variant genetic risk scores associated with a group of genetic variants whose p-value relative to a target medical condition is below a particular threshold p-value, where the ordering of the per-variant genetic risk scores within the genetic risk profile is determined based on chromosome-based groupings of the genetic variants associated with the genetic risk profile. For example, within a particular genetic risk profile associated with a group of genetic variants that relate to four chromosomes, the per-variant genetic risk scores associated with a first subgroup of the group of genetic variants that relate to a first chromosome of the four chromosomes may be placed in initial locations of the genetic risk profile, followed by the per-variant genetic risk scores associated with a second subgroup of the group of genetic variants that relate to a second chromosome of the four chromosomes, followed by the per-variant genetic risk scores associated with a third subgroup of the group of genetic variants that relate to a third chromosome of the four chromosomes, and followed by the per-variant genetic risk scores associated with a fourth subgroup of the group of genetic variants that relate to a fourth chromosome of the four chromosomes. In some embodiments, the genetic risk profile includes a corresponding array data structure.

The term "functional genetic risk profile" refers to a data object that describes per-variant genetic risk scores associated with a group of genetic variants based on a functional-grouping-based grouping of the group of genetic variants. For example, the functional genetic risk profile may describe per-variant genetic risk scores associated with a group of genetic variants whose p-value relative to a target medical condition is below a particular threshold p-value, where the ordering of the per-variant genetic risk scores within the functional genetic risk profile is determined based on functional-grouping-based groupings of the genetic variants associated with the genetic risk profile. For example, within a particular functional genetic risk profile associated with a group of genetic variants that relate to four functional groupings, the per-variant genetic risk scores associated with a first subgroup of the group of genetic variants that relate to a first functional grouping of the four functional groupings may be placed in initial locations of the genetic risk profile, followed by the per-variant genetic risk scores associated with a second subgroup of the group of genetic variants that relate to a second functional grouping of the four functional groupings, followed by the per-variant genetic risk scores associated with a third subgroup of the group of genetic variants that relate to a third functional grouping of the four functional groupings, and followed by the per-variant genetic risk scores associated with a fourth subgroup of the group of genetic variants that relate to a fourth functional grouping of the four functional groupings. In some embodiments, the functional genetic risk profile for a corresponding target individual includes a corresponding array data structure.

The term "per-chromosome profile segment" refers to a data object that describes a segment of a genetic risk profile that includes per-variant genetic risk scores for a group of genetic variants described by the genetic risk profile, where the noted group of genetic variants all relate to a common chromosome. In some embodiments, each per-chromosome profile segment is associated with a respective chromosome and comprises each per-variant genetic risk score for a genetic variant in a subset of the genetic variants that is associated with the respective chromosome. In some embodiments, when the genetic risk profile is an array data structure, the per-chromosome profile segment is a subarray of the noted array data structure. In some embodiments, when the genetic risk profile is an array data structure and each per-chromosome profile segment is a subarray of the noted array data structure, the genetic risk profile is wholly segmented by one or more per-chromosome profile segments, such that each value in the genetic risk profile belongs to one per-chromone profile segment of the various per-chromosome profile segments and each value in the noted array data structure belongs to one sub-array associated with a per-chromosome profile segment.

The term "per-functional-grouping profile segment" refers to a data object that describes a segment of a functional genetic risk profile that includes per-variant genetic risk scores for a group of genetic variants described by the functional genetic risk profile, where the noted group of genetic variants all relate to a common functional grouping. In some embodiments, each per-functional-grouping profile segment is associated with a respective functional grouping and comprises each per-variant genetic risk score for a genetic variant in a subset of the genetic variants that is associated with the respective functional grouping. In some embodiments, when the functional genetic risk profile is an array data structure, the per-functional-grouping profile segment is a subarray of the noted array data structure. In some embodiments, when the functional genetic risk profile is an array data structure and each per-functional-grouping profile segment is a subarray of the noted array data structure, the genetic risk profile is wholly segmented by one or more per-functional-grouping profile segments, such that each value in the genetic risk profile belongs to one per-functional-grouping profile segment of the various per-functional-grouping profile segments and each value in the noted array data structure belongs to one per-functional-grouping sub-array associated with a per-functional-grouping profile segment.

The term "chromosome-based grouping" refers to a data object that describes, for each genetic variant in a corresponding set of genetic variants, a chromosome designation. In some embodiments, a chromosome-based grouping can be used to generate a corresponding ordering of per-variant genetic risk scores in a genetic risk profile. For example, given a chromosome-based grouping that associates SNPs S1-S4 with chromosome C1, SNPs S4-S8 with chromosome C2, and SNPs S9-S10 with chromosome C3, a computer system may generate the following genetic risk profile: {R1, R2, R3, R4, R5, R6, R7, R8, R9, R10}, where Rn is the per-variant genetic risk score for SNP Sn. As another example, given a chromosome-based grouping that associates SNPs S1-S4 with chromosome C3, SNPs S4-S8 with chromosome C2, and SNPs S9-S10 with chromosome C1, a computer system may generate the following genetic risk profile: {R9, R10, R4, R5, R6, R7, R8, R1, R2, R3}, where Rn is the per-variant genetic risk score for SNP Sn.

The term "functional-grouping-based grouping" refers to a data object that describes, for each genetic variant in a corresponding set of genetic variants, a functional grouping designation. In some embodiments, a functional-grouping-based grouping can be used to generate a corresponding ordering of per-variant genetic risk scores in a functional genetic risk profile. For example, given a functional-grouping-based grouping that associates SNPs S1-S4 with functional grouping F1, SNPs S4-S8 with functional grouping F2, and SNPs S9-S10 with functional grouping F3, a computer system may generate the following functional genetic risk profile: {R1, R2, R3, R4, R5, R6, R7, R8, R9, R10}, where Rn is the per-variant genetic risk score for SNP Sn. As another example, given a chromosome-based grouping that associates SNPs S1-S4 with functional grouping F3, SNPs S4-S8 with chromosome C2, and SNPs S9-S10 with functional grouping F1, a computer system may generate the following functional genetic risk profile: {R9, R10, R4, R5, R6, R7, R8, R1, R2, R3}, where Rn is the per-variant genetic risk score for SNP Sn.

The term "cross-variant polygenic predictive inference" refers to a computer-implemented process configured to process one or more cross-variant polygenic risk data objects to generate one or more desired predictive outputs. Examples of cross-variant polygenic predictive inferences include cross-variant polygenic risk modeling, cross-condition polygenic predictive inference, per-condition polygenic clustering, and cross-condition polygenic diagnosis, all of which are described in greater detail below. In some embodiments, cross-variant polygenic predictive inference includes processing cross-variant polygenic risk data objects using a data analysis model, such as a machine-learning-based data analysis model.

The term "cross-variant polygenic risk modeling" refers to a computer-implemented process configured to process one or more cross-variant polygenic risk data objects for a particular individual and a particular medical condition in order to generate, for each genetic variant in a group of genetic variants, an estimated level of contribution of the genetic variant to occurrence of the particular medical condition in the particular individual. Examples of cross-variant polygenic risk modeling routines are described below. However, a person of ordinary skill in the art will recognize that other data analysis techniques may be utilized to generate estimated levels of contribution of particular genetic variants to occurrence of particular medical conditions in particular individuals.

For example, a cross-variant polygenic risk modeling routine may process a genetic risk profile for a particular individual and a particular medical condition in order to perform smoothing operations across per-chromosome profile segments of the genetic risk profile and subsequently generate a cross-chromosome-smoothed genetic risk profile that includes various cross-chromosome-smoothed per-variant genetic risk scores for each modeled genetic variant. In the noted example, after generating the cross-chromosome-smoothed genetic risk profile, the cross-variant polygenic risk modeling routine may adopt each cross-chromosome-smoothed per-variant genetic risk score described by the cross-chromosome-smoothed genetic risk profile as the estimated level of contribution of a corresponding genetic variant to occurrence of a corresponding medical condition in a corresponding individual.

As another example, a cross-variant polygenic risk modeling routine may process a functional genetic risk profile for a particular individual and a particular medical condition in order to perform smoothing operations across per-functional-grouping profile segments of the functional genetic risk profile and subsequently generate a cross-functional-grouping-smoothed functional genetic risk profile that includes various cross-functional-grouping-smoothed per-variant genetic risk scores for each modeled genetic variant. In the noted example, after generating the cross-functional-grouping-smoothed functional genetic risk profile, the cross-variant polygenic risk modeling routine may adopt each cross-functional-grouping-smoothed per-variant genetic risk score described by the cross-functional-grouping-smoothed functional genetic risk profile as the estimated level of contribution of a corresponding genetic variant to occurrence of a corresponding medical condition in a corresponding individual.

As yet another example, a cross-variant polygenic risk modeling routine may process a genetic risk profile for a particular individual and a particular medical condition in order to perform smoothing operations across per-chromosome profile segments of the genetic risk profile and subsequently generate a cross-chromosome-smoothed genetic risk profile that includes various cross-chromosome-smoothed per-variant genetic risk scores for each modeled genetic variant. In the noted example, subsequent to generating the cross-chromosome-smoothed genetic risk profile, the cross-variant polygenic risk modeling routine may supply the cross-chromosome-smoothed genetic risk profile as an input to a trained convolutional neural network model configured to generate estimated levels of contributions of the corresponding genetic variants to occurrence of a corresponding medical condition in a corresponding individual.

As a further example, a cross-variant polygenic risk modeling routine may process a functional genetic risk profile for a particular individual and a particular medical condition in order to perform smoothing operations across per-functional-grouping profile segments of the functional genetic risk profile and subsequently generate a cross-functional-grouping-smoothed functional genetic risk profile that includes various cross-functional-grouping-smoothed per-variant genetic risk scores for each modeled genetic variant. In the noted example, after generating the cross-functional-grouping-smoothed functional genetic risk profile, the cross-variant polygenic risk modeling routine may supply the cross-functional-grouping-smoothed functional genetic risk profile as an input to a trained convolutional neural network model configured to generate estimated levels of contributions of corresponding genetic variants to occurrence of a corresponding medical condition in a corresponding individual.

The term "cross-condition polygenic predictive inference" refers to a computer-implemented process configured to process one or more primary cross-variant polygenic risk data objects associated with a primary medical condition and one or more secondary cross-variant polygenic risk data objects associated with a secondary medical condition in order to generate one or more predictive inferences based on a cross-condition polygenic similarity measure between the primary medical condition and the secondary medical condition. In some embodiments, predictive outputs generated by cross-condition polygenic predictive inferences include conclusions about likelihood that a treatment regimen (e.g., a drug regimen) of a primary medical condition may be appropriate for a secondary medical condition.

The term "per-condition polygenic clustering" refers to a computer-implemented process that is configured to process cross-variant polygenic risk data objects associated with a group of individuals determined to be associated with a common medical condition in order to generate a clustering of the group of individuals into a group of clusters, where the group of clusters may indicate genetic subtypes of the common medical condition. In some embodiments, per-condition polygenic clustering includes extracting clustering features for each cross-variant polygenic risk data object and/or for each individual, mapping each cross-variant polygenic risk data object and/or each individual to a cross-condition clustering space characterized by the clustering features, and using the cross-condition clustering space to generate conclusions about suitability of using a treatment regimen for a first subset of polygenic risk data objects and/or a first subset of individuals as part of treatment regimens for a second set of polygenic risk data objects and/or a second set of individuals.

Examples of clustering techniques that may be used to cluster a polygenic clustering space include clustering techniques based on connectivity models (e.g., hierarchical clustering), based on centroid models (e.g., using the k-means algorithm), based on distribution models (e.g., using multivariate normal distributions), based on density models, and based on subspace models (e.g., using biclustering). In some embodiments, performing clustering of a polygenic clustering space includes performing a K-means clustering of the noted polygenic clustering space. Other example of clustering algorithms that can be used to cluster a polygenic clustering space include K-medoids clustering, hierarchical clustering, K-Nearest-Neighbor clustering, and/or the like.

The term "cross-condition polygenic diagnosis" refers to a computer-implemented process that is configured to process diagnosed cross-variant polygenic risk data objects associated with a diagnosed group of individuals and undiagnosed cross-variant polygenic risk data objects associated with an undiagnosed individual in order to perform a diagnosis of an undiagnosed medical condition of the undiagnosed individual. Examples of cross-condition polygenic diagnosis routines are described below. However, a person of ordinary skill in the relevant technology will recognize that any data analysis technique can be utilized to generate polygenic similarity measures across diagnosed cross-variant polygenic risk data objects and undiagnosed cross-variant polygenic risk data objects, where the generated polygenic similarity measures can be used to determine diagnostic conclusions for the undiagnosed cross-variant polygenic risk data objects.

The term "chromosome-based predictive output interface" refers to a data object that describes a user interface configured to display data that is determined based on a genetic risk profile. For example, a chromosome-based predictive output interface may be configured to display a chromosome-grouped predictive output graph that depicts per-variant genetic risk scores (e.g., cross-chromosome-smoothed per-variant genetic risk scores) for a group of genetic variants with respect to a particular individual and a particular medical condition, where the per-variant genetic risk scores are grouped based on chromosome-based groupings of genetic variants associated with those per-variant genetic risk scores.

The term "chromosome-based predictive output graph" refers to a data object that describes per-variant genetic risk scores (e.g., cross-chromosome-smoothed per-variant genetic risk scores) for a group of genetic variants with respect to a particular individual and a particular medical condition, where the per-variant genetic risk scores are grouped based on chromosome-based groupings of genetic variants associated with those per-variant genetic risk scores. In some embodiments, a first coordinate (e.g., a horizontal coordinate) of the chromosome-grouped predictive output graph comprises descriptions of the genetic variants associated with the chromosome-grouped predictive output graph in accordance with chromosome-based groupings of the genetic variants, while a second coordinate (e.g., a vertical coordinate) of the chromosome-grouped predictive output graph comprises a range of per-variant genetic risk scores (e.g., cross-chromosome-smoothed per-variant genetic risk scores) for the genetic variants.

The term "functional-grouping-based predictive output interface" refers to a data object that describes a user interface configured to display data that is determined based on a functional genetic risk profile. For example, a functional-grouping-based predictive output interface may be configured to display a functional-grouping-grouped predictive output graph that depicts per-variant genetic risk scores (e.g., cross-chromosome-smoothed per-variant genetic risk scores) for a group of genetic variants with respect to a particular individual and a particular medical condition, where the per-variant genetic risk scores are grouped based on functional-grouping-based groupings of genetic variants associated with those per-variant genetic risk scores.

The term "functional-grouping-based predictive output graph" refers to a data object that describes per-variant genetic risk scores (e.g., cross-chromosome-smoothed per-variant genetic risk scores) for a group of genetic variants with respect to a particular individual and a particular medical condition, where the per-variant genetic risk scores are grouped based on functional-grouping-based groupings of genetic variants associated with those per-variant genetic risk scores. In some embodiments, a first coordinate (e.g., a horizontal coordinate) of the chromosome-grouped predictive output graph comprises descriptions of the genetic variants associated with the chromosome-grouped predictive output graph in accordance with functional-grouping-based groupings of the genetic variants, while a second coordinate (e.g., a vertical coordinate) of the chromosome-grouped predictive output graph comprises a range of per-variant genetic risk scores (e.g., cross-chromosome-smoothed per-variant genetic risk scores) for the genetic variants.

The term "training genetic sequence" refers to a data object that describes a genetic sequence of an individual, where the genetic sequence is configured to be utilized in order to generate a trained machine learning model. For example, a group of trained genetic sequences may describe genetic sequences that are configured to be utilized to train a machine learning model that is configured to generate a per-variant risk probability value for at least some of the genetic variants that are present in a group of training genetic sequences.

The term "training observational label" refers to a data object that describes a ground-truth label (e.g., a ground-truth medical condition) of a corresponding training genetic sequence. For example, a training observational label that is associated with a corresponding training genetic sequence may describe a ground-truth medical condition of an individual associated with the corresponding training genetic sequence. Training observational labels can be used along with training genetic sequences in order to generate a trained machine learning model, such as a machine learning that is configured to generate a per-variant risk probability value for each genetic variant that is present in at least one of the training genetic sequences.

The term "candidate genetic variant" refers to a data object that describes a genetic variant that is present in at least one of the training genetic sequences used to generate a trained machine learning model. In some embodiments, training a machine learning model to perform cross-variant polygenic risk modeling includes selecting a subset of candidate genetic variants to integrate as a correlated genetic variant into the trained machine learning model, where the selection may be performed based on probability values that describe estimated contributions of the candidate genetic variants to a particular medical condition. For example, in some embodiments, the genetic variants used to perform polygenic risk modeling are selected based on a subset of the candidate genetic variants whose p-values with respect to a particular medical condition falls below a particular p-value threshold.

The term "testing genetic sequence" refers to a data object that describes a genetic sequence of an individual, where the genetic sequence is configured to be utilized in order to generate an accuracy level of a trained machine learning model. For example, a group of trained genetic sequences may describe genetic sequences that are configured to be utilized to test an accuracy level of a machine learning that is configured to generate a per-variant risk probability value for at least some of the genetic variants that are present in a group of training genetic sequences.

The term "testing observational label" refers to a data object that describes a ground-truth label (e.g., a ground-truth medical condition) of a corresponding testing genetic sequence. For example, a testing observational label that is associated with a corresponding testing genetic sequence may describe a ground-truth medical condition of an individual associated with the corresponding testing genetic sequence. Testing observational labels can be used along with training genetic sequences in order to test an accuracy level of a trained machine learning model, such as a machine learning that is configured to generate a per-variant risk probability value for at least some of the genetic variants that are present in a group of training genetic sequences.

The term "validation determination" refers to a data object that describes whether a corresponding trained machine learning model has successfully demonstrated a desired level of accuracy during a corresponding testing process. For example, given a trained machine learning model that includes a set of per-variant genetic risk scores for a set of genetic variants, a testing process may determine a testing prediction for each individual in a group of individuals associated with a group of testing genetic sequences by applying the set of per-variant genetic risk scores to the testing genetic sequence for the individual. In the noted example, the testing process may compare the generated set of testing predictions to corresponding testing observational labels and determine an accuracy level for the trained machine learning model. Thereafter, the testing process may determine the validation determination for the trained machine learning model based on the determined accuracy level. For example, the testing process may determine the validation determination for the trained machine learning model based on whether the determined accuracy level exceeds an accuracy level threshold, where the accuracy level threshold may be determined based on a preconfigured value, a run-time-generated value, and/or a value determined based on a trained parameter and/or a trained hyper-parameter of the testing process.

The term "static genetic variant" refers to a data object that describes a genetic variant that is determined to be correlated with a corresponding target medical condition based on preexisting subject matter domain data and is accordingly included among the set of genetic variants used to perform polygenic genetic risk modeling. Examples of preexisting subject matter domain data include data describing medical research conclusions about correlation of genetic variants with target medical conditions.

The term "dynamic genetic variant" refers to a data object that describe a genetic variant that is determined to be correlated with a corresponding target medical condition based on results of an automated statistical analysis about correlation of a group of candidate genetic variants and a corresponding target medical condition. For example, in some embodiments, dynamic genetic variants may include genetic variants whose p-values with respect to a target medical condition is below a p-value threshold.

The term "clustering feature" refers to a data object that describes a particular feature type for cross-polygenic risk data objects, where the particular feature type characterizes at least one dimension of a polygenic clustering space. Accordingly, a clustering feature may describe a feature that can be utilized to cluster cross-polygenic risk data objects and/or cluster individuals that are associated with cross-polygenic risk data objects. Examples of clustering features are features that are determined based on modeled genetic variants for a set of cross-variant polygenic risk data objects. For example, a first clustering feature may describe the per-variant genetic risk score of a corresponding cross-variant polygenic risk data object with respect to a first modeled genetic variant associated with the corresponding cross-variant polygenic risk data object. As another example, a first clustering feature may describe the per-variant genetic risk score of a corresponding cross-variant polygenic risk data object with respect to two or more modeled genetic variants associated with the corresponding cross-variant polygenic risk data object.

In some embodiments, given a set of cross-variant polygenic risk data objects, feature extraction and generation of a corresponding clustering space is performed based on a set of clustering features that include a per-variant genetic risk score feature type for each genetic variant in a selected subset of genetic variants mapped by the set of cross-variant polygenic risk data objects. For example, the set of clustering features may include a union of a per-variant genetic risk score feature type for each genetic variant in a subset of genetic variants mapped by the set of cross-variant polygenic risk data objects that includes all of those genetic variants. As another example, the set of clustering features may include an intersection of a per-variant genetic risk score feature type for each genetic variant in a subset of genetic variants mapped by the set of cross-variant polygenic risk data objects that includes all of those genetic variants. As yet another example, the set of clustering features may be generated by performing dimensionality reduction (e.g., principal component analysis) on a set of features that include a union of a per-variant genetic risk score feature type for each genetic variant in a subset of genetic variants mapped by the set of cross-variant polygenic risk data objects that includes all of those genetic variants. As a further example, the set of clustering features may be generated by performing dimensionality reduction (e.g., principal component analysis) on a set of features that include an intersection of a per-variant genetic risk score feature type for each genetic variant in a subset of genetic variants mapped by the set of cross-variant polygenic risk data objects that includes all of those genetic variants.

In some embodiments, given a set of cross-variant polygenic risk data objects, feature extraction and generation of a corresponding clustering space is performed by providing the set of cross-variant polygenic risk data objects to a trained feature extraction model configured to generate clustering features based on the set of cross-variant polygenic risk data objects. For example, each cross-variant polygenic risk data object may be turned into a graph image and provided as an input to a trained convolutional neural network model configured to generate clustering features based on the input graph images. As another example, each cross-variant polygenic risk data object may be turned into a graph image and provided as an input to a trained autoencoder model configured to generate low-dimensional representations of the graph images and process the low-dimensional representations in order to generate clustering features for each graph image.

The term "intersectional variant set" of two or more sets of genetic variants may refer to a data object that describes a set of genetic variants that are in each of the two or more sets of genetic variants. For example, an intersectional variant set of two or more genetic risk profiles may include SNPs that are modeled by each of the two or more genetic risk profiles. As another example, an intersectional variant set of two or more functional genetic risk profiles may include SNPs that are modeled by each of the two or more functional genetic risk profiles. In some embodiments, clustering features for a per-condition polygenic clustering process are determined based on an intersectional variant set of each set of modeled genetic variants for a cross-variant polygenic risk data object of a plurality of cross-variant polygenic risk data objects.

The term "union variant set" of two or more sets of genetic variants may refer to a data object that describes a set of genetic variants that are in at least one of the two or more sets of genetic variants. For example, a union variant set of two or more genetic risk profiles may include SNPs that are modeled by at least one of the two or more genetic risk profiles. As another example, a union variant set of two or more functional genetic risk profiles may include SNPs that are modeled by at least one of the two or more functional genetic risk profiles. In some embodiments, clustering features for a per-condition polygenic clustering process are determined based on a union variant set of each set of modeled genetic variants for a cross-variant polygenic risk data object of a plurality of cross-variant polygenic risk data objects.

The term "per-object feature value" refers to a data object that describes a latest value for a corresponding clustering feature. For example, if a clustering feature is characterized by per-variant genetic risk score for a particular SNP in a particular individual with respect to a particular medical condition, the per-object feature value for the noted clustering feature may describe a latest value of the per-variant genetic risk score for the particular SNP. As another example, if a clustering feature is characterized by per-variant genetic risk score for two or more particular SNPs in a particular individual with respect to a particular medical condition, the per-object feature value for the noted clustering feature may describe a latest value of a measure of statistical distribution (e.g., an average, a weighted average, a median, and/or the like) of the two or more per-variant genetic risk score for the particular two or more SNPs.

The term "polygenic clustering space" refers to a data object that describes, for each cross-variant polygenic risk data object mapped by the polygenic clustering space, a per-object feature value for the cross-variant polygenic risk data object. In some embodiments, the polygenic clustering space is a n-dimensional space, where n is the number of clustering features associated with the polygenic clustering space. In some embodiments, the polygenic clustering space is generated by performing dimensionality reduction on a raw multi-dimensional space characterized by per-SNP dimensions, where each of the per-SNP dimensions of the polygenic clustering space describes the per-SNP genetic risk score for a corresponding SNP associated with the per-SNP dimension. While various embodiments of the present invention describe polygenic clustering spaces that are used to map cross-variant polygenic risk data objects, a person of ordinary skill in the art will recognize that polygenic clustering spaces can be used to map individuals. Indeed, in some embodiments, if the same individual is associated with two or more cross-variant polygenic risk data objects (e.g., a genetic risk profile and a functional genetic risk profile), the per-object features of the two or more cross-variant polygenic risk data objects will be aggregated to generate a single per-individual feature for the corresponding individual.

The term "inferred sub-condition" for a target medical condition refers to a data object that describes one or more genetic features of a proper subset of individuals affected by the target medical condition. The inferred sub-conditions for a target medical condition may be determined by mapping genetic data of individuals associated with the target medical condition onto a polygenic clustering space and using the polygenic clustering space to cluster the mapped genetic data into subsets.

The term "cross-condition polygenic similarity measure" refers to a data object that describes a similarity measure and/or a distance measure for two or more medical conditions and/or for two or more individuals affected by two or more medical conditions based on comparing cross-variant polygenic risk data objects associated with the two or more medical conditions and/or the two or more individuals. For example, a cross-condition polygenic similarity measure for two medical conditions may be determined based on comparing a measure of distribution (e.g., an average) of per-variant genetic risk scores described by genetic risk profiles of individuals affected by the first medical condition and a measure of distribution of per-variant genetic risk scores described by genetic risk profiles of individuals affected by the second medical condition. As another example, a cross-condition polygenic similarity measure for two medical conditions may be determined based on comparing a measure of distribution (e.g., an average) of per-variant genetic risk scores described by functional genetic risk profiles of individuals affected by the first medical condition and a measure of distribution of per-variant genetic risk scores described by functional genetic risk profiles of individuals affected by the second medical condition.

The term "pairwise similarity measure" refers to a data object that describes a measure of similarity and/or a measure of distance of two corresponding cross-variant polygenic risk data objects. For example, a pairwise similarity measure may describe a measure of similarity of two genetic risk profiles. As another example, a pairwise similarity measure may describe a measure of similarity of two functional genetic risk profiles. As yet another example, a pairwise similarity measure may describe a measure of similarity of a genetic risk profile and a functional genetic risk profile.

The term "intersectional variant count" of two or more cross-variant polygenic risk data objects is a data object that describes a cardinality of the set of genetic variants that is modeled by all of the two or more cross-variant polygenic data objects. For example, the intersectional variant count of the primary cross-variant polygenic risk data object in an object pair and the secondary cross-variant polygenic risk data object in the object pair describes a cardinality of genetic variants that are modeled by both the primary cross-variant polygenic risk data object and the secondary cross-variant polygenic risk data object.

The term "maximal variant count" of two or more cross-variant polygenic risk data objects refers to a data object that describes a cardinality of the set of genetic variants that is modeled by a cross-variant polygenic data object of the two or more cross-variant polygenic data objects that has the highest number of modeled genetic variants relative to the other cross-variant polygenic data objects in the two or more cross-variant polygenic data objects. For example, if a primary cross-variant polygenic risk data object in an object pair is associated with m genetic variants and a secondary cross-variant polygenic risk data object in the object pair is associated with n genetic variants, and further if m>n, the maximal variant count of the primary cross-variant polygenic risk data object in the object pair and the secondary cross-variant polygenic risk data object in the object pair describes a cardinality of genetic variants that are modeled by the primary cross-variant polygenic risk data object (i.e., a cardinality of m).

The term "union variant count" of two or more cross-variant polygenic risk data objects is a data object that describes a cardinality of the set of genetic variants that is modeled by at least one of the two or more cross-variant polygenic data objects. For example, the union variant count of the primary cross-variant polygenic risk data object in an object pair and the secondary cross-variant polygenic risk data object in the object pair describes a cardinality of genetic variants that are modeled by at least one of the primary cross-variant polygenic risk data object and the secondary cross-variant polygenic risk data object.

The term "minimal variant count" of two or more cross-variant polygenic risk data objects refers to a data object that describes a cardinality of the set of genetic variants that is modeled by a cross-variant polygenic data object of the two or more cross-variant polygenic data objects that has the lowest number of modeled genetic variants relative to the other cross-variant polygenic data objects in the two or more cross-variant polygenic data objects. For example, if a primary cross-variant polygenic risk data object in an object pair is associated with m genetic variants and a secondary cross-variant polygenic risk data object in the object pair is associated with n genetic variants, and further if m<n, the minimal variant count of the primary cross-variant polygenic risk data object in the object pair and the secondary cross-variant polygenic risk data object in the object pair describes a cardinality of genetic variants that are modeled by the primary cross-variant polygenic risk data object (i.e., a cardinality of m).

The term "per-variant pairwise polygenic similarity measure" refers to a data object that describes a similarity measure of per-variant genetic risk data scores for two cross-variant polygenic risk data objects with respect to a corresponding genetic variant associated with the per-variant pairwise polygenic similarity measure. For example, a per-variant pairwise polygenic similarity measure may describe a similarity of the per-variant genetic risk data score for a particular genetic variant as indicated by a first genetic risk profile and the per-variant genetic risk data score for the particular genetic variant as indicated by a second genetic risk profile. As another example, a per-variant pairwise polygenic similarity measure may describe a similarity of the per-variant genetic risk data score for a particular genetic variant as indicated by a first functional genetic risk profile and the per-variant genetic risk data score for the particular genetic variant as indicated by a second functional genetic risk profile. As yet another example, a per-variant pairwise polygenic similarity measure may describe a similarity of the per-variant genetic risk data score for a particular genetic variant as indicated by a genetic risk profile and the per-variant genetic risk data score for the particular genetic variant as indicated by a functional genetic risk profile.

The term "undiagnosed cross-variant polygenic risk data object" refers to a cross-variant polygenic risk data object that includes per-variant genetic risk scores for a target medical condition that has not been diagnosed with a requisite level of certainty. For example, an undiagnosed cross-variant polygenic risk data object may include a genetic risk profile related to a target medical condition that lacks any diagnostic labels. As another example, an undiagnosed cross-variant polygenic risk data object may include a genetic risk profile related to a target medical condition that has diagnostic labels, but where estimated degrees of certainty in the noted diagnostic labels falls below a certainty threshold. As yet another example, an undiagnosed cross-variant polygenic risk data object may include a functional genetic risk profile related to a target medical condition that lacks any diagnostic labels. As a further example, an undiagnosed cross-variant polygenic risk data object may include a functional genetic risk profile related to a target medical condition that has diagnostic labels, but where estimated degrees of certainty in the noted diagnostic labels falls below a certainty threshold.

The term "diagnosed cross-variant polygenic risk data object" refers to a cross-variant polygenic risk data object that includes per-variant genetic risk scores for a target medical condition that has been diagnosed with a requisite level of certainty. For example, a diagnosed cross-variant polygenic risk data object may include a genetic risk profile related to a target medical condition that has diagnostic labels, where estimated degrees of certainty in the noted diagnostic labels satisfy a certainty threshold. As another example, a diagnosed cross-variant polygenic risk data object may include a functional genetic risk profile related to a target medical condition that has diagnostic labels, where estimated degrees of certainty in the noted diagnostic labels satisfy a certainty threshold.

The term "inferred diagnosis" refers to a data object that describes one or more estimated medical conditions for an undiagnosed individual based on a cross-variant polygenic analysis of one or more cross-variant polygenic data objects associated with the undiagnosed individual and one or more cross-variant polygenic data objects associated with one or more diagnosed individuals. In some embodiments, the inferred diagnosis may describe two or more estimated medical conditions for an undiagnosed individual. In some embodiments, the inferred diagnosis may further describe a diagnosis probability value for each estimated medical condition described by the inferred diagnosis for the undiagnosed individual.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language, such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatuses, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing cross-variant polygenic predictive data analysis. The architecture 100 includes a cross-variant polygenic predictive data analysis system 101 configured to receive predictive data analysis requests from the client computing entities 102, process the predictive data analysis requests to generate data analysis outputs, provide the generated predictive data analysis outputs to the client computing entities 102 in response to the predictive data analysis requests, and perform prediction-based actions based on the generated predictive data analysis outputs.

In some embodiments, cross-variant polygenic predictive data analysis system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), and/or the like, as well as any hardware, software and/or firmware required to implement it (such as, e.g., network routers, and/or the like).

The cross-variant polygenic predictive data analysis system 101 may include a cross-variant polygenic predictive data analysis computing entity 106 and a storage subsystem 108. The cross-variant polygenic predictive data analysis computing entity 106 may be configured to perform a variety of cross-variant polygenic predictive data analysis operations, such as cross-variant polygenic risk modeling operations, per-condition polygenic clustering operations, cross-condition polygenic predictive inference operations, and cross-condition polygenic diagnosis operations.

The cross-variant polygenic predictive data analysis computing entity 106 may include a cross-variant risk modeling engine 111, a polygenic clustering engine 112, a cross-condition inference engine 113, and a cross-condition diagnosis engine 114. Aspects of the functions of the cross-variant risk modeling engine 111, the polygenic clustering engine 112, the cross-condition inference engine 113, and the cross-condition diagnosis engine are discussed below with reference to FIGS. 4-28.

The storage subsystem 108 may be configured to store at least a portion of input data (e.g., training genetic sequence data, training observational label data, testing genetic sequence data, testing observational label data, and/or the like) utilized by the cross-variant polygenic predictive data analysis computing entity 106 to generate a trained and tested polygenic machine learning model that is used to generate cross-variant polygenic risk data objects. The storage subsystem 108 may further be configured to store at least a portion of configuration data (e.g., model definition data) utilized by the cross-variant polygenic predictive data analysis computing entity 106 to perform a variety of cross-variant polygenic predictive data analysis operations, such as cross-variant polygenic risk modeling operations, per-condition polygenic clustering operations, cross-condition polygenic predictive inference operations, and cross-condition polygenic diagnosis operations.

The storage subsystem 108 may include one or more storage units, such as multiple distributed storage units that are connected through a computer network. Each storage unit in the storage subsystem 108 may store at least one of one or more data assets and/or one or more data objects about the computed properties of one or more data assets. Moreover, each storage unit in the storage subsystem 108 may include one or more non-volatile storage or memory media, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Cross-Variant Polygenic Predictive Data Analysis Computing Entity

FIG. 2 provides a schematic of a cross-variant polygenic predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the cross-variant polygenic predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the cross-variant polygenic predictive data analysis computing entity 106 may include or be in communication with one or more processing elements 205 (also referred to as processors, processing circuitry, and/or similar terms used herein interchangeably) that communicate with other elements within the cross-variant polygenic predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the cross-variant polygenic predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the cross-variant polygenic predictive data analysis computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the cross-variant polygenic predictive data analysis computing entity 106 with the assistance of the processing element 205 and operating system.

As indicated, in one embodiment, the cross-variant polygenic predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the cross-variant polygenic predictive data analysis computing entity 106 may be configured to communicate via wireless client communication networks using any of a variety of protocols, such as general packet radio service (GRPS), Universal Mobile Telecommunications System (UMTS), Code Division Multiple Access 1900 (CDMA1900), CDMA1900 1x (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the cross-variant polygenic predictive data analysis computing entity 106 may include or be in communication with one or more input elements, such as a keyboard input, a mouse input, a touch screen/display input, motion input, movement input, audio input, pointing device input, joystick input, keypad input, and/or the like. The cross-variant polygenic predictive data analysis computing entity 106 may also include or be in communication with one or more output elements (not shown), such as audio output, video output, screen/display output, motion output, movement output, and/or the like.

Exemplary Client Computing Entity

FIG. 3 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the cross-variant polygenic predictive data analysis computing entity 106. In a particular embodiment, the client computing entity 102 may operate in accordance with multiple wireless communication standards and protocols, such as UMTS, CDMA1900, 1xRTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the cross-variant polygenic predictive data analysis computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the cross-variant polygenic predictive data analysis computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the cross-variant polygenic predictive data analysis computing entity 106 and/or various other computing entities.

In another embodiment, the client computing entity 102 may include one or more components or functionality that are the same or similar to those of the cross-variant polygenic predictive data analysis computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

FIG. 4 is a flowchart diagram of an example process 400 for performing cross-variant polygenic predictive data analysis. Via the various steps/operations of the process 400, the cross-variant polygenic predictive data analysis computing entity 106 can efficiently and effectively perform cross-variant polygenic predictive data analyses using cross-variant polygenic risk data objects (e.g., genetic risk profiles, functional genetic risk profiles, and/or the like) that are determined using intermediate outputs of a PRS generation process, which in turn eliminates the need for performing resource-intensive statistical operations in order to perform cross-variant polygenic predictive data analysis operations.

The process 400 begins when the cross-variant risk modeling engine 111 generates cross-variant polygenic risk data objects 121 and provides the cross-variant polygenic risk data objects 121 to the polygenic clustering engine 112, the cross-condition inference engine 113, and the cross-condition diagnosis engine 114. Examples of cross-variant polygenic risk data objects 121 include genetic risk profiles and functional genetic risk profiles. Aspects of genetic risk profiles are described in greater detail below with reference to Subsection A of the present section. Aspects of functional genetic risk profiles are described in greater detail below with reference to Subsection B of the present section.

The polygenic clustering engine 112 is configured to perform per-condition polygenic clustering based on the cross-variant polygenic risk data objects 121 associated with a common medical condition in order to detect sub-conditions associated with the common medical condition. Aspects of per-condition polygenic clustering operations are described in greater detail below with reference to Subsection C of the present section.

The cross-condition inference engine 113 is configured to perform cross-condition polygenic predictive inference based on cross-variant polygenic risk data objects 121 associated with each of two or more medical conditions in order to detect opportunities for repurposing treatment regimen of a first subset of the two or more medical conditions in order to address medical needs of a second subset of the two or more medical conditions. Aspects of cross-condition polygenic predictive inference operations are described in greater below with reference to Subsection D of the present section.

The cross-condition diagnosis engine 114 is configured to perform cross-condition polygenic diagnosis based on a set of cross-variant polygenic risk data objects 121 associated with a group of undiagnosed individuals and a set of cross-variant polygenic risk data objects 121 associated with a group of diagnosed individuals in order to generate diagnostic conclusions for the group of undiagnosed individuals. Aspects of cross-condition polygenic diagnosis operations are discussed in greater detail below with reference to Subsection E of the present section.

A. Cross-Variant Polygenic Risk Modeling Using Genetic Risk Profiles

FIG. 5 is a flowchart diagram of an example process 500 for generating a genetic risk profile for a target individual with respect to a target medical condition. Via the various steps/operations of the process 500, the cross-variant risk modeling engine 111 of the cross-variant polygenic predictive data analysis computing entity 106 can efficiently and reliably generate genetic risk profiles by using intermediate outputs of a PRS generation process, which eliminates the need for performing resource-intensive statistical operations in order to generate genetic risk profiles.

The process 500 begins at step/operation 501 when the cross-variant risk modeling engine 111 generates a per-variant genetic risk score for each genetic variant of a plurality of modeled genetic variants that relate to the genetic risk profile. In some embodiments, to generate the per-variant genetic risk score for each genetic variant of a plurality of modeled genetic variants for the genetic risk profile, the cross-variant risk modeling engine 111 generates a trained polygenic machine learning model associated with a corresponding target medical condition, where the trained polygenic machine learning model is configured to identify: (i) one or more correlated genetic variants, and (ii) for each genetic variant of the one or more correlated genetic variants, a per-variant risk score. Thereafter, the cross-variant risk modeling engine 111 uses the per-variant risk scores identified by the trained polygenic machine learning model in order to generate each per-variant genetic risk score for a genetic variant among the one or more correlated genetic variants.

In some embodiments, step/operation 501 may be performed in accordance with the process depicted in FIG. 6. The process depicted in FIG. 6 begins at step/operation 601 when the cross-variant risk modeling engine 111 generates the trained polygenic machine learning model. In some embodiments, generating the trained polygenic machine learning model includes generating the trained polygenic machine learning model and testing the trained polygenic machine learning model to ensure that the trained polygenic machine learning model exhibits a desired prediction accuracy level when analyzed in accordance with test data.

In some embodiments, step/operation 601 may be performed in accordance with the process depicted in FIG. 7. The process depicted in FIG. 7 begins at step/operation 701 when the cross-variant risk modeling engine 111 identifies a group of training genetic sequences associated with a first group of individuals. In some embodiments, a training genetic sequence is a genetic sequence of a corresponding individual in the first group of individuals that is configured to be utilized in order to generate a trained polygenic machine learning model.

In some embodiments, to identify the group of training genetic sequences, the cross-variant risk modeling engine 111 may divide a group of labeled genetic sequences for a group of individuals into two subgroups: a training subgroup that includes labeled genetic sequences configured to be used to generate the trained polygenic machine learning model and a testing subgroup that includes labeled genetic sequences configured to be used to test the trained polygenic machine learning model. In some embodiments, the cross-variant risk modeling engine 111 may divide the group of labeled genetic sequences into the training subgroup and the testing subgroup in accordance with a division ratio value that describes a ratio of the labeled genetic sequences that will be used for generating the trained polygenic machine learning model. In some embodiments, the division ratio value may be determined based on a preconfigured value, a run-time-generated value, and/or a value determined based on a trained parameter and/or a trained hyper-parameter of the training process.

In some embodiments, a training genetic sequence of a corresponding individual includes genetic variants present in the genome of the corresponding individual. In some embodiments, a genetic variant is a data object that describes a variation in human genome (e.g., a unit-level variation in human genome, such as a nucleobase-level variation). Examples of genetic variants include data objects that describe alleles, SNPs, SNVs, and/or the like. While various embodiments of the present invention are described with reference to SNPs, a person of ordinary skill in the relevant technology will recognize that the disclosed techniques can be used to model polygenic risk and/or perform polygenic prediction across any genetic variant units.

At step/operation 702, the cross-variant risk modeling engine 111 identifies a group of training observational labels including a training observational label for each training genetic sequence of the group of training genetic sequences. In some embodiments, a training observational label is a data object that describes a ground-truth label (e.g., a ground-truth medical condition) of a corresponding training genetic sequence. In some embodiments, a training observational label that is associated with a corresponding training genetic sequence may describe a ground-truth medical condition of an individual associated with the corresponding training genetic sequence. For example, a training observational label for a corresponding training genetic sequence may describe whether an individual associated with the corresponding training genetic sequence suffers from a corresponding target medical condition. As another example, a training observational label for a corresponding training genetic sequence may describe a level of severity of a corresponding target medical condition in an individual associated with the corresponding training genetic sequence.

At step/operation 703, the cross-variant risk modeling engine 111 determines a group of candidate genetic variants based on the training genetic sequences. A candidate genetic variant may be a genetic variant that may be included among the modeled genetic variants for the genetic risk profile if an estimated level of correlation of the candidate genetic variant with the target medical condition exceeds a threshold value. The group of candidate genetic variants may be determined based on at least a subset of the genetic variants present in the group of genetic training sequences. The group of candidate genetic variants may further include a group of genetic variants described as potentially being correlated with the target medical condition based on subject matter domain data, such as based on data describing medical research on the genetic contributions to the target medical condition.

At step/operation 704, the cross-variant risk modeling engine 111 determines, for each candidate genetic variant in the group of candidate genetic variants, a p-value with respect to the target medical condition based on the group of training genetic sequences and the group of training observational labels. In some embodiments, to generate the p-values for the group of candidate genetic variants, the cross-variant risk modeling engine 111 processes the group of genetic training sequences and the group of training observational labels (e.g., the group of discrete observational labels) to generate a distribution of positive training observational labels across the group of candidate genetic variants. The cross-variant risk modeling engine 111 may then process the generated distribution to determine a p-value for each genetic variant in the group of genetic variants.

In some embodiments, to generate the p-values for the group of candidate genetic variants, the cross-variant risk modeling engine 111 processes the group of genetic training sequences and the group of training observational labels (e.g., the group of discrete observational labels) to generate a distribution of above-threshold training observational labels across the group of candidate genetic variants. The cross-variant risk modeling engine 111 may then process the generated distribution to determine a p-value for each genetic variant in the group of genetic variants.

In some embodiments, to generate the p-values for the group of candidate genetic variants, the cross-variant risk modeling engine 111 processes the group of genetic training sequences and medical condition severity values indicated by the group of training observational labels to generate a distribution of the medical condition severity values across the group of candidate genetic variants. The cross-variant risk modeling engine 111 may then process the generated distribution to determine a p-value for each genetic variant in the group of genetic variants.

At step/operation 705, the cross-variant risk modeling engine 111 identifies a selected subset of the group of candidate genetic variants based on each p-value for a genetic variant in the group of candidate genetic variants. In some embodiments, to identify the selected subset of the group of candidate genetic variants, the cross-variant risk modeling engine 111 identifies a first subset of the group of candidate genetic variants whose p-values fall below a p-value threshold and determines the selected subset of the group of candidate genetic variants based on the first subset. In some embodiments, the p-value threshold may be determined based on a preconfigured value, a run-time-generated value, and/or a value determined based on a trained parameter and/or a trained hyper-parameter of the training process. An example of a p-value threshold is 0.1.

At step/operation 706, the cross-variant risk modeling engine 111 determines a per-variant risk probability value for each genetic variant in the selected subset of the group of candidate genetic variants. In some embodiments, the per-variant risk probability value for a particular genetic variant in the selected subset is determined based on the p-value associated with the particular genetic variant. In some embodiments, the per-variant risk probability value for a particular genetic variant in the selected subset is determined based on an odds ratio of the particular genetic variant with respect to the target medical condition as determined based on correlations between training genetic sequences and training observational labels. In some embodiments, the per-variant risk probability value for a particular genetic variant in the selected subset is determined based on a log of odds ratio of the particular genetic variant with respect to the target medical condition, where the odds ratio component of the log of odds ratio determined based on correlations between training genetic sequences and training observational labels.

In some embodiments, a per-variant risk probability value for a genetic variant is a data object that describes an estimated level of contribution of a corresponding genetic variant to occurrence of a corresponding target medical condition across a group of monitored individuals (e.g., a population of individuals some of whom are labeled as suffering from the corresponding target medical condition and others of whom are labeled as not suffering from the corresponding target medical condition). For example, the per-variant risk probability value for a particular SNP may describe an estimated likelihood that existence of the particular SNP in the genome of a particular individual may contribute to occurrence of a particular clinical condition (e.g., to occurrence of a particular type of cancer). In some embodiments, the per-variant risk probability value for a particular SNP is determined based on a log of odds ratio of the particular SNP across a group of individuals with respect to occurrence of a corresponding medical condition. In some embodiments, the per-variant risk probability value for a particular SNP is determined based on p-value of occurrence of the particular SNP with respect to a corresponding target medical condition.

At step/operation 707, the cross-variant risk modeling engine 111 identifies a group of testing genetic sequences associated with a second group of individuals. In some embodiments, a testing genetic sequence may be a genetic sequence of an individual that is configured to be utilized in order to generate an accuracy level of the trained polygenic machine learning model. In some embodiments, to identify the group of testing genetic sequences, the cross-variant risk modeling engine 111 may divide a group of labeled genetic sequences for a group of individuals into two subgroups: a training subgroup that includes labeled genetic sequences configured to be used to generate the trained polygenic machine learning model and a testing subgroup that includes labeled genetic sequences configured to be used to test the trained polygenic machine learning model. In some embodiments, the cross-variant risk modeling engine 111 may divide the group of labeled genetic sequences into the training subgroup and the testing subgroup in accordance with a division ratio value that describes a ratio of the labeled genetic sequences that will be used for testing the trained polygenic machine learning model. In some embodiments, the division ratio value may be determined based on a preconfigured value, a run-time-generated value, and/or a value determined based on a trained parameter and/or a trained hyper-parameter of the testing process.

At step/operation 708, the cross-variant risk modeling engine 111 identifies a group of testing observational labels including a testing observational label for each testing genetic sequence of the group of testing genetic sequences. In some embodiments, a testing observational label is a data object that describes a ground-truth label (e.g., a ground-truth medical condition) of a corresponding testing genetic sequence. In some embodiments, a testing observational label that is associated with a corresponding testing genetic sequence may describe a ground-truth medical condition of an individual associated with the corresponding testing genetic sequence. For example, a testing observational label for a corresponding testing genetic sequence may describe whether an individual associated with the corresponding testing genetic sequence suffers from a corresponding target medical condition. As another example, a testing observational label for a corresponding testing genetic sequence may describe a level of severity of a corresponding target medical condition in an individual associated with the corresponding testing genetic sequence.

At step/operation 709, the cross-variant risk modeling engine 111 determines, for each individual-variant pair of an individual in the second group of individuals and a genetic variant in the selected subset of the group of candidate genetic variants, a per-variant allele count for the genetic variant. In some embodiments, as part of testing per-variant risk probability values generated during a training process, the cross-variant risk modeling engine 111 determines data about genetic frequency of genetic variants mapped by the selected subset of the group of candidate genetic variants in the genome of the individuals whose genetic sequences are used during the testing stage (i.e., in the second group of individuals).

In some embodiments, a per-variant allele count is a data object that describes a relative frequency of alleles associated with a corresponding genetic variant within genome of a corresponding individual. For example, the per-variant allele count for a particular SNP may describe a relative frequency of alleles that correspond to base choices of the particular SNP within genome of the corresponding individual. In some embodiments, the per-variant allele count of a particular SNP is determined based on the zygosity value of the particular SNP. For example, the per-variant allele count for a particular SNP may describe that the allele associated with the particular SNP is homozygous, heterozygous, hemizygous, or nullizygous.

At step/operation 710, the cross-variant risk modeling engine 111 determines, for each individual-variant pair of an individual in the second group of individuals and a genetic variant in the selected subset of the group of candidate genetic variants, a per-variant genetic risk score for the individual-variant pair based on the per-variant risk probability value for the genetic variant associated with the individual-variant pair and the per-variant allele count for the individual-variant pair. In some embodiments, to determine the per-variant genetic risk score for a particular individual-variant pair, the cross-variant risk modeling engine 111 combines the per-variant risk probability value for the genetic variant associated with the individual-variant pair and the per-variant allele count for the individual-variant pair. In some embodiments, to determine the per-variant genetic risk score for a particular individual-variant pair, the cross-variant risk modeling engine 111 multiplies the per-variant risk probability value for the genetic variant associated with the individual-variant pair and the per-variant allele count for the individual-variant pair.

At step/operation 711, the cross-variant risk modeling engine 111 determines, for each individual in the second group of individuals, a combined per-individual genetic risk score based on each per-variant genetic risk score for an individual-variant pair that is associated with the particular individual. A combined per-individual genetic risk score for a particular individual is a data object that describes an estimated likelihood that the individual will suffer from a corresponding target medical condition, where the estimated likelihood is determined based on genomic sequence data of the individual. In some embodiments, to determine the combined per-individual genetic risk score for a particular individual, the cross-variant risk modeling engine 111 combines each per-variant genetic risk score for an individual-variant pair that is associated with the particular individual. In some embodiments, to determine the combined per-individual genetic risk score for a particular individual, the cross-variant risk modeling engine 111 sums up each per-variant genetic risk score for an individual-variant pair that is associated with the particular individual. An example of a combined per-individual genetic risk score is a PRS measure.

At step/operation 712, the cross-variant risk modeling engine 111 determines an accuracy measure for the per-variant risk probability values by comparing combined per-individual genetic risk scores for the second group of individuals and the group of testing observational labels. In some embodiments, to determine the accuracy measure for the per-variant risk probability values, the cross-variant risk modeling engine 111 determines a per-individual accuracy determination for each individual in the second group of individuals by comparing whether the combined per-individual genetic risk score for the particular individual describes the medical condition described by the testing observational label for the particular individual. For example, if the combined per-individual genetic risk score for a particular individual suggests that the individual should have cancer but that individual does not indeed have cancer based on testing observational labels for the individual, a negative per-individual accuracy determination may be generated for the noted individual. Thereafter, the cross-variant risk modeling engine 111 determines the accuracy measure for the per-variant risk probability values based on each per-individual accuracy determination for an individual in the second group of individuals. For example, the cross-variant risk modeling engine 111 determines the accuracy measure for the per-variant risk probability values based on a ratio of the per-individual accuracy measures that indicate a positive accuracy determination to all of the per-individual accuracy measures.

At step/operation 713, the cross-variant risk modeling engine 111 determines a validation determination based on the accuracy measure. In some embodiments, the cross-variant risk modeling engine 111 determines the validation determination based on whether the accuracy measure exceeds an accuracy measure threshold. In some embodiments, the accuracy measure threshold may be determined based on a preconfigured value, a run-time-generated value, and/or a value determined based on a trained parameter and/or a trained hyper-parameter of the testing process. In some embodiments, a validation determination is a data object that describes whether a corresponding trained machine learning model has successfully demonstrated a desired level of accuracy during a corresponding testing process. For example, given a trained machine learning model that includes a set of per-variant genetic risk scores for a set of genetic variants, a testing process may determine a testing prediction for each individual in a group of individuals associated with a group of testing genetic sequences by applying the set of per-variant genetic risk scores to the testing genetic sequence for the individual. In the noted example, the testing process may compare the generated set of testing predictions to corresponding testing observational labels and determine an accuracy level for the trained machine learning model. Thereafter, the testing process may determine the validation determination for the trained machine learning model based on the determined accuracy level. For example, the testing process may determine the validation determination for the trained machine learning model based on whether the determined accuracy level exceeds an accuracy level threshold.

At step/operation 714, the cross-variant risk modeling engine 111 determines whether the validation determination describes a positive value. In some embodiments, the cross-variant risk modeling engine 111 determines that the validation determination describes a positive value if the validation determination describes that a trained polygenic machine learning model characterized by the per-variant probability risk values has a desired level of accuracy when evaluated using test data. In some embodiments, the cross-variant risk modeling engine 111 determines that the validation determination describes a positive value if the validation determination describes that the accuracy measure satisfies a particular accuracy measure threshold.

In some embodiments, the cross-variant risk modeling engine 111 determines that the validation determination describes a negative value if the validation determination describes that a trained polygenic machine learning model characterized by the per-variant probability risk values does not have a desired level of accuracy when evaluated using test data. In some embodiments, the cross-variant risk modeling engine 111 determines that the validation determination describes a negative value if the validation determination describes that the accuracy measure fails to satisfy a particular accuracy measure threshold.

At step/operation 715, in response to determining that the validation determination describes a positive value, the cross-variant risk modeling engine 111 finalizes the trained polygenic machine learning model based on the selected subset of the group of candidate genetic variants and the per-variant probability risk values for the selected subset of the group of candidate genetic variants. In some embodiments, to finalize the trained polygenic machine learning model, the cross-variant risk modeling engine 111 adopts the selected subset of the group of candidate genetic variants as the one or more correlated genetic variants genetic variants identified by the trained polygenic machine learning model. In some embodiments, to finalize the trained polygenic machine learning model, the cross-variant risk modeling engine 111 adopts the per-variant risk probability values for the selected subset of the group of candidate genetic variants as the per-variant risk probability values identified by the trained polygenic machine learning (i.e., as the per-variant risk probability values for the one or more correlated genetic variants identified by the trained polygenic machine learning model).

At step/operation 715, in response to determining that the validation determination describes a negative value, the cross-variant risk modeling engine 111 generates new correlated genetic variants and corresponding per-variant risk probability values. In some embodiments, in response to determining that the validation determination describes a negative value, the cross-variant risk modeling engine 111 retrains the trained polygenic machine learning model. Retraining the trained polygenic machine learning model may include repeating steps/operations 701-713 using new training genetic sequences and/or new corresponding training observational labels. Retraining the trained polygenic machine learning model may include repeating steps/operations 701-713 using new training hyper-parameters, such as using a new p-value threshold, using a new set of candidate genetic variants, using a new imposed distribution of correlations between training genetic sequences and training observational labels, and/or the like.

Returning to FIG. 6, at step/operation 602, the cross-variant risk modeling engine 111 determines the plurality of modeled genetic variants for the genetic risk profile based on the trained polygenic machine learning model. In some embodiments, the cross-variant risk modeling engine 111 includes the one or more correlated genetic variants identified by the trained machine learning model among the plurality of modeled genetic variants. In some embodiments, in addition to or instead of the one or more correlation genetic variants, the cross-variant risk modeling engine 111 includes one or more prior genetic variants determined to be correlated with the target medical condition based on prior data about a subject matter domain of the target medical condition (e.g., prior medical research about genetic contributions to the target medical condition).

In some embodiments, to identify the plurality of modeled genetic variants, the cross-variant risk modeling engine 111 may identify a plurality of SNPs that are deemed to be correlated with the target medical condition as the plurality of modeled genetic variants for the genetic risk profile. The cross-variant risk modeling engine 111 may identify the plurality of SNPs that are deemed to be correlated with the target medical condition based on at least one of inferred probability values of a group of candidate SNPs across a population of individuals, prior data about a subject matter domain of the target medical condition (e.g., prior medical research about genetic contributions to the target medical condition), and/or the like.

In some embodiments, the plurality of genetic variants include one or more static genetic variants and one or more dynamic genetic variants. In some embodiments, a static genetic variant is a genetic variant that is determined to be correlated with a corresponding target medical condition based on preexisting subject matter domain data and is accordingly included among the set of genetic variants used to perform polygenic genetic risk modeling. Examples of preexisting subject matter domain data include data describing medical research conclusions about correlation of genetic variants with target medical conditions.

In some embodiments, a dynamic genetic variant is a genetic variant that is determined to be correlated with a corresponding target medical condition based on results of an automated statistical analysis about correlation of a group of candidate genetic variants and a corresponding target medical condition. For example, in some embodiments, dynamic genetic variants may include genetic variants whose p-values with respect to a target medical condition is below a p-value threshold. In some embodiments, the plurality of genetic variants comprise one or more dynamic genetic variants whose respective p-values with respect to the target medical condition exceed a threshold risk probability value.

At step/operation 603, the cross-variant risk modeling engine 111 determines a per-variant risk probability value for each genetic variant of the plurality of modeled genetic variants based on the trained polygenic machine learning model. In some embodiments, the cross-variant risk modeling engine 111 adopts each per-variant risk probability value identified by the trained polygenic machine learning model among the per-variant risk probability values for the plurality of modeled genetic variants. In some embodiments, the cross-variant risk modeling engine 111 adjusts each per-variant risk probability value identified by the trained polygenic machine learning model among the per-variant risk probability values for the plurality of modeled genetic variants based on prior data about a subject matter domain of the target medical condition (e.g., prior medical research about genetic contributions to the target medical condition) in order to generate the per-variant risk probability values for the plurality of modeled genetic variants. In some embodiments, the cross-variant risk modeling engine 111 determines the per-variant risk probability values for the plurality of modeled genetic variants based on prior data about a subject matter domain of the target medical condition (e.g., prior medical research about genetic contributions to the target medical condition).

In some embodiments, determining the per-variant risk probability values for the plurality of modeled genetic variants comprises: (i) for each modeled genetic variant that is both in the one or more correlated genetic variants identified by the trained polygenic machine learning model and in the plurality of modeled genetic variants, determining the per-variant risk probability value for the particular modeled genetic variant based on the per-variant risk probability value for the genetic variant as identified by the trained polygenic machine learning model; and (ii) for each modeled genetic variant that is not in the one or more correlated genetic variants identified by the trained polygenic machine learning model but is in the plurality of modeled genetic variants, determining the per-variant risk probability value for the particular modeled genetic variant based on prior data about a subject matter domain of the target medical condition.

In some embodiments, determining the per-variant risk probability values for the plurality of modeled genetic variants comprises: (i) for each modeled genetic variant that is both in the one or more correlated genetic variants identified by the trained polygenic machine learning model and in the plurality of modeled genetic variants, determining the per-variant risk probability value for the particular modeled genetic variant based on the per-variant risk probability value for the genetic variant as identified by the trained polygenic machine learning model and as adjusted based on prior data about a subject matter domain of the target medical condition; and (ii) for each modeled genetic variant that is not in the one or more correlated genetic variants identified by the trained polygenic machine learning model but is in the plurality of modeled genetic variants, determining the per-variant risk probability value for the particular modeled genetic variant based on prior data about a subject matter domain of the target medical condition.

At step/operation 604, the cross-variant risk modeling engine 111 determines a per-variant allele count for each modeled genetic variant of the plurality of modeled genetic variants with respect to the particular individual. In some embodiments, a per-variant allele count is a data object that describes a relative frequency of alleles associated with a corresponding genetic variant within genome of a corresponding individual. For example, the per-variant allele count for a particular SNP may describe a relative frequency of alleles that correspond to base choices of the particular SNP within genome of the corresponding individual. In some embodiments, the per-variant allele count of a particular SNP is determined based on the zygosity value of the particular SNP. For example, the per-variant allele count for a particular SNP may describe that the allele associated with the particular SNP is homozygous, heterozygous, hemizygous, or nullizygous.

At step/operation 605, the cross-variant risk modeling engine 111 determines, for each modeled genetic variant of the plurality of modeled genetic variants, a per-variant genetic risk score with respect to the target individual and the target medical condition based on the per-variant risk probability value for the modeled genetic variant and the per-variant allele count for modeled genetic variant with respect to the target individual. In some embodiments, to determine the per-variant genetic risk score for a particular modeled genetic variant with respect to the target individual and the target medical condition, the cross-variant risk modeling engine 111 combines the per-variant risk probability value for the modeled genetic variant and the per-variant allele count for the modeled genetic variant with respect to the target individual. In some embodiments, to determine the per-variant genetic risk score for a particular modeled genetic variant with respect to the target individual and the target medical condition, the cross-variant risk modeling engine 111 multiplies the per-variant risk probability value for the modeled genetic variant and the per-variant allele count for the modeled genetic variant with respect to the target individual.

Returning to FIG. 5, at step/operation 502, the cross-variant risk modeling engine 111 determines the genetic risk profile for the target individual with respect to the target medical condition based on each per-variant genetic risk score for a modeled genetic variant of the plurality of modeled genetic variants associated with the genetic risk profile. In some embodiments, to determine the genetic risk profile for the target individual with respect to the target medical condition, the cross-variant risk modeling engine 111 combines each per-variant genetic risk score for a modeled genetic variant of the plurality of modeled genetic variants in accordance with a value order determined by a chromosome-based grouping of the plurality of modeled genetic variants.

In some embodiments, a genetic risk profile is a data object that describes per-variant genetic risk scores associated with a group of genetic variants based on a chromosome-based grouping of the group of genetic variants. For example, the genetic risk profile may describe per-variant genetic risk scores associated with a group of genetic variants whose p-value relative to a target medical condition is below a particular threshold p-value, where the ordering of the per-variant genetic risk scores within the genetic risk profile may be determined based on chromosome-based groupings of the genetic variants associated with the genetic risk profile. For example, within a particular genetic risk profile associated with a group of genetic variants that relate to four chromosomes, the per-variant genetic risk scores associated with a first subgroup of the group of genetic variants that relate to a first chromosome of the four chromosomes may be placed in initial locations of the genetic risk profile, followed by the per-variant genetic risk scores associated with a second subgroup of the group of genetic variants that relate to a second chromosome of the four chromosomes, followed by the per-variant genetic risk scores associated with a third subgroup of the group of genetic variants that relate to a third chromosome of the four chromosomes, and followed by the per-variant genetic risk scores associated with a fourth subgroup of the group of genetic variants that relate to a fourth chromosome of the four chromosomes.

In some embodiments, a chromosome-based grouping of a group of genetic variants describes, for each genetic variant in a corresponding set of genetic variants, a chromosome designation. In some embodiments, a chromosome-based grouping can be used to generate a corresponding ordering of per-variant genetic risk scores in a genetic risk profile. For example, given a chromosome-based grouping that associates SNPs S1-S4 with chromosome C1, SNPs S4-S8 with chromosome C2, and SNPs S9-S10 with chromosome C3, the cross-variant risk modeling engine 111 may generate the following genetic risk profile: {R1, R2, R3, R4, R5, R6, R7, R8, R9, R10}, where Rn is the per-variant genetic risk score for SNP Sn. As another example, given a chromosome-based grouping that associates SNPs S1-S4 with chromosome C3, SNPs S4-S8 with chromosome C2, and SNPs S9-S10 with chromosome C1, the cross-variant risk modeling engine 111 may generate the following genetic risk profile: {R9, R10, R4, R5, R6, R7, R8, R1, R2, R3}, where Rn is the per-variant genetic risk score for SNP Sn. As yet another example, given a chromosome-based grouping that associates SNPs S1, S3, S5, S7, and S9 with chromosome C2, SNPs S2, S4, and S8 with chromosome C1, and SNPs S6 and S10 with chromosome C3, the cross-variant risk modeling engine 111 may generate the following genetic risk profile: {R1, R3, R5, R7, R9, R2, R4, R8, R6, R10}, where Rn is the per-variant genetic risk score for SNP Sn.

In some embodiments, a genetic risk profile comprises one or more per-chromosome profile segments each associated with a chromosome of the plurality of chromosomes, and each per-chromosome profile segment of the one or more per-chromosome profile segments that is associated with a respective chromosome of the plurality of chromosomes comprises each per-variant genetic risk score for a genetic variant in a subset of the plurality of genetic variants that is associated with the respective chromosome.

In some embodiments, a per-chromosome profile segment describes a segment of a genetic risk profile that includes per-variant genetic risk scores for a group of genetic variants described by the genetic risk profile, where the noted group of genetic variants all relate to a common chromosome. In some embodiments, each per-chromosome profile segment is associated with a respective chromosome and comprises each per-variant genetic risk score for a genetic variant in a subset of the genetic variants that is associated with the respective chromosome. In some embodiments, when the genetic risk profile is an array data structure, the per-chromosome profile segment is a subarray of the noted array data structure. In some embodiments, when the genetic risk profile is an array data structure and each per-chromosome profile segment is a subarray of the noted array data structure, the genetic risk profile is wholly segmented by one or more per-chromosome profile segments, such that each value in the genetic risk profile belongs to one per-chromosome profile segment of the various per-chromosome profile segments and each value in the noted array data structure belongs to one sub-array associated with a per-chromosome profile segment.

In some embodiments, step/operation 502 may be performed in accordance with the process depicted in FIG. 8. The process depicted in FIG. 8 begins at step/operation 801 when the cross-variant risk modeling engine 111 generates a raw genetic risk profile, where the raw genetic risk profile includes per-variant genetic risk scores for the plurality of modeled genetic variants in accordance with a chromosome-based grouping of the plurality of modeled genetic variants. For example, given a chromosome-based grouping that associates SNPs S1-S4 with chromosome C1, SNPs S4-S8 with chromosome C2, and SNPs S9-S10 with chromosome C3, the cross-variant risk modeling engine 111 may generate the following raw genetic risk profile: {R1, R2, R3, R4, R5, R6, R7, R8, R9, R10}, where Rn is the per-variant genetic risk score for SNP Sn. As another example, given a chromosome-based grouping that associates SNPs S1-S4 with chromosome C3, SNPs S4-S8 with chromosome C2, and SNPs S9-S10 with chromosome C1, the cross-variant risk modeling engine 111 may generate the following raw genetic risk profile: {R9, R10, R4, R5, R6, R7, R8, R1, R2, R3}, where Rn is the per-variant genetic risk score for SNP Sn. As yet another example, given a chromosome-based grouping that associates SNPs S1, S3, S5, S7, and S9 with chromosome C2, SNPs S2, S4, and S8 with chromosome C1, and SNPs S6 and S10 with chromosome C3, the cross-variant risk modeling engine 111 may generate the following raw genetic risk profile: {R1, R3, R5, R7, R9, R2, R4, R8, R6, R10}, where Rn is the per-variant genetic risk score for SNP Sn.

At step/operation 802, the cross-variant risk modeling engine 111 identifies one or more per-chromosome profile segments of the raw genetic risk profile. In some embodiments, a per-chromosome profile segment describes a segment of a genetic risk profile that includes per-variant genetic risk scores for a group of genetic variants described by the genetic risk profile, where the noted group of genetic variants all relate to a common chromosome. In some embodiments, each per-chromosome profile segment is associated with a respective chromosome and comprises each per-variant genetic risk score for a genetic variant in a subset of the genetic variants that is associated with the respective chromosome. In some embodiments, when the genetic risk profile is an array data structure, the per-chromosome profile segment is a subarray of the noted array data structure. In some embodiments, when the genetic risk profile is an array data structure and each per-chromosome profile segment is a subarray of the noted array data structure, the genetic risk profile is wholly segmented by one or more per-chromosome profile segments, such that each value in the genetic risk profile belongs to one per-chromosome profile segment of the various per-chromosome profile segments and each value in the noted array data structure belongs to one sub-array associated with a per-chromosome profile segment.

For example, given a chromosome-based grouping that associates SNPs S1-S4 with chromosome C1, SNPs S4-S8 with chromosome C2, and SNPs S9-S10 with chromosome C3, and further given the raw genetic risk profile {R1, R2, R3, R4, R5, R6, R7, R8, R9, R10} (where Rn is the per-variant genetic risk score for SNP Sn) for the per-variant genetic risk scores associated with the SNPs1-10, the cross-variant risk modeling engine 111 may generate the following per-chromosome profile segments of the raw genetic risk profile: a first per-chromosome profile segment {R1, R2, R3, R4}, a second per-chromosome profile segment {R5, R6, R7, R8}, and a third per-chromosome profile segment {R9, R10}.

As another example, given a chromosome-based grouping that associates SNPs S1-S4 with chromosome C3, SNPs S4-S8 with chromosome C2, and SNPs S9-S10 with chromosome C1, and further given the raw genetic risk profile {R9, R10, R4, R5, R6, R7, R8, R1, R2, R3} for the per-variant genetic risk scores associated with the SNPs1-10 (where Rn is the per-variant genetic risk score for SNP Sn), the cross-variant risk modeling engine 111 may generate the following per-chromosome profile segments of the raw genetic risk profile: a first per-chromosome profile segment {R9, R10}, a second per-chromosome profile segment {R4, R5, R6, R7, R8}, and a third per-chromosome profile segment {R1, R2, R3}.

As yet another example, given a chromosome-based grouping that associates SNPs S1, S3, S5, S7, and S9 with chromosome C2, SNPs S2, S4, and S8 with chromosome C1, and SNPs S6 and S10 with chromosome C3, and further given the raw genetic risk profile {R1, R3, R5, R7, R9, R2, R4, R8, R6, R10} for the per-variant genetic risk scores associated with the SNPs1-10 (where Rn is the per-variant genetic risk score for SNP Sn), the cross-variant risk modeling engine 111 may generate the following per-chromosome profile segments of the raw genetic risk profile: a first per-chromosome profile segment {R1, R3, R5, R7, R9}, a second per-chromosome profile segment {R4, R8}, and a third per-chromosome profile segment {R6, R10}.

At step/operation 803, the cross-variant risk modeling engine 111 determines, for each per-chromosome profile segment identified in step/operation 802, a per-segment smoothing indicator. A per-segment smoothing indicator for a particular per-chromosome profile segment may be a data object that describes a conclusion about whether the per-variant genetic risk scores associated with the per-chromosome profile segment should be smoothed across the per-chromosome profile segment.

In some embodiments, the cross-variant risk modeling engine 111 determines that each per-chromosome profile segment identified in step/operation 802 should be smoothed. In some embodiments, the cross-variant risk modeling engine 111 determines the per-segment smoothing indicator for a particular per-chromosome profile segment based on a count of genetic variants associated with the per-chromosome profile segment. For example, the cross-variant risk modeling engine 111 may determine that the per-variant genetic risk scores a particular per-chromosome profile segment should be smoothed across the particular per-chromosome profile segment if the count of genetic variants associated with the per-chromosome profile segment exceeds an associated variant count threshold, where the associated variant count threshold may be determined based on a pre-existing value, based on a total count of associated genetic variants across all per-chromosome profile segments identified in step/operation 802, based on a maximal count of associated genetic variants for a single per-chromosome profile segment across all per-chromosome profile segments identified in step/operation 802, based on a trained parameter value for the cross-variant risk modeling engine 111, based on a hyper-parameter value for the cross-variant risk modeling engine 111, and/or the like.

For example, given a set of per-chromosome profile segments that include a first per-chromosome profile segment {R1, R2, R3, R4}, a second per-chromosome profile segment {R5, R6, R7, R8}, and a third per-chromosome profile segment {R9, R10}, and further given an associated variant count threshold value of three, the first per-chromosome profile segment and the second per-chromosome profile segment will have positive per-segment smoothing indicators, while the third per-chromosome profile segment will have a negative per-segment smoothing indicator.

As another example, given a set of per-chromosome profile segments that include a first per-chromosome profile segment {R1, R2, R3, R4, R8}, a second per-chromosome profile segment {R5, R6, R7}, and a third per-chromosome profile segment {R9, R10}, and further given an associated variant count threshold value that equals to one-tenth of the total count of associated genetic variants across all three per-chromosome profile segments, all three per-chromosome profile segments will have a positive per-segment smoothing indicator.

As yet another example, given a set of per-chromosome profile segments that include a first per-chromosome profile segment {R1, R2, R3, R4, R8}, a second per-chromosome profile segment {R5, R6, R7}, and a third per-chromosome profile segment {R9, R10}, and further given an associated variant count threshold value that equals to half of the total count of associated genetic variants for the per-chromosome profile segments having the highest number of associated genetic variants across all three per-chromosome profile segments, the first per-chromosome profile segment and the second per-chromosome profile segment will have positive per-segment smoothing indicators, while the third per-chromosome profile segment will have a negative per-segment smoothing indicator.

At step/operation 804, the cross-variant risk modeling engine 111 performs a smoothing operation across each per-chromosome profile segment having a positive per-segment smoothing indicator in order to update the genetic risk profile. In some embodiments, the cross-variant risk modeling engine 111 generates a smoothed genetic risk profile by performing a smoothing operation across each per-chromosome profile segment having a positive per-segment smoothing indicator and subsequently updates the genetic risk profile based on the generated smoothed genetic risk profile.

A smoothing operation may be any computer-implemented process that is configured to capture significant patterns in input data, while leaving out noise. In some embodiments, to perform the smoothing operation on a particular per-chromosome profile segment, the cross-variant risk modeling engine 111 maps an approximation function to the per-variant genetic risk scores associated with the particular per-chromosome profile segment. Examples of smoothing operations include various linear smoothing operations, various additive smoothing operations, Butterworth filter operations, Chebyshev filter operations, digital filter operations, elliptic filter operations, exponential smoothing operations, Kalman filter operations, kernel smoother operations, Kolmogorov-Zurbenko filter operations, Laplacian smoothing operations, local regression operations, spline fitting operations, low-pass filter operations, moving average determination operations, Ramer-Douglas-Peucker smoothing operations, stretched-grid-based smoothing operations, and/or the like.

An operational example of generating a genetic risk profile at step/operation 502 is depicted in FIG. 9. As depicted in FIG. 9, at step/operation 901, the cross-variant risk modeling engine 111 determines p-values for a set of SNPs in relation to the target medical condition. At step/operation 902, the cross-variant risk modeling engine 111 selects a subset of the SNPs whose p-value falls below the p-value threshold of 0.1. At step/operation 903, the cross-variant risk modeling engine 111 determines natural log of odds ratio for each SNP in the selected subset. At step/operation 904, the cross-variant risk modeling engine 111 multiplies natural log of odds ratio for each SNP in the selected subset by the allele count of the SNP in order to generate per-SNP genetic risk score for the SNP. At step/operation 905, the cross-variant risk modeling engine 111 combines the per-SNP genetic risk scores for the SNPs in the selected subset in order to generate the genetic risk profile.

Returning to FIG. 5, at step/operation 503, the cross-variant risk modeling engine 111 performs one or more prediction-based actions based on the genetic risk profile. Example prediction-based actions include prediction-based actions that utilize conclusions determined based on occurrence likelihood of the target medical condition in the target individual in order to affect medical service delivery to the target individual. For example, the cross-variant risk modeling engine 111 may process the genetic risk profile of the target individual to determine that the target individual has genetic variants with high degrees of correlation with the target medical condition. In response, the cross-variant risk modeling engine 111 may automatically schedule medical operations for the target individual, automatically generate patient alerts for a client device associated with the target individual, automatically generate physician alerts for a client device associated with a physician and/or with a medical institution of the target individual, automatically update a treatment regimen of the target individual, automatically generate a prescription recommendation for the target individual, automatically generate a finalized prescription for the target individual, automatically transmit a prescription of the target individual to a pharmacy server, and/or the like.

In some embodiments, performing the one or more prediction-based actions based on the genetic risk profile for a target patient comprises generating a chromosome-grouped predictive output interface comprising a chromosome-grouped predictive output graph, where a first coordinate (e.g., a horizontal coordinate) of the chromosome-grouped predictive output graph comprises descriptions of the plurality of genetic variants in accordance with the one or more per-chromosome profile segments and a second coordinate (e.g., a vertical coordinate) of the chromosome-grouped predictive output graph comprises a range of the plurality of per-variant genetic risk scores.

In some embodiments, the chromosome-based predictive output interface is data object that describes (e.g., using Hyper-Text Markup Language (HTML) data) a user interface that is configured to display data that is determined based on a genetic risk profile for the target individual. For example, a chromosome-based predictive output interface may be configured to display a chromosome-grouped predictive output graph that depicts per-variant genetic risk scores (e.g., cross-chromosome-smoothed per-variant genetic risk scores) for a group of genetic variants with respect to the target individual and the target medical condition, where the per-variant genetic risk scores are grouped based on chromosome-based groupings of genetic variants associated with those per-variant genetic risk scores, and where the per-variant genetic risk scores are determined based on the genetic risk profile for the target individual.

In some embodiments, the chromosome-grouped predictive output graph is data object that describes per-variant genetic risk scores (e.g., cross-chromosome-smoothed per-variant genetic risk scores) for a group of genetic variants with respect to the target individual and the target medical condition, where the per-variant genetic risk scores are grouped based on chromosome-based groupings of genetic variants associated with those per-variant genetic risk scores. In some embodiments, a first coordinate (e.g., a horizontal coordinate) of the chromosome-grouped predictive output graph comprises descriptions of the genetic variants associated with the chromosome-grouped predictive output graph in accordance with chromosome-based groupings of the genetic variants, while a second coordinate (e.g., a vertical coordinate) of the chromosome-grouped predictive output graph comprises a range of per-variant genetic risk scores (e.g., cross-chromosome-smoothed per-variant genetic risk scores) for the genetic variants.

An operational example of a chromosome-based predictive output interface 1000 in FIG. 10. As depicted in FIG. 10, the chromosome-based predictive output interface 1000 displays a chromosome-based predictive output graph 1010 that describes, in each graph point of various graph points of the displayed chromosome-based predictive output graph 1010, the per-variant genetic risk score for a corresponding SNP, where the x value associated with the noted graph point indicates the corresponding SNP associated with the graph point and the y value of the noted graph point indicates the corresponding per-variant genetic risk score associated with the graph point.

As further depicted in FIG. 10, the ordering of SNPs on the x axis of the chromosome-based predictive output graph 1010 is determined based on chromosome-based groupings of the SNPs indicated by the x axis. Accordingly, the x axis of the chromosome-based predictive output graph 1010 is divided into three segments 1021-1023 each associated with a chromosome of three chromosomes. The division of the x axis of the chromosome-based predictive output graph 1010 into the three segments 1021-1023 has resulted in division of the chromosome-based predictive output graph 1010 into three per-chromosome segments: a first per-chromosome segment associated with the x-axis segment 1021, a second per-chromosome segment associated with the x-axis segment 1202, and a third per-chromosome segment associated with the x-axis segment 1203.

B. Cross-Variant Polygenic Risk Modeling Using Functional Genetic Risk Profiles

FIG. 11 is a flowchart diagram of an example process 1100 for generating a functional genetic risk profile for a target individual with respect to a target medical condition.

Via the various steps/operations of the process 1100, the cross-variant risk modeling engine 111 of the cross-variant polygenic predictive data analysis computing entity 106 can efficiently and reliably generate functional genetic risk profiles by using intermediate outputs of a PRS generation process, which eliminates the need for performing resource-intensive statistical operations in order to generate the noted functional genetic risk profiles.

The process 1100 begins at step/operation 1101 when the cross-variant risk modeling engine 111 generates a per-variant genetic risk score for each genetic variant of a plurality of modeled genetic variants that relate to the functional genetic risk profile. In some embodiments, to generate the per-variant genetic risk score for each genetic variant of a plurality of modeled genetic variants for the functional genetic risk profile, the cross-variant risk modeling engine 111 generates a trained polygenic machine learning model associated with a corresponding target medical condition, where the trained polygenic machine learning model is configured to identify: (i) one or more correlated genetic variants, and (ii) for each genetic variant of the one or more correlated genetic variants, a per-variant risk score. Thereafter, the cross-variant risk modeling engine 111 uses the per-variant risk scores identified by the trained polygenic machine learning model in order to generate each per-variant genetic risk score for a genetic variant among the one or more correlated genetic variants.

In some embodiments, step/operation 1101 may be performed in accordance with the process depicted in FIG. 12. The process depicted in FIG. 12 begins at step/operation 1201 when the cross-variant risk modeling engine 111 generates the trained polygenic machine learning model. In some embodiments, generating the trained polygenic machine learning model includes generating the trained polygenic machine learning model and testing the trained polygenic machine learning model to ensure that the trained polygenic machine learning model exhibits a desired prediction accuracy level when analyzed in accordance with test data. Example techniques for generating trained polygenic machine learning models include techniques that include performing at least some of the steps/operations depicted in FIG. 7. However, a person of ordinary skill in the relevant technology will recognize that other techniques may be used to generate trained polygenic machine learning models.

In some embodiments, generating the trained polygenic machine learning model comprises identifying one or more training genetic sequences, wherein each training genetic sequence of the one or more training genetic sequences is associated with a training observational label in relation to the target medical condition; generating, based on the one or more training genetic sequences, a plurality of per-candidate-variant risk probability values, wherein the plurality of per-candidate-variant risk probability values comprise a per-candidate-variant risk probability value for each candidate genetic variant of a plurality of candidate genetic variants; determining a selected subset of the plurality of candidate genetic variants as the plurality of genetic variants; and generating the plurality of per-variant risk probability values based on each selected per-candidate-variant risk probability value for a candidate genetic variant that is in the selected subset. In embodiments, each per-candidate-variant risk probability value for a candidate genetic variant of the plurality of candidate genetic variants is a log of odds ratio of the candidate genetic variant in relation to the target medical condition as determined in accordance with the one or more training genetic sequences.

In some embodiments, generating the trained polygenic machine learning model comprises, subsequent to training a polygenic machine learning model: identifying one or more testing genetic sequences, wherein each testing genetic sequence of the one or more testing genetic sequences is associated with a testing observational label in relation to the target medical condition; determining, based on processing the one or more training genetic sequences in accordance with each selected per-candidate-variant risk probability value, a validation determination; and in response to determining that the validation determination indicates a positive value, adopting each selected per-candidate-variant risk probability value as a corresponding per-variant risk probability value for a corresponding genetic variant in the plurality of genetic variants.

At step/operation 1202, the cross-variant risk modeling engine 111 determines the plurality of modeled genetic variants based on the trained polygenic machine learning model. In some embodiments, the cross-variant risk modeling engine 111 includes the one or more correlated genetic variants identified by the trained machine learning model among the plurality of modeled genetic variants. In some embodiments, in addition to or instead of the one or more correlation genetic variants, the cross-variant risk modeling engine 111 includes one or more prior genetic variants determined to be correlated with the target medical condition based on prior data about a subject matter domain of the target medical condition (e.g., prior medical research about genetic contributions to the target medical condition).

In some embodiments, to identify the plurality of modeled genetic variants, the cross-variant risk modeling engine 111 may identify a plurality of SNPs that are deemed to be correlated with the target medical condition as the plurality of modeled genetic variants for the functional genetic risk profile. The cross-variant risk modeling engine 111 may identify the plurality of SNPs that are deemed to be correlated with the target medical condition based on at least one of inferred probability values of a group of candidate SNPs across a population of individuals, prior data about a subject matter domain of the target medical condition (e.g., prior medical research about genetic contributions to the target medical condition), and/or the like.

In some embodiments, the plurality of genetic variants include one or more static genetic variants and one or more dynamic genetic variants. In some embodiments, a static genetic variant is a genetic variant that is determined to be correlated with a corresponding target medical condition based on preexisting subject matter domain data and is accordingly included among the set of genetic variants used to perform polygenic genetic risk modeling. Examples of preexisting subject matter domain data include data describing medical research conclusions about correlation of genetic variants with target medical conditions.

In some embodiments, a dynamic genetic variant is a genetic variant that is determined to be correlated with a corresponding target medical condition based on results of an automated statistical analysis about correlation of a group of candidate genetic variants and a corresponding target medical condition. For example, in some embodiments, dynamic genetic variants may include genetic variants whose p-values with respect to a target medical condition is below a particular p-value threshold. In some embodiments, the plurality of genetic variants comprise one or more dynamic genetic variants whose respective p-values with respect to the target medical condition exceed a threshold risk probability value.

At step/operation 1203, the cross-variant risk modeling engine 111 determines a per-variant risk probability value for each genetic variant of the plurality of modeled genetic variants based on the trained polygenic machine learning model. In some embodiments, the cross-variant risk modeling engine 111 adopts each per-variant risk probability value identified by the trained polygenic machine learning model among the per-variant risk probability values for the plurality of modeled genetic variants. In some embodiments, the cross-variant risk modeling engine 111 adjusts each per-variant risk probability value identified by the trained polygenic machine learning model among the per-variant risk probability values for the plurality of modeled genetic variants based on prior data about a subject matter domain of the target medical condition (e.g., prior medical research about genetic contributions to the target medical condition) to generate the per-variant risk probability values for the plurality of modeled genetic variants. In some embodiments, the cross-variant risk modeling engine 111 determines the per-variant risk probability values for the plurality of modeled genetic variants based on prior data about a subject matter domain of the target medical condition (e.g., prior medical research about genetic contributions to the target medical condition).

In some embodiments, determining the per-variant risk probability values for the plurality of modeled genetic variants comprises: (i) for each modeled genetic variant that is both in the one or more correlated genetic variants identified by the trained polygenic machine learning model and in the plurality of modeled genetic variants, determining the per-variant risk probability value for the particular modeled genetic variant based on the per-variant risk probability value for the genetic variant as identified by the trained polygenic machine learning model; and (ii) for each modeled genetic variant that is not in the one or more correlated genetic variants identified by the trained polygenic machine learning model but is in the plurality of modeled genetic variants, determining the per-variant risk probability value for the particular modeled genetic variant based on prior data about a subject matter domain of the target medical condition.

In some embodiments, determining the per-variant risk probability values for the plurality of modeled genetic variants comprises: (i) for each modeled genetic variant that is both in the one or more correlated genetic variants identified by the trained polygenic machine learning model and in the plurality of modeled genetic variants, determining the per-variant risk probability value for the particular modeled genetic variant based on the per-variant risk probability value for the genetic variant as identified by the trained polygenic machine learning model as adjusted based on prior data about a subject matter domain of the target medical condition; and (ii) for each modeled genetic variant that is not in the one or more correlated genetic variants identified by the trained polygenic machine learning model but is in the plurality of modeled genetic variants, determining the per-variant risk probability value for the particular modeled genetic variant based on prior data about a subject matter domain of the target medical condition.

At step/operation 1204, the cross-variant risk modeling engine 111 determines a per-variant allele count for each modeled genetic variant of the plurality of modeled genetic variants with respect to the particular individual. In some embodiments, a per-variant allele count is a data object that describes a relative frequency of alleles associated with a corresponding genetic variant within genome of a corresponding individual. For example, the per-variant allele count for a particular SNP may describe a relative frequency of alleles that correspond to base choices of the particular SNP within genome of the corresponding individual. In some embodiments, the per-variant allele count of a particular SNP is determined based on the zygosity value of the particular SNP. For example, the per-variant allele count for a particular SNP may describe that the allele associated with the particular SNP is homozygous, heterozygous, hemizygous, or nullizygous.

At step/operation 1205, the cross-variant risk modeling engine 111 determines, for each modeled genetic variant of the plurality of modeled genetic variants, a per-variant genetic risk score with respect to the target individual and the target medical condition based on the per-variant risk probability value for the modeled genetic variant and the per-variant allele count for modeled genetic variant with respect to the target individual. In some embodiments, to determine the per-variant genetic risk score for a particular modeled genetic variant with respect to the target individual and the target medical condition, the cross-variant risk modeling engine 111 combines the per-variant risk probability value for the modeled genetic variant and the per-variant allele count for the modeled genetic variant with respect to the target individual. In some embodiments, to determine the per-variant genetic risk score for a particular modeled genetic variant with respect to the target individual and the target medical condition, the cross-variant risk modeling engine 111 multiplies the per-variant risk probability value for the modeled genetic variant and the per-variant allele count for the modeled genetic variant with respect to the target individual.

Returning to FIG. 11, at step/operation 1102, the cross-variant risk modeling engine 111 determines the functional genetic risk profile for the target individual with respect to the target medical condition based on each per-variant genetic risk score for a modeled genetic variant of the plurality of modeled genetic variants associated with the functional genetic risk profile. In some embodiments, to determine the functional genetic risk profile for the target individual with respect to the target medical condition, the cross-variant risk modeling engine 111 combines each per-variant genetic risk score for a modeled genetic variant of the plurality of modeled genetic variants in accordance with a value order determined by a functional-grouping-based grouping of the plurality of modeled genetic variants associated with the functional genetic risk profile.

In some embodiments, a functional genetic risk profile is a data object that describes per-variant genetic risk scores associated with a group of genetic variants based on a functional-grouping-based grouping of the group of genetic variants. For example, the functional genetic risk profile may describe per-variant genetic risk scores associated with a group of genetic variants whose p-value relative to a target medical condition is below a particular threshold p-value, where the ordering of the per-variant genetic risk scores within the functional genetic risk profile is determined based on functional-grouping-based groupings of the genetic variants associated with the genetic risk profile. For example, within a particular functional genetic risk profile associated with a group of genetic variants that relate to four functional groupings, the per-variant genetic risk scores associated with a first subgroup of the group of genetic variants that relate to a first functional grouping of the four functional groupings may be placed in initial locations of the genetic risk profile, followed by the per-variant genetic risk scores associated with a second subgroup of the group of genetic variants that relate to a second functional grouping of the four functional groupings, followed by the per-variant genetic risk scores associated with a third subgroup of the group of genetic variants that relate to a third functional grouping of the four functional groupings, and followed by the per-variant genetic risk scores associated with a fourth subgroup of the group of genetic variants that relate to a fourth functional grouping of the four functional groupings.

In some embodiments, a functional grouping is a data object that describes, for one or more genetic variants that are associated with the particular functional grouping, a designation of a common bodily function that the genetic variants affect. For example, a functional grouping may describe the bodily function affected by a group of corresponding SNPs that are associated with the functional grouping. Examples of functional groupings include functional groupings that are configured to classify SNPs based on primary biological pathways that the noted SNPs contribute to, functional groupings that classify SNPs based on protein complexes that the noted SNPs contribute to producing, and/or the like. In some embodiments, the functional groupings maintained by a polygenic predictive data analysis system include a functional grouping of SNPs that affect energy and metabolism operations, a functional grouping of SNPs that affect cell growth operations, a functional grouping of SNPs that affect immune system operations, and a functional grouping of SNPs that affect muscular operations.

In some embodiments, a functional genetic risk profile is characterized by a functional-grouping-based grouping of the modeled genetic variants associated with the functional genetic risk profile. In some embodiments, a functional-grouping-based grouping of a group of genetic variants describes, for each genetic variant in a corresponding set of genetic variants, a functional grouping designation. In some embodiments, a functional-grouping-based grouping can be used to generate a corresponding ordering of per-variant genetic risk scores in a functional genetic risk profile. For example, given a functional-grouping-based grouping that associates SNPs S1-S4 with functional grouping F1, SNPs S4-S8 with functional grouping F2, and SNPs S9-S10 with functional grouping F3, a computer system may generate the following functional genetic risk profile: {R1, R2, R3, R4, R5, R6, R7, R8, R9, R10}, where Rn is the per-variant genetic risk score for SNP Sn. As another example, given a functional-grouping-based grouping that associates SNPs S1-S4 with functional grouping F3, SNPs S4-S8 with functional grouping F2, and SNPs S9-S10 with functional grouping F1, a computer system may generate the following functional genetic risk profile: {R9, R10, R4, R5, R6, R7, R8, R1, R2, R3}, where Rn is the per-variant genetic risk score for SNP Sn. As yet another example, given a functional-grouping-based grouping that associates SNPs S1, S3, S5, S7, and S9 with functional grouping F2, SNPs S2, S4, and S8 with functional grouping F1, and SNPs S6 and S10 with functional grouping F3, the cross-variant risk modeling engine 111 may generate the following functional genetic risk profile: {R1, R3, R5, R7, R9, R2, R4, R8, R6, R10}, where Rn is the per-variant genetic risk score for SNP Sn.

In some embodiments, a functional genetic risk profile comprises one or more per-functional-grouping profile segments each associated with a functional grouping of the plurality of functional groupings, and each per-functional-grouping profile segment of the one or more per-functional-grouping profile segments that is associated with a respective functional grouping of the plurality of functional groupings comprises each per-variant genetic risk score for a genetic variant in a subset of the plurality of genetic variants that is associated with the respective functional grouping.

In some embodiments, a per-functional-grouping profile segment describes a segment of a functional genetic risk profile that includes per-variant genetic risk scores for a group of genetic variants described by the functional genetic risk profile, where the noted group of genetic variants all relate to a common functional grouping. In some embodiments, each per-functional-grouping profile segment is associated with a respective functional grouping and comprises each per-variant genetic risk score for a genetic variant in a subset of the genetic variants that is associated with the respective functional grouping. In some embodiments, when the functional genetic risk profile is an array data structure, the per-functional-grouping profile segment is a subarray of the noted array data structure. In some embodiments, when the functional genetic risk profile is an array data structure and each per-functional-grouping profile segment is a subarray of the noted array data structure, the genetic risk profile is wholly segmented by one or more per-functional-grouping profile segments, such that each value in the genetic risk profile belongs to one per-functional-grouping profile segment of the various per-functional-grouping profile segments and each value in the noted array data structure belongs to one sub-array associated with a per-functional-grouping profile segment.

In some embodiments, step/operation 1102 may be performed in accordance with the process depicted in FIG. 13. The process depicted in FIG. 13 begins at step/operation 1301 when the cross-variant risk modeling engine 111 generates a raw functional genetic risk profile, where the raw functional genetic risk profile includes per-variant genetic risk scores for the plurality of modeled genetic variants in accordance with a functional-grouping-based grouping of the plurality of modeled genetic variants.

For example, given a functional-grouping-based grouping that associates SNPs S1-S4 with functional grouping F1, SNPs S4-S8 with functional grouping F2, and SNPs S9-S10 with functional grouping F3, the cross-variant risk modeling engine 111 may generate the following raw functional genetic risk profile: {R1, R2, R3, R4, R5, R6, R7, R8, R9, R10}, where Rn is the per-variant genetic risk score for SNP Sn. As another example, given a functional-grouping-based grouping that associates SNPs S1-S4 with functional grouping F3, SNPs S4-S8 with functional grouping F2, and SNPs S9-S10 with functional grouping F1, the cross-variant risk modeling engine 111 may generate the following raw functional genetic risk profile: {R9, R10, R4, R5, R6, R7, R8, R1, R2, R3}, where Rn is the per-variant genetic risk score for SNP Sn. As yet another example, given a functional-grouping-based grouping that associates SNPs S1, S3, S5, S7, and S9 with functional grouping F2, SNPs S2, S4, and S8 with functional grouping F1, and SNPs S6 and S10 with functional grouping F3, the cross-variant risk modeling engine 111 may generate the following raw functional genetic risk profile: {R1, R3, R5, R7, R9, R2, R4, R8, R6, R10}, where Rn is the per-variant genetic risk score for SNP Sn.

At step/operation 1302, the cross-variant risk modeling engine 111 identifies one or more per-functional-grouping profile segments of the raw functional genetic risk profile. In some embodiments, a per-functional-grouping profile segment describes a segment of a functional genetic risk profile that includes per-variant genetic risk scores for a group of genetic variants described by the functional genetic risk profile, where the noted group of genetic variants all relate to a common functional grouping. In some embodiments, each per-functional-grouping profile segment is associated with a respective functional grouping and comprises each per-variant genetic risk score for a genetic variant in a subset of the genetic variants that is associated with the respective functional grouping. In some embodiments, when the functional genetic risk profile is an array data structure, the per-functional-grouping profile segment is a subarray of the noted array data structure. In some embodiments, when the functional genetic risk profile is an array data structure and each per-functional-grouping profile segment is a subarray of the noted array data structure, the functional genetic risk profile is wholly segmented by one or more per-functional-grouping profile segments, such that each value in the functional genetic risk profile belongs to one per-functional-grouping profile segment of the various per-functional-grouping profile segments and each value in the noted array data structure belongs to one sub-array associated with a per-functional-grouping profile segment.

For example, given a functional-grouping-based grouping that associates SNPs S1-S4 with functional grouping F1, SNPs S4-S8 with functional grouping F2, and SNPs S9-S10 with functional grouping F3, and further given the raw functional genetic risk profile {R1, R2, R3, R4, R5, R6, R7, R8, R9, R10} (where Rn is the per-variant genetic risk score for SNP Sn) for the per-variant genetic risk scores associated with the SNPs1-10, the cross-variant risk modeling engine 111 may generate the following per-functional-grouping profile segments of the raw functional genetic risk profile: a first per-functional-grouping profile segment {R1, R2, R3, R4}, a second per-functional-grouping profile segment {R5, R6, R7, R8}, and a third per-functional-grouping profile segment {R9, R10}.

As another example, given a functional-grouping-based grouping that associates SNPs S1-S4 with functional grouping F3, SNPs S4-S8 with functional grouping F2, and SNPs S9-S10 with functional grouping F1, and further given the raw functional genetic risk profile {R9, R10, R4, R5, R6, R7, R8, R1, R2, R3} for the per-variant genetic risk scores associated with the SNPs1-10 (where Rn is the per-variant genetic risk score for SNP Sn), the cross-variant risk modeling engine 111 may generate the following per-functional-grouping profile segments of the raw functional genetic risk profile: a first per-functional-grouping profile segment {R9, R10}, a second per-functional-grouping profile segment {R4, R5, R6, R7, R8}, and a third per-functional-grouping profile segment {R1, R2, R3}.

As yet another example, given a functional-grouping-based grouping that associates SNPs S1, S3, S5, S7, and S9 with functional grouping F2, SNPs S2, S4, and S8 with functional grouping F1, and SNPs S6 and S10 with functional grouping F3, and further given the raw functional genetic risk profile {R1, R3, R5, R7, R9, R2, R4, R8, R6, R10} for the per-variant genetic risk scores associated with the SNPs1-10 (where Rn is the per-variant genetic risk score for SNP Sn), the cross-variant risk modeling engine 111 may generate the following per-functional-grouping profile segments of the raw functional genetic risk profile: a first per-functional-grouping profile segment {R1, R3, R5, R7, R9}, a second per-functional-grouping profile segment {R4, R8}, and a third per-functional-grouping profile segment {R6, R10}.

At step/operation 1303, the cross-variant risk modeling engine 111 determines, for each per-functional-grouping profile segment identified in step/operation 1302, a per-segment smoothing indicator. A per-segment smoothing indicator for a particular per-functional-grouping profile segment may be a data object that describes a conclusion about whether the per-variant genetic risk scores associated with the per-functional-grouping profile segment should be smoothed across the per-functional-grouping profile segment.

In some embodiments, the cross-variant risk modeling engine 111 determines that each per-functional-grouping profile segment identified in step/operation 1302 should be smoothed. In some embodiments, the cross-variant risk modeling engine 111 determines the per-segment smoothing indicator for a particular per-functional-grouping profile segment based on a count of genetic variants associated with the per-functional-grouping profile segment. For example, the cross-variant risk modeling engine 111 may determine that the per-variant genetic risk scores a particular per-functional-grouping profile segment should be smoothed across the particular per-functional-grouping profile segment if the count of genetic variants associated with the per-functional-grouping profile segment exceeds an associated variant count threshold, where the associated variant count threshold may be determined based on a pre-existing value, based on a total count of associated genetic variants across all per-functional-grouping profile segments identified in step/operation 1302, based on a maximal count of associated genetic variants for a single per-functional-grouping profile segment across all per-functional-grouping profile segments identified in step/operation 1302, based on a trained parameter value for the cross-variant risk modeling engine 111, based on a hyper-parameter value for the cross-variant risk modeling engine 111, and/or the like.

For example, given a set of per-functional-grouping profile segments that include a first per-functional-grouping profile segment {R1, R2, R3, R4}, a second per-functional-grouping profile segment {R5, R6, R7, R8}, and a third per-functional-grouping profile segment {R9, R10}, and further given an associated variant count threshold value of three, the first per-functional-grouping profile segment and the second per-functional-grouping profile segment will have positive per-segment smoothing indicators, while the third per-functional-grouping profile segment will have a negative per-segment smoothing indicator.

As another example, given a set of per-functional-grouping profile segments that include a first per-functional-grouping profile segment {R1, R2, R3, R4, R8}, a second per-functional-grouping profile segment {R5, R6, R7}, and a third per-functional-grouping profile segment {R9, R10}, and further given an associated variant count threshold value that equals to one-tenth of the total count of associated genetic variants across all three per-functional-grouping profile segments, all three per-functional-grouping profile segments will have a positive per-segment smoothing indicator.

As yet another example, given a set of per-functional-grouping profile segments that include a first per-functional-grouping profile segment {R1, R2, R3, R4, R8}, a second per-functional-grouping profile segment {R5, R6, R7}, and a third per-functional-grouping profile segment {R9, R10}, and further given an associated variant count threshold value that equals to half of the total count of associated genetic variants for the per-functional-grouping profile segments having the highest number of associated genetic variants across all three per-functional-grouping profile segments, the first per-functional-grouping profile segment and the second per-functional-grouping profile segment will have positive per-segment smoothing indicators, while the third per-functional-grouping profile segment will have a negative per-segment smoothing indicator.

At step/operation 1304, the cross-variant risk modeling engine 111 performs a smoothing operation across each per-functional-grouping profile segment having a positive per-segment smoothing indicator in order to update the functional genetic risk profile. In some embodiments, the cross-variant risk modeling engine 111 generates a smoothed functional genetic risk profile by performing a smoothing operation across each per-functional-grouping profile segment having a positive per-segment smoothing indicator and subsequently updates the functional genetic risk profile based on the generated smoothed functional genetic risk profile. An operational example of various per-segment smoothing operations for various per-functional-grouping segments of a functional genetic risk profile is depicted in FIG. 14.

An operational example of generating a functional genetic risk profile at step/operation 1102 is depicted in FIG. 14. As depicted in FIG. 14, at step/operation 1401, the cross-variant risk modeling engine 111 generates a genetic risk profile for the target individual and the target condition. At step/operation 1402, the cross-variant risk modeling engine 111 sorts x axis by functional groupings (e.g., by biological pathways) in order to generate a raw functional genetic risk profile. At step/operation 1403, the cross-variant risk modeling engine 111 performs smoothing across each per-functional-grouping segment of the raw functional genetic risk profile to determine the functional genetic risk profile.

Returning to FIG. 11, at step/operation 1103, the cross-variant risk modeling engine 111 performs one or more prediction-based actions based on the functional genetic risk profile. Example prediction-based actions include prediction-based actions that utilize conclusions determined based on occurrence likelihood of the target medical condition in the target individual in order to affect medical service delivery to the target individual. For example, the cross-variant risk modeling engine 111 may process the functional genetic risk profile of the target individual to determine that the target individual has genetic variants with high degrees of correlation with the target medical condition. In response, the cross-variant risk modeling engine 111 may automatically schedule medical operations for the target individual, automatically generate patient alerts for a client device associated with the target individual, automatically generate physician alerts for a client device associated with a physician and/or a medical institution of the target individual, automatically update a treatment regimen of the target individual, automatically generate a prescription recommendation for the target individual, automatically generate a finalized prescription for the target individual, and/or the like.

In some embodiments, performing the one or more prediction-based actions based on the functional genetic risk profile for a target patient comprises generating a functionally-grouped predictive output interface comprising a functionally-grouped predictive output graph, where a first coordinate (e.g., a horizontal coordinate) of the functionally-grouped predictive output graph comprises descriptions of the plurality of genetic variants in accordance with the one or more per-functional-grouping profile segments and a second coordinate (e.g., a vertical coordinate) of the functionally-grouped predictive output graph comprises a range of the plurality of per-variant genetic risk scores.

In some embodiments, the functional-grouping-based predictive output interface is data object that describes (e.g., using HTML data) a user interface that is configured to display data that is determined based on a functional genetic risk profile for the target individual. For example, a functional-grouping-based predictive output interface may be configured to display a functionally-grouped predictive output graph that depicts per-variant genetic risk scores (e.g., cross-functional-grouping-smoothed per-variant genetic risk scores) for a group of genetic variants with respect to the target individual and the target medical condition, where the per-variant genetic risk scores are grouped based on functional-grouping-based groupings of genetic variants associated with those per-variant genetic risk scores, and where the per-variant genetic risk scores are determined based on the functional genetic risk profile for the target individual.

In some embodiments, the functionally-grouped predictive output graph is data object that describes per-variant genetic risk scores (e.g., cross-functional-grouping-smoothed per-variant genetic risk scores) for a group of genetic variants with respect to the target individual and the target medical condition, where the per-variant genetic risk scores are grouped based on functional-grouping-based groupings of genetic variants associated with those per-variant genetic risk scores. In some embodiments, a first coordinate (e.g., a horizontal coordinate) of the functionally-grouped predictive output graph comprises descriptions of the genetic variants associated with the functionally-grouped predictive output graph in accordance with functional-grouping-based groupings of the genetic variants, while a second coordinate (e.g., a vertical coordinate) of the functionally-grouped predictive output graph comprises a range of per-variant genetic risk scores (e.g., cross-functional-grouping-smoothed per-variant genetic risk scores) for the genetic variants.

An operational example of a functional-grouping-based predictive output interface 1500 in FIG. 15. As depicted in FIG. 15, the functional-grouping-based predictive output interface 1500 displays a functional-grouping-based predictive output graph 1510 that describes, in each graph point of various graph points of the displayed functional-grouping-based predictive output graph 1510, the per-variant genetic risk score for a corresponding SNP, where the x value associated with the noted graph point indicates the corresponding SNP associated with the graph point and the y value of the noted graph point indicates the corresponding per-variant genetic risk score associated with the graph point.

As further depicted in FIG. 15, the ordering of SNPs on the x axis of the functional-grouping-based predictive output graph 1510 is determined based on functional-grouping-based groupings of the SNPs indicated by the x axis. Accordingly, the x axis of the functional-grouping-based predictive output graph 1510 is divided into four segments 1521-1524 each associated with a functional grouping of four functional groupings. The division of the x axis of the functional-grouping-based predictive output graph 1510 into the four segments 1021-1024 has resulted in division of the functional-grouping-based predictive output graph 1510 into four per-functional-grouping segments: a first per-functional-grouping segment associated with the x-axis segment 1521, a second per-functional-grouping segment associated with the x-axis segment 1502, a third per-functional-grouping segment associated with the x-axis segment 1503, and a fourth per-functional-grouping segment associated with the x-axis segment 1204.

C. Per-Condition Polygenic Clustering

FIG. 16 is a flowchart diagram of an example process 1600 for performing per-condition polygenic clustering of a plurality of individuals associated with a target medical condition. Via the various steps/operations of the process 1600, the polygenic clustering engine 112 of the cross-variant polygenic predictive data analysis computing entity 106 can utilize cross-variant polygenic risk data objects (e.g., genetic risk profiles and/or functional genetic risk profiles) to efficiently and reliably determine conclusions about genetic subtypes of a target medical condition.

The process 1600 begins at step/operation 1601 when the polygenic clustering engine 112 identities a plurality of cross-variant polygenic risk data objects each associated with an individual of the plurality of individuals that is deemed to be affected by the target medical condition. In some embodiments, a cross-variant polygenic risk data object is a data object that describes per-variant genetic risk scores of a corresponding set of correlated genetic variants in a corresponding individual and with respect to a corresponding medical condition. For example, a cross-variant polygenic risk data object may describe per-variant genetic risk scores (e.g., logs of odds ratio) of a group of SNPs whose computed p-values with respect to a particular type of cancer fall below a p-value threshold, where the per-variant genetic risk scores may be determined based on per-variant genetic risk scores of the group of SNPs across a population of individuals as well as genetic occurrence frequencies of the group of SNPs in each corresponding individual. In some embodiments, at least a portion of a cross-variant polygenic risk data object is determined based on intermediate output of a PRS generation process. Examples of cross-variant polygenic risk data objects include genetic risk profiles and functional genetic risk profiles, as further described above.

In some embodiments, each cross-variant polygenic risk data object of the plurality of cross-variant polygenic risk data objects is associated with a set of modeled genetic variants. For example, the set of modeled genetic variants associated with a genetic risk profile may include a set of SNPs associated with individual values of the genetic risk profile, where the set of SNPs may be determined based on a set of SNPs whose p-values with respect to a corresponding target medical condition associated with the genetic risk profile falls below a threshold value. As another example, the set of modeled genetic variants associated with a functional genetic risk profile may include a set of SNPs associated with individual values of the functional genetic risk profile, where the set of SNPs may be determined based on a set of SNPs whose p-values with respect to a corresponding target medical condition associated with the functional genetic risk profile falls below a threshold value.

At step/operation 1602, the polygenic clustering engine 112 generates, for each cross-variant polygenic risk data object of the plurality of cross-polygenic risk data objects, one or more per-object feature values corresponding to one or more clustering features. In some embodiments, the polygenic clustering engine 112 performs feature extraction on the plurality of cross-polygenic risk data objects to extract features that can be used to map those plurality of cross-polygenic risk data objects, as further described below with reference to step/operation 1603.

In some embodiments, a clustering feature is a data object that describes a particular feature type for cross-polygenic risk data objects, where the particular feature type characterizes at least one dimension of a polygenic clustering space. Accordingly, a clustering feature may describe a feature that can be utilized to cluster cross-polygenic risk data objects and/or cluster individuals that are associated with cross-polygenic risk data objects. Examples of clustering features are features that are determined based on modeled genetic variants for a set of cross-variant polygenic risk data objects. For example, a first clustering feature may describe the per-variant genetic risk score of a corresponding cross-variant polygenic risk data object with respect to a first modeled genetic variant associated with the corresponding cross-variant polygenic risk data object. As another example, a first clustering feature may describe the per-variant genetic risk score of a corresponding cross-variant polygenic risk data object with respect to two or more modeled genetic variants associated with the corresponding cross-variant polygenic risk data object.

In some embodiments, the clustering features are determined based on an intersectional variant set of each set of modeled genetic variants for a cross-variant polygenic risk data object of the plurality of cross-variant polygenic risk data objects. An intersectional variant set of two or more sets of genetic variants may refer to a data object that describes a set of genetic variants that are in each of the two or more sets of genetic variants. For example, an intersectional variant set of two or more genetic risk profiles may include SNPs that are modeled by each of the two or more genetic risk profiles. As another example, an intersectional variant set of two or more functional genetic risk profiles may include SNPs that are modeled by each of the two or more functional genetic risk profiles.

In some embodiments, the clustering features are determined based on a union variant set of each set of modeled genetic variants for a cross-variant polygenic risk data object of the plurality of cross-variant polygenic risk data objects. A union variant set of two or more sets of genetic variants may refer to a data object that describes a set of genetic variants that are in at least one of the two or more sets of genetic variants. For example, a union variant set of two or more genetic risk profiles may include SNPs that are modeled by at least one of the two or more genetic risk profiles. As another example, a union variant set of two or more functional genetic risk profiles may include SNPs that are modeled by at least one of the two or more functional genetic risk profiles.

In some embodiments, a per-object feature value refers to a data object that describes a latest value for a corresponding clustering feature. For example, if a clustering feature is characterized by a corresponding per-variant genetic risk score for a particular SNP in a particular individual with respect to a particular medical condition, the per-object feature value for the noted clustering feature may describe a latest value of the per-variant genetic risk score for the particular SNP. As another example, if a clustering feature is characterized by per-variant genetic risk score for two or more particular SNPs in a particular individual with respect to a particular medical condition, the per-object feature value for the noted clustering feature may describe a latest value of a measure of statistical distribution (e.g., an average, a weighted average, a median, and/or the like) of the two or more per-variant genetic risk score for the particular two or more SNPs.

At step/operation 1603, the polygenic clustering engine 112 generates a polygenic clustering space based on each set of per-object feature values for a cross-variant polygenic risk data object of the plurality of cross-variant polygenic risk data objects. In some embodiments, the polygenic clustering engine 112 maps each cross-variant polygenic risk data object to the polygenic clustering space based on per-object feature values for the cross-variant polygenic risk data object in order to generate the polygenic clustering space, which can be used to perform cross-condition polygenic clustering, as further described with reference to step/operation 1605.

In some embodiments, the polygenic clustering space is a data object that describes, for each cross-variant polygenic risk data object mapped by the polygenic clustering space, a per-object feature value for the cross-variant polygenic risk data object. In some embodiments, the polygenic clustering space is a n-dimensional space, where n is the number of clustering features associated with the polygenic clustering space. In some embodiments, the polygenic clustering space is generated by performing dimensionality reduction on a raw multi-dimensional space characterized by per-SNP dimensions, where each of the per-SNP dimensions of the polygenic clustering space describes the per-SNP genetic risk score in a corresponding cross-variant polygenic risk data object for a corresponding SNP associated with the per-SNP dimension. While various embodiments of the present invention describe polygenic clustering spaces that are used to map cross-variant polygenic risk data objects, a person of ordinary skill in the art will recognize that polygenic clustering spaces can be used to map individuals. Indeed, in some embodiments, if the same individual is associated with two or more cross-variant polygenic risk data objects (e.g., a genetic risk profile and a functional genetic risk profile), the per-object features of the two or more cross-variant polygenic risk data objects will be aggregated to generate a single per-individual feature for the corresponding individual.

An operational example of a polygenic clustering space 1700 is depicted in FIG. 17. As depicted in FIG. 17, the polygenic clustering space 1700 is associated with three clustering features: a first clustering feature 1701 that describes per-variant genetic risk scores for a first SNP, a second clustering feature 1702 that describes per-variant genetic risk scores for a second SNP, and a third clustering feature 1703 that describes per-variant genetic risk scores for a third SNP. As further depicted in FIG. 17, the polygenic clustering space 1700 includes mappings for six genetic risk profiles, namely GRP1, GRP2, GRP3, GRP4, GRP5, and GRP6.

Returning to FIG. 16, at step/operation 1604, the polygenic clustering engine 112 generates one or more inferred sub-conditions for the target medical condition based on the cross-condition clustering space. In some embodiments, to generate the inferred sub-conditions for the target medical condition, the polygenic clustering engine 112 divides the cross-variant polygenic risk data objects mapped by the polygenic clustering space into one or more clusters by using a clustering algorithm. Thereafter, the polygenic clustering engine 112 generates the inferred sub-conditions based on the one or more clusters of the polygenic clustering space.

Examples of clustering techniques that may be used to cluster a polygenic clustering space include clustering techniques based on connectivity models (e.g., hierarchical clustering), based on centroid models (e.g., using the k-means algorithm), based on distribution models (e.g., using multivariate normal distributions), based on density models, and based on subspace models (e.g., using biclustering). In some embodiments, performing clustering of a polygenic clustering space includes performing a K-means clustering of the noted polygenic clustering space. Other example of clustering algorithms that can be used to cluster a polygenic clustering space include K-medoids clustering, hierarchical clustering, K-Nearest-Neighbor clustering, and/or the like.

In some embodiments, an inferred sub-condition for a target medical condition refers to a data object that describes one or more genetic features of a proper subset of individuals affected by the target medical condition. The inferred sub-conditions for a target medical condition may be determined by mapping genetic data of individuals associated with the target medical condition onto a polygenic clustering space and clustering the mapped genetic data into non-holistic segments of the polygenic clustering space.

For example, as depicted in FIG. 17, the polygenic clustering engine 112 has generated three clusters from the genetic risk profiles mapped to the polygenic clustering space 1700: a first cluster that includes genetic risk profiles GRP1 and GRP3, a second cluster that includes genetic risk profiles GRP2 and GRP4, and a third cluster that includes genetic risk profiles GRP5 and GRP6. In some embodiments, in accordance with the three determined clusters of the polygenic clustering space 1700, the polygenic clustering engine 112 may determine three inferred sub-conditions for a corresponding target medical condition. In some embodiments, the polygenic clustering engine 112 may adjust the inferred sub-conditions based on prior subject matter domain data, such as based on data describing latest medical research on the genetic contributions to the target medical condition.

Returning to FIG. 16, at step/operation 1605, the polygenic clustering engine 112 performs one or more prediction-based actions based on the one or more inferred sub-conditions. In some embodiments, performing the one or more prediction-based actions includes determining that a first individual belongs to a first inferred sub-condition, predicting a health condition of the first individual based on health conditions of other individuals that belongs to the first inferred sub-condition, and performing one or more automated actions to address the predicted health condition of the first individual.

For example, in response to determining a health condition of a target individual based on health conditions of other individuals that belong to the same inferred sub-condition, the polygenic clustering engine 112 may automatically schedule medical operations for the target individual, automatically generate patient alerts for a client device associated with the target individual, automatically generate physician alerts for a client device associated with a physician and/or a medical institution of the target individual, automatically update a treatment regimen of the target individual, automatically generate a prescription recommendation for the target individual, automatically generate a finalized prescription for the target individual, and/or the like. In some embodiments, performing the one or more prediction-based actions comprises, for each inferred sub-condition of the one or more inferred sub-conditions, generating a per-sub-condition treatment regime based on one or more group features of a group of the plurality of individuals that are associated with the inferred sub-condition.

An operational example of performing the process 1600 is depicted in FIG. 18. According to the operational example of FIG. 18, at step/operation 1801, the polygenic clustering engine 112 generates genetic risk profiles for a group of individuals associated with a target medical condition. At step/operation 1802, the polygenic clustering engine 112 clusters the genetic risk profiles to identify genetic subtypes of the target medical condition. At step/operation 1803, the polygenic clustering engine 112 utilizes the identified genetic subtypes of the target medical condition to generate a personalized treatment regimen for each individual among the group of individuals that are deemed to be affected by the noted target medical condition.

D. Cross-Condition Polygenic Predictive Inference

FIG. 19 is a flowchart diagram of an example process 1900 for performing cross-condition polygenic predictive inference with respect to a primary medical condition and a secondary medical condition. Via the various steps/operations of the process 1900, a cross-condition inference engine 113 of the cross-variant polygenic predictive data analysis computing entity 106 can utilize cross-variant polygenic risk data objects (e.g., genetic risk profiles and/or functional genetic risk profiles) to efficiently and reliably determine conclusions about drug repurposing opportunities across various target medical conditions.

The process 1900 begins at step/operation 1901 when the cross-condition inference engine 113 identifies one or more primary cross-variant polygenic risk data objects for the primary medical condition. A primary cross-variant polygenic risk data object may be a cross-variant polygenic risk data object for an individual that is associated with the primary medical condition. Examples of primary cross-variant polygenic risk data objects include genetic risk profiles for individuals affected by the primary medical condition and functional genetic risk profiles for individuals affected by the primary medical condition.

At step/operation 1902, the cross-condition inference engine 113 identifies one or more secondary cross-variant polygenic risk data objects for the secondary medical condition. A secondary cross-variant polygenic risk data object may be a cross-variant polygenic risk data object for an individual that is associated with the secondary medical condition. Examples of secondary cross-variant polygenic risk data objects include genetic risk profiles for individuals affected by the secondary medical condition and functional genetic risk profiles for individuals affected by the secondary medical condition.

In some embodiments, the one or more primary cross-variant polygenic risk data objects comprise a primary genetic risk profile associated with a primary individual; and the one or more secondary cross-variant polygenic risk data objects comprise a secondary genetic risk profile associated with a secondary individual. In some of the noted embodiments, the primary genetic risk profile describes one or more primary per-variant genetic risk scores for a primary set of correlated genetic variants for the primary individual with respect to the target medical condition in accordance with a primary chromosome-based grouping of the primary set of correlated genetic variants; and the secondary genetic risk profile describes one or more secondary per-variant genetic risk scores for a secondary set of correlated genetic variants for the secondary individual with respect to the target medical condition in accordance with a secondary chromosome-based grouping of the secondary set of correlated genetic variants.

In some embodiments, the one or more primary cross-variant polygenic risk data objects comprise a primary functional genetic risk profiles associated with a primary individual; and the one or more secondary cross-variant polygenic risk data objects comprise a secondary functional genetic risk profile associated with a secondary individual. In some of the noted embodiments, the primary functional genetic risk profile describes one or more primary per-variant genetic risk scores for a primary set of correlated genetic variants for the primary individual with respect to the target medical condition in accordance with a primary functional-grouping-based grouping of the primary set of correlated genetic variants; and the secondary functional genetic risk profile describes one or more secondary per-variant genetic risk scores for a secondary set of correlated genetic variants for the secondary individual with respect to the target medical condition in accordance with a secondary functional-grouping-based grouping of the secondary set of correlated genetic variants.

At step/operation 1903, the cross-condition inference engine 113 generates a cross-condition polygenic similarity measure between the primary medical condition and the secondary medical condition based on comparing the one or more primary cross-variant polygenic risk data objects and the one or more secondary cross-variant polygenic risk data objects. A cross-condition polygenic similarity measure may be a data object that describes a similarity measure for two or more medical conditions based on comparing cross-variant polygenic risk data objects associated with the two or more medical conditions. For example, a cross-condition polygenic similarity measure for two medical conditions may be determined based on comparing a measure of distribution (e.g., an average) of per-variant genetic risk scores described by genetic risk profiles of individuals affected by the first medical condition and a measure of distribution of per-variant genetic risk scores described by genetic risk profiles of individuals affected by the second medical condition. As another example, a cross-condition polygenic similarity measure for two medical conditions may be determined based on comparing a measure of distribution (e.g., an average) of per-variant genetic risk scores described by functional genetic risk profiles of individuals affected by the first medical condition and a measure of distribution of per-variant genetic risk scores described by functional genetic risk profiles of individuals affected by the second medical condition.

In some embodiments, step/operation 1903 may be performed in accordance with the process depicted in FIG. 20. The process depicted in FIG. 20 begins at step/operation 2001 when the cross-condition inference engine 113 determines a pairwise similarity measure for each object pair that comprises a primary cross-variant polygenic risk data object of the one or more primary cross-variant polygenic risk data objects and a secondary cross-variant polygenic risk data object of the one or more secondary cross-variant polygenic risk data objects. A pairwise similarity measure may be a data object that describes a measure of similarity of two corresponding cross-variant polygenic risk data objects. For example, a pairwise similarity measure may describe a measure of similarity of two genetic risk profiles. As another example, a pairwise similarity measure may describe a measure of similarity of two functional genetic risk profiles. As yet another example, a pairwise similarity measure may describe a measure of similarity of a genetic risk profile and a functional genetic risk profile.

In some embodiments, with respect to a particular object pair, step/operation 2001 may be performed in accordance with the process depicted in FIG. 21. The process depicted in FIG. 21 begins at step/operation 2101 when the cross-condition inference engine 113 determines an intersectional variant count of the primary cross-variant polygenic risk data object in the object pair and the secondary cross-variant polygenic risk data object in the object pair. In general, an intersectional variant count of two or more cross-variant polygenic risk data objects refers to a data object that describes a cardinality of the set of genetic variants that is modeled by all of the two or more cross-variant polygenic data objects. For example, the intersectional variant count of the primary cross-variant polygenic risk data object in the object pair and the secondary cross-variant polygenic risk data object in the object pair describes a cardinality of genetic variants that are modeled by both the primary cross-variant polygenic risk data object and the secondary cross-variant polygenic risk data object.

At step/operation 2102, the cross-condition inference engine 113 determines a maximal variant count of the primary cross-variant polygenic risk data object in the object pair and the secondary cross-variant polygenic risk data object in the object pair. In general, a maximal variant count of two or more cross-variant polygenic risk data objects refers to a data object that describes a cardinality of the set of genetic variants that is modeled by a cross-variant polygenic data object of the two or more cross-variant polygenic data objects that has the highest number of modeled genetic variants relative to the other cross-variant polygenic data objects in the two or more cross-variant polygenic data objects. For example, if the primary cross-variant polygenic risk data object is associated with m genetic variants and the secondary cross-variant polygenic risk data object is associated with n genetic variants, and further if m>n, the maximal variant count of the primary cross-variant polygenic risk data object in the object pair and the secondary cross-variant polygenic risk data object in the object pair describes a cardinality of genetic variants that are modeled by the primary cross-variant polygenic risk data object.

At step/operation 2103, the cross-condition inference engine 113 determines the pairwise polygenic similarity measure for the particular object pair based on the intersectional variant count and the maximal variant count. In some embodiments, the cross-condition inference engine 113 computes a ratio of the intersectional variant count over the maximal variant count, and subsequently determines the pairwise similarity measure for the particular object pair based on the computed ratio.

In some embodiments, with respect to a particular object pair, step/operation 2001 may be performed in accordance with the process depicted in FIG. 22. The process depicted in FIG. 22 begins at step/operation 2201 when the cross-condition inference engine 113 determines an intersectional variant count of the primary cross-variant polygenic risk data object in the object pair and the secondary cross-variant polygenic risk data object in the object pair. In general, an intersectional variant count of two or more cross-variant polygenic risk data objects refers to a data object that describes a cardinality of the set of genetic variants that is modeled by all of the two or more cross-variant polygenic data objects. For example, the intersectional variant count of the primary cross-variant polygenic risk data object in the object pair and the secondary cross-variant polygenic risk data object in the object pair describes a cardinality of genetic variants that are modeled by both the primary cross-variant polygenic risk data object and the secondary cross-variant polygenic risk data object.

At step/operation 2202, the cross-condition inference engine 113 determines a minimal variant count of the primary cross-variant polygenic risk data object in the object pair and the secondary cross-variant polygenic risk data object in the object pair. In general, a minimal variant count of two or more cross-variant polygenic risk data objects refers to a data object that describes a cardinality of the set of genetic variants that is modeled by a cross-variant polygenic data object of the two or more cross-variant polygenic data objects that has the lowest number of modeled genetic variants relative to the other cross-variant polygenic data objects in the two or more cross-variant polygenic data objects. For example, if the primary cross-variant polygenic risk data object is associated with m genetic variants and the secondary cross-variant polygenic risk data object is associated with n genetic variants, and further if m<n, the minimal variant count of the primary cross-variant polygenic risk data object in the object pair and the secondary cross-variant polygenic risk data object in the object pair describes a cardinality of genetic variants that are modeled by the primary cross-variant polygenic risk data object.

At step/operation 2203, the cross-condition inference engine 113 determines the pairwise polygenic similarity measure for the particular object pair based on the intersectional variant count and the minimal variant count. In some embodiments, the cross-condition inference engine 113 computes a ratio of the intersectional variant count over the minimal variant count, and subsequently determines the pairwise similarity measure for the particular object pair based on the computed ratio.

In some embodiments, with respect to a particular object pair, step/operation 2001 may be performed in accordance with the process depicted in FIG. 23. The process depicted in FIG. 23 begins at step/operation 2301 when the cross-condition inference engine 113 determines an intersectional variant count of the primary cross-variant polygenic risk data object in the object pair and the secondary cross-variant polygenic risk data object in the object pair. In general, an intersectional variant count of two or more cross-variant polygenic risk data objects refers to a data object that describes a cardinality of the set of genetic variants that is modeled by all of the two or more cross-variant polygenic data objects. For example, the intersectional variant count of the primary cross-variant polygenic risk data object in the object pair and the secondary cross-variant polygenic risk data object in the object pair describes a cardinality of genetic variants that are modeled by both the primary cross-variant polygenic risk data object and the secondary cross-variant polygenic risk data object.

At step/operation 2302, the cross-condition inference engine 113 determines a union variant count of the primary cross-variant polygenic risk data object in the object pair and the secondary cross-variant polygenic risk data object in the object pair. In general, a union variant count of two or more cross-variant polygenic risk data objects refers to a data object that describes a cardinality of the set of genetic variants that is modeled by at least one of the two or more cross-variant polygenic data objects. For example, the union variant count of the primary cross-variant polygenic risk data object in the object pair and the secondary cross-variant polygenic risk data object in the object pair describes a cardinality of genetic variants that are modeled by at least one of the primary cross-variant polygenic risk data object and the secondary cross-variant polygenic risk data object.

At step/operation 2303, the cross-condition inference engine 113 determines the pairwise polygenic similarity measure for the particular object pair based on the intersectional variant count and the union variant count. In some embodiments, the cross-condition inference engine 113 computes a ratio of the intersectional variant count over the union variant count, and subsequently determines the pairwise similarity measure for the particular object pair based on the computed ratio.

In some embodiments, with respect to an object pair, step/operation 2001 may be performed in accordance with the process depicted in FIG. 24. The process depicted in FIG. 24 begins at step/operation 2401 when the cross-condition inference engine 113 identifies a plurality of genetic variants each associated with at least one of the primary cross-variant polygenic risk data object in the object pair and the secondary cross-variant polygenic risk data object in the object pair. In some embodiments, the cross-condition inference engine 113 identifies each genetic variant that is modeled by at least one of the primary cross-variant polygenic risk data object in the object pair and the secondary cross-variant polygenic risk data object in the object pair as part of the plurality of genetic variants. In some embodiments, the cross-condition inference engine 113 identifies each genetic variant that is in a union variant set of the set of modeled genetic variants for the primary cross-variant polygenic risk data object in the object pair and the set of modeled genetic variants for the secondary cross-variant polygenic risk data object in the object pair as part of the plurality of genetic variants.

At step/operation 2402, the cross-condition inference engine 113 selects a comparative variant subset of the plurality of genetic variants. The comparative variant subset may refer to a data object that describes a subset of the plurality of genetic variants whose per-variant genetic risk scores across the primary cross-variant polygenic risk data object in the object pair and the secondary cross-variant polygenic risk data object in the object pair are configured to be used to determine a pairwise similarity measure for the primary cross-variant polygenic risk data object and the secondary cross-variant polygenic risk data object.

In some embodiments, selecting the comparative variant subset comprises adopting all of the plurality of genetic variants as the comparative variant subset. In some embodiments, selecting the comparative variant subset comprises adopting an intersectional variant set of the primary cross-variant polygenic risk data object in the object pair and the secondary cross-variant polygenic risk data object in the object pair as the comparative variant subset. In some embodiments, selecting the comparative variant subset comprises adopting a union variant set of the primary cross-variant polygenic risk data object in the object pair and the secondary cross-variant polygenic risk data object in the object pair as the comparative variant subset. In some embodiment, selecting the comparative variant subset comprises adopting a symmetric difference variant set of the primary cross-variant polygenic risk data object in the object pair and the secondary cross-variant polygenic risk data object in the object pair as the comparative variant subset.

At step/operation 2403, the cross-condition inference engine 113 determines a per-variant pairwise polygenic similarity measure for each genetic variant in the comparative variant subset based on comparing a primary per-variant genetic risk score for the genetic variant inferred from the primary cross-variant polygenic risk data object and a secondary per-variant genetic risk score for the genetic variant inferred from the secondary cross-variant polygenic risk data object. In some embodiments, the cross-condition inference engine 113 performs comparisons of per-variant genetic risk scores for the genetic variants in the comparative variant subset in order to determine per-variant pairwise polygenic similarity measures for the noted genetic variant in the comparative variant subset.

In some embodiments, a per-variant pairwise polygenic similarity measure is a data object that describes a similarity measure of per-variant genetic risk data scores for two cross-variant polygenic risk data objects with respect to a corresponding genetic variant associated with the per-variant pairwise polygenic similarity measure. For example, a per-variant pairwise polygenic similarity measure may describe a similarity of the per-variant genetic risk data score for a particular genetic variant as indicated by a first genetic risk profile and the per-variant genetic risk data score for the particular genetic variant as indicated by a second genetic risk profile. As another example, a per-variant pairwise polygenic similarity measure may describe a similarity of the per-variant genetic risk data score for a particular genetic variant as indicated by a first functional genetic risk profile and the per-variant genetic risk data score for the particular genetic variant as indicated by a second functional genetic risk profile. As yet another example, a per-variant pairwise polygenic similarity measure may describe a similarity of the per-variant genetic risk data score for a particular genetic variant as indicated by a genetic risk profile and the per-variant genetic risk data score for the particular genetic variant as indicated by a functional genetic risk profile.

FIG. 25 provides a per-variant pairwise polygenic similarity data object 2500 that can be used to generate per-variant pairwise polygenic similarity measures for genetic variants in a comparative variant subset 2503. The per-variant pairwise polygenic similarity data object 2500 is configured to generate per-variant pairwise polygenic similarity measures for a first cross-variant polygenic risk data object 2501 and a second cross-variant polygenic risk data object 2502. The comparative variant subset 2503 includes a union variant set associated with the first cross-variant polygenic risk data object 2501 and the second cross-variant polygenic risk data object 2502, which includes each genetic variant that is associated with at least one of the first cross-variant polygenic risk data object 2501 and the second cross-variant polygenic risk data object 2502.

As further depicted in FIG. 25, the per-variant pairwise polygenic similarity data object 2500 includes, for each object-variant pair comprising one of the two cross-variant polygenic risk data objects in the object pair 2501-2502 and one of the genetic variants in the comparative variant subset 2503, either a value $V_{nd}$ (where n is the identifier of the genetic variant in the object-variant pair and d is the identifier of the cross-variant polygenic risk data object in the object-variant pair) or NA, which indicates a missing value. In some embodiments, a cross-variant polygenic risk data object may have an NA value for a particular genetic variant if the genetic variant is not among the modeled genetic variants used to construct the cross-variant polygenic risk data object.

In some embodiments, in accordance with the per-variant pairwise polygenic similarity data object 2500 of FIG. 24, if both the first cross-variant polygenic risk data object 2501 and the second cross-variant polygenic risk data object 2502 have a per-variant genetic risk score for a particular genetic variant in the comparative variant subset 2503, the cross-condition inference engine 113 can determine a per-variant pairwise polygenic similarity measure for the genetic variant based on a measure of similarity of the per-variant genetic risk score for the first cross-variant polygenic risk data object 2501 with respect to the genetic variant and the per-variant genetic risk score for the second cross-variant polygenic risk data object 2502 with respect to the genetic variant. For example, the cross-condition inference engine 113 can determine the per-variant pairwise polygenic similarity measure for the genetic variant SNP1 based on a measure of similarity of $V_{1A}$ and $V_{1B}$. As another example, the cross-condition inference engine 113 can determine the per-variant pairwise polygenic similarity measure for the genetic variant SNP2 based on a measure of similarity of $V_{2A}$ and $V_{2B0}$. As yet another example, the cross-condition inference engine 113 can determine the per-variant pairwise polygenic similarity measure for the genetic variant SNP10 based on a measure of similarity of $V_{10A}$ and $V_{10B}$.

In some embodiments, in accordance with the per-variant pairwise polygenic similarity data object 2500 of FIG. 25, if only one of the first cross-variant polygenic risk data object 2501 and the second cross-variant polygenic risk data object 2502 have a per-variant genetic risk score for a particular genetic variant in the comparative variant subset 2503, the cross-condition inference engine 113 can determine a maximal per-variant pairwise polygenic similarity measure for the genetic variant. For example, the cross-condition inference engine 113 can determine that SNP3, SNP8, and SNP9 have a maximal per-variant pairwise polygenic similarity measure with respect to the first cross-variant polygenic risk data object 2501 and the second cross-variant polygenic risk data object 2502.

In some embodiments, in accordance with the per-variant pairwise polygenic similarity data object 2500 of FIG. 25, if only one of the first cross-variant polygenic risk data object 2501 and the second cross-variant polygenic risk data object 2502 have a per-variant genetic risk score for a particular genetic variant in the comparative variant subset 2503, the cross-condition inference engine 113 can determine a per-variant pairwise polygenic similarity measure for the genetic variant based on the only existing per-variant genetic risk score for the genetic variant. For example, the cross-condition inference engine 113 can determine the per-variant pairwise polygenic similarity measures for SNP3, SNP8, and SNP9 based solely on $V_{3A}$, $V_{8B}$, and $V_{9B}$ respectively.

Returning to FIG. 24, at step/operation 2404, the cross-condition inference engine 113 determines the pairwise polygenic similarity measure based on each per-variant pairwise polygenic similarity measure for a genetic variant in the comparative variant subset. In some embodiments, the cross-condition inference engine 113 combines each per-variant pairwise polygenic similarity measure for a genetic variant in the comparative variant subset to determine the pairwise polygenic similarity measure. In some embodiments, the cross-condition inference engine 113 computes a weighted sum of each per-variant pairwise polygenic similarity measure for a genetic variant in the comparative variant subset to determine the pairwise polygenic similarity measure. In some embodiments, the cross-condition inference engine 113 computes a measure of statistical distribution (e.g., an average) of each per-variant pairwise polygenic similarity measure for a genetic variant in the comparative variant subset to determine the pairwise polygenic similarity measure.

Returning to FIG. 2000, at step/operation 2002, the cross-condition inference engine 113 generates the cross-condition polygenic similarity measure based on each pairwise polygenic similarity measure for an object pair as determined in step/operation 2001. In some embodiments, the cross-condition inference engine 113 combines each pairwise polygenic similarity measure to generate the cross-condition polygenic similarity measure. In some embodiments, the cross-condition inference engine 113 computes a weighted sum of each pairwise polygenic similarity measure to generate the cross-condition polygenic similarity measure. In some embodiments, the cross-condition inference engine 113 computes a measure of statistical distribution (e.g., an average) of each pairwise polygenic similarity measure to generate the cross-condition polygenic similarity measure.

Returning to FIG. 19, at step/operation 1904, the cross-condition inference engine 113 performs one or more prediction-based actions based on the cross-condition polygenic similarity measure. In some embodiments, the one or more prediction-based actions include determining that cross-condition polygenic similarity measure exceeds a cross-condition polygenic similarity measure threshold and, in response, determining a predicted health condition of individuals affected by the secondary medical condition based on the data about the primary medical condition followed by performing one or more automated actions to address the predicted health condition of the individuals affected by the secondary medical condition.

For example, in response to determining a predicted health condition of a secondary individual affected by the secondary medical condition, the cross-condition inference engine 113 may automatically schedule medical operations for the secondary individual, automatically generate patient alerts for a client device associated with the secondary individual, automatically generate physician alerts for a client device associated with a physician and/or medical institution of the secondary individual, automatically update a treatment regimen of the secondary individual, automatically generate a prescription recommendation for the secondary individual, automatically generate a finalized prescription for the secondary individual, and/or the like.

In some embodiments, performing the one or more prediction-based actions comprises determining whether the cross-condition polygenic similarity measure exceeds a cross-condition polygenic similarity threshold, and, in response to determining that the cross-condition polygenic similarity measure exceeds the cross-condition polygenic similarity threshold, generating an inferred drug prescription profile of the secondary medical condition based on an existing drug prescription profile of the primary medical condition.

FIGS. 26A, 26B, and 26C provide an operational example of performing the process 1900. As depicted in FIGS. 26A, 26B, and 26C, at step/operation 2601, the cross-condition inference engine 113 obtains cross-variant polygenic risk data objects for three medical conditions. At step/operation 2602, the cross-condition inference engine 113 detects an above-threshold cross-condition polygenic similarity between medical condition A and medical condition C by comparing the cross-variant polygenic risk data objects for three medical conditions. At step/operation 2603, in response to detecting the above-threshold cross-condition polygenic similarity between medical condition A and medical condition C, the cross-condition inference engine 113 repurposes the therapeutics (e.g., drugs) deemed suitable for treating medical condition A as therapeutics that are suitable for treating medical condition C and/or vice versa. At step/operation 2604, in response to detecting the above-threshold cross-condition polygenic similarity between medical condition A and medical condition C, the cross-condition inference engine 113 shortlists compounds used in drugs for medical condition A as leads for future research with respect to the medical condition C and/or vice versa.

E. Cross-Condition Polygenic Diagnosis

FIG. 27 is a flowchart diagram of an example process 2700 for performing cross-condition polygenic diagnosis of an undiagnosed individual. Via the various steps/operations of the process 2700, a cross-condition diagnosis engine 114 of the cross-variant polygenic predictive data analysis computing entity 106 can utilize cross-variant polygenic risk data objects (e.g., genetic risk profiles and/or functional genetic risk profiles) to efficiently and reliably perform automated diagnostic analyses for the individuals that are affected by undiagnosed medical conditions based on genetic features of those individuals relative to genetic features of repositories of diagnosed individuals with diagnosed conditions.

The process 2700 begins at step/operation 2701 when the cross-condition diagnosis engine 114 identifies one or more undiagnosed cross-variant polygenic risk data objects for the undiagnosed individual with respect to an undiagnosed medical condition. In some embodiments, the one or more undiagnosed cross-variant polygenic risk data objects comprise a genetic risk profile. In some of the noted embodiments, the genetic risk profile describes one or more per-variant genetic risk scores for a corresponding set of modeled genetic variants with respect to the undiagnosed individual and the undiagnosed medical condition in accordance with a chromosome-based grouping of the corresponding set of modeled genetic variants. In some embodiments, the one or more undiagnosed cross-variant polygenic risk data objects comprise a functional genetic risk profile. In some of the noted embodiments, the functional genetic risk profile describes one or more per-variant genetic risk scores for a corresponding set of modeled genetic variants with respect to the undiagnosed individual and the undiagnosed medical condition in accordance with a functional-grouping-based grouping of the corresponding set of modeled genetic variants.

An undiagnosed cross-variant polygenic risk data object may be a cross-variant polygenic risk data object that includes per-variant genetic risk scores for a target medical condition that has not been diagnosed with a requisite level of certainty. For example, an undiagnosed cross-variant polygenic risk data object may include a genetic risk profile related to a target medical condition that lacks any diagnostic labels. As another example, an undiagnosed cross-variant polygenic risk data object may include a genetic risk profile related to a target medical condition that has diagnostic labels, but where estimated degrees of certainty in the noted diagnostic labels falls below a certainty threshold. As yet another example, an undiagnosed cross-variant polygenic risk data object may include a functional genetic risk profile related to a target medical condition that lacks any diagnostic labels. As a further example, an undiagnosed cross-variant polygenic risk data object may include a functional genetic risk profile related to a target medical condition that has diagnostic labels, but where estimated degrees of certainty in the noted diagnostic labels falls below a certainty threshold.

At step/operation 2702, the cross-condition diagnosis engine 114 identifies one or more diagnosed cross-variant polygenic risk data objects for each diagnosed individual of one or more diagnosed individuals, where each diagnosed individual of the one or more diagnosed individuals is associated with a diagnosed medical condition of one or more diagnosed medical conditions. In some embodiments, the one or more diagnosed cross-variant polygenic risk data objects for a particular diagnosed individual comprise a genetic risk profile. In some of the noted embodiments, the genetic risk profile describes one or more per-variant genetic risk scores for a corresponding set of modeled genetic variants with respect to the particular diagnosed individual and the diagnosed medical condition that is associated with the particular diagnosed individual in accordance with a chromosome-based grouping of the corresponding set of modeled genetic variants. In some embodiments, the one or more diagnosed cross-variant polygenic risk data objects for a particular diagnosed individual comprise a genetic risk profile comprise a functional genetic risk profile. In some of the noted embodiments, the functional genetic risk profile describes one or more per-variant genetic risk scores for a corresponding set of modeled genetic variants with respect to the particular diagnosed individual and the diagnosed medical condition that is associated with the particular diagnosed individual in accordance with a functional-grouping-based grouping of the corresponding set of modeled genetic variants.

A diagnosed cross-variant polygenic risk data object may be a cross-variant polygenic risk data object that includes per-variant genetic risk scores for a target medical condition that has been diagnosed with a requisite level of certainty. For example, a diagnosed cross-variant polygenic risk data object may include a genetic risk profile related to a target medical condition that has diagnostic labels, where estimated degrees of certainty in the noted diagnostic labels satisfy a certainty threshold. As another example, a diagnosed cross-variant polygenic risk data object may include a functional genetic risk profile related to a target medical condition that has diagnostic labels, where estimated degrees of certainty in the noted diagnostic labels satisfy a certainty threshold.

At step/operation 2703, the cross-condition diagnosis engine 114 generates, for each diagnosed individual of the one or more diagnosed individuals, a cross-condition polygenic similarity measure based on comparing the one or more diagnosed cross-variant polygenic risk data objects for the diagnosed individual and the one or more undiagnosed cross-variant polygenic risk data objects.

In some embodiments, determining the cross-condition polygenic similarity measure for a diagnosed individual of one or more diagnosed individuals comprises: for each object pair of a plurality of object pairs that comprises a diagnosed cross-variant polygenic risk data object of the one or more diagnosed cross-variant polygenic risk data objects that are associated with the diagnosed individual and an undiagnosed cross-variant polygenic risk data object of the one or more undiagnosed cross-variant polygenic risk data objects, determining a pairwise polygenic similarity measure plurality of pairwise polygenic similarity measures; and generating the cross-condition polygenic similarity measure based on each pairwise polygenic similarity measure of the plurality of pairwise polygenic similarity measures. In some embodiments, determining pairwise polygenic similarity measures for object pairs and/or combining pairwise polygenic similarity measures in order to generate cross-condition polygenic similarity measures can be performed in accordance with at least some of the techniques discussed above in Section D of this document and/or in accordance with at least some of the techniques discussed above in relation to FIGS. 19-25.

In some embodiments, determining a pairwise polygenic similarity measure for a particular object pair comprises determining an intersectional variant count of the diagnosed cross-variant polygenic risk data object in the object pair and the undiagnosed cross-variant polygenic risk data object in the object pair; determining a maximal variant count of the diagnosed cross-variant polygenic risk data object in the object pair and the undiagnosed cross-variant polygenic risk data object in the object pair; and determining the pairwise polygenic similarity measure based on the intersectional variant count and the maximal variant count.

In some embodiments, determining a pairwise polygenic similarity measure for a particular object pair comprises determining an intersectional variant count of the diagnosed cross-variant polygenic risk data object in the object pair and the undiagnosed cross-variant polygenic risk data object in the object pair; determining a minimal variant count of the diagnosed cross-variant polygenic risk data object in the object pair and the undiagnosed cross-variant polygenic risk data object in the object pair; and determining the pairwise polygenic similarity measure based on the intersectional variant count and the minimal variant count.

In some embodiments, determining a pairwise polygenic similarity measure for a particular object pair comprises determining an intersectional variant count of the diagnosed cross-variant polygenic risk data object in the object pair and the undiagnosed cross-variant polygenic risk data object in the object pair; determining a union variant count of the diagnosed cross-variant polygenic risk data object in the object pair and the undiagnosed cross-variant polygenic risk data object in the object pair; and determining the pairwise polygenic similarity measure based on the intersectional variant count and the union variant count.

In some embodiments, determining a pairwise polygenic similarity measure for a particular object pair comprises identifying a plurality of genetic variants each associated with at least one of the diagnosed cross-variant polygenic risk data object in the object pair and the undiagnosed cross-variant polygenic risk data object in the object pair; selecting a comparative variant subset of the plurality of genetic variants; for each genetic variant in the comparative variant subset, determining a per-variant pairwise polygenic similarity measure based on comparing a diagnosed per-variant genetic risk score for the genetic variant inferred from the diagnosed cross-variant polygenic risk data object and an undiagnosed per-variant genetic risk score for the genetic variant inferred from the undiagnosed cross-variant polygenic risk data object; and determining the pairwise polygenic similarity measure based on each per-variant pairwise polygenic similarity measure for a genetic variant in the comparative variant subset. In some of the noted embodiments, selecting the comparative variant subset comprises adopting the plurality of genetic variants as the comparative variant subset. In some other embodiments of the noted embodiments, selecting the comparative variant subset comprises adopting an intersectional variant set of the primary cross-variant polygenic risk data object in the object pair and the secondary cross-variant polygenic risk data object in the object pair as the comparative variant subset. In yet some other embodiments of the noted embodiments, selecting the comparative variant subset comprises adopting a symmetric difference variant set of the primary cross-variant polygenic risk data object in the object pair and the secondary cross-variant polygenic risk data object in the object pair as the comparative variant subset.

At step/operation 2704, the cross-condition diagnosis engine 114 generates an inferred diagnosis for the undiagnosed individual based on each cross-condition polygenic similarity measure for a diagnosed individual of one or more diagnosed individuals. In some embodiments, to generate the inferred diagnosis for the undiagnosed individual, the cross-condition diagnosis engine 114 selects the top k diagnosed individuals having the highest cross-condition polygenic similarity measures with respect to the undiagnosed individual and determines the inferred diagnosis for the undiagnosed individual based on the corresponding diagnosed conditions for the selected diagnosed individuals. In some of the noted embodiments, k may be equal to one or more. In some of the noted embodiments, k may be determined based on system configuration data and/or may be determined based on a trainable parameter of the cross-condition diagnosis engine 114.

In some embodiments, to generate the inferred diagnosis for the undiagnosed individual, the cross-condition diagnosis engine 114 determines that a diagnosed medical condition associated with a diagnosed individual is part of the inferred diagnosis for the undiagnosed individual if the cross-condition polygenic similarity measure between the diagnosed individual and the undiagnosed individual exceeds a cross-condition polygenic similarity measure threshold. In some of the noted embodiments, the noted a cross-condition polygenic similarity measure threshold may be determined based on system configuration data and/or may be determined based on one or more trainable parameters of the cross-condition diagnosis engine 114.

In some embodiments, the inferred diagnosis may be a data object that describes one or more estimated medical conditions for an undiagnosed individual based on a cross-variant polygenic analysis of one or more cross-variant polygenic data objects associated with the undiagnosed individual and one or more cross-variant polygenic data objects associated with one or more diagnosed individuals. In some embodiments, the inferred diagnosis may describe two or more estimated medical conditions for an undiagnosed individual. In some embodiments, the inferred diagnosis may further describe a diagnosis probability value for each estimated medical condition described by the inferred diagnosis for the undiagnosed individual.

At step/operation 2705, the cross-condition diagnosis engine 114 performs one or more prediction-based actions based on the inferred diagnosis. In some embodiments, performing the one or more prediction-based actions includes determining a predicted health condition of the undiagnosed individual based on the inferred diagnosis and automatically performing actions configured to address the predicted health condition. For example, in response to determining a predicted health condition of an undiagnosed individual, the cross-condition diagnosis engine 114 may automatically schedule particular medical operations for the undiagnosed individual, automatically generate patient alerts for a client device associated with the undiagnosed individual, automatically generate physician alerts for a client device associated with a physician of the undiagnosed individual and/or a medical institution of the undiagnosed individual, automatically update a treatment regimen of the undiagnosed individual, automatically generate a prescription recommendation for the undiagnosed individual, automatically generate a finalized prescription for the undiagnosed individual, and/or the like.

In some embodiments, generating the inferred diagnosis comprises determining a related subset of the one or more diagnosed individuals whose corresponding cross-condition polygenic similarity measures exceed a cross-condition polygenic similarity measure threshold; and generating the polygenically-inferred diagnosis based on existing diagnoses of each individual in the related subset. In some of the noted embodiments, performing the one or more prediction-based actions comprises generating a treatment regimen for the undiagnosed individual based on existing treatment regimens of each diagnosed individual in the related subset.

An operational example of the process 2700 is depicted in FIGS. 28A, 28B, 28C, and 28D. As depicted in FIGS. 28A, 28B, 28C, and 28D, at step/operation 2801, the cross-condition diagnosis engine 114 retrieves undiagnosed cross-variant polygenic risk data objects for an undiagnosed individual. At step/operation 2802, the cross-condition diagnosis engine 114 retrieves diagnosed cross-variant polygenic risk data objects for a group of diagnosed individuals each associated with a diagnosed condition. At step/operation 2803, the cross-condition diagnosis engine 114 generates cross-condition similarity measures between the undiagnosed individual and each of the diagnosed individuals in order to determine, at step/operation 2804, that the undiagnosed cross-variant polygenic risk data object is most similar to the diagnosed cross-variant polygenic risk data object for a diagnosed individual associated with a medical condition B.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method, comprising:
generating, by one or more processors and based at least in part on a trained polygenic machine learning model, a set of modeled genetic variants for a plurality of individuals, wherein the trained polygenic machine learning model is trained based at least in part on a plurality of training genetic sequences, the plurality of training genetic sequences comprising genetic sequences associated with the plurality of individuals;
generating, by the one or more processors, a plurality of cross-variant polygenic risk data objects for the plurality of individuals in relation to a target medical condition, wherein a cross-variant polygenic risk data object of the plurality of cross-variant polygenic risk data objects is (i) associated with a subset of modeled genetic variants including those modeled genetic variants of the set of modeled genetic variants whose p-values with respect to the target medical condition associated with the cross-variant polygenic risk data object fall below a threshold value, (ii) generated based at least in part on one or more per-variant genetic risk scores associated with the subset of modeled genetic variants, and (iii) comprises a functional genetic risk profile for an individual of the plurality of individuals, wherein (1) the functional genetic risk profile is based at least in part on a functional grouping of the set of modeled genetic variants, and (2) the functional grouping designates a common bodily function affected by those modeled genetic variants of the functional grouping, and wherein a per-variant genetic risk score of the one or more per-variant genetic risk scores is generated based at least in part on a per-variant risk probability for the target medical condition and a per-variant allele count for the target medical condition;
for one or more cross-variant polygenic risk data objects of the plurality of cross-variant polygenic risk data objects, generating, by the one or more processors, one or more per-object feature values corresponding to one or more clustering features, wherein the one or more clustering features are determined based at least in part on the subset of modeled genetic variants of the plurality of cross-variant polygenic risk data objects;
generating, by the one or more processors, a polygenic clustering space based at least in part on the one or more per-object feature values for the one or more cross-variant polygenic risk data objects of the plurality of cross-variant polygenic risk data objects, the polygenic clustering space comprising a plurality of clustering features each describing per-variant genetic risk scores for a genetic variant;
mapping, by the one or more processors, one or more of the plurality of cross-variant polygenic risk data objects to the one or more clustering features of the polygenic clustering space based at least in part on the one or more per-object feature values associated with the one or more cross-variant polygenic risk data objects;

generating, by the one or more processors, one or more inferred sub-conditions for the target medical condition based at least in part on the mapping to the polygenic clustering space; and initiating, by the one or more processors, the performance of one or more prediction-based actions based at least in part on the one or more inferred sub-conditions.

2. The computer-implemented method of claim 1, wherein a cross-variant polygenic risk data object of the plurality of cross-variant polygenic risk data objects comprises a genetic risk profile for an individual of the plurality of individuals.

3. The computer-implemented method of claim 2, wherein the genetic risk profile comprises the one or more per-variant genetic risk scores for the corresponding subset of modeled genetic variants with respect to (i) the individual and (ii) the target medical condition in accordance with a chromosome-based grouping of a primary set of correlated genetic variants.

4. The computer-implemented method of claim 1, wherein the one or more clustering features are determined based at least in part on a union variant set of modeled genetic variants for the cross-variant polygenic risk data object.

5. The computer-implemented method of claim 1, wherein the functional genetic risk profile comprises the one or more per-variant genetic risk scores for the corresponding subset of modeled genetic variants with respect to (i) the individual and (ii) the target medical condition in accordance with the functional-grouping of a primary set of correlated genetic variants.

6. The computer-implemented method of claim 1, wherein generating the one or more inferred sub-conditions is performed based at least in part on a k-means clustering routine.

7. The computer-implemented method of claim 1, wherein initiating the performance of the one or more prediction-based actions comprises:
for an inferred sub-condition, generating a per-sub-condition treatment regime based at least in part on one or more group features of a group of the plurality of individuals that are associated with the inferred sub-condition.

8. The computer-implemented method of claim 1, wherein the one or more clustering features are determined based at least in part on an intersectional variant set of modeled genetic variants for the cross-variant polygenic risk data object.

9. An apparatus comprising one or more processors and at least one memory including program code, the at least one memory and the program code configured to, with the one or more processors, cause the apparatus to at least:
generate, based at least in part on a trained polygenic machine learning model, a set of modeled genetic variants for a plurality of individuals, wherein the trained polygenic machine learning model is trained based at least in part on a plurality of training genetic sequences, the plurality of training genetic sequences comprising genetic sequences associated with the plurality of individuals;

generate a plurality of cross-variant polygenic risk data objects for the plurality of individuals in relation to a target medical condition, wherein a cross-variant polygenic risk data object of the plurality of cross-variant polygenic risk data objects is (i) associated with a subset of modeled genetic variants including those modeled genetic variants of the set of modeled genetic variants whose p-values with respect to the target medical condition associated with the cross-variant polygenic risk data object fall below a threshold value, (ii) generated based at least in part on one or more per-variant genetic risk scores associated with the subset of modeled genetic variants, and (iii) comprises a functional genetic risk profile for an individual of the plurality of individuals, wherein (1) the functional genetic risk profile is based at least in part on a functional grouping of the set of modeled genetic variants, and (2) the functional grouping designates a common bodily function affected by those modeled genetic variants of the functional grouping, and wherein a per-variant genetic risk score of the one or more per-variant genetic risk scores is generated based at least in part on a per-variant risk probability for the target medical condition and a per-variant allele count for the target medical condition;

for one or more cross-variant polygenic risk data objects of the plurality of cross-variant polygenic risk data objects, generate one or more per-object feature values corresponding to one or more clustering features, wherein the one or more clustering features are determined based at least in part on the subset of modeled genetic variants of the plurality of cross-variant polygenic risk data objects;

generate a polygenic clustering space based at least in part on the one or more per-object feature values for the one or more cross-variant polygenic risk data objects of the plurality or cross-variant polygenic risk data objects, the polygenic clustering space comprising a plurality of clustering features each describing per-variant genetic risk scores for a genetic variant;

map one or more of the plurality of cross-variant polygenic risk data objects to the one or more clustering features of the polygenic clustering space based at least in part on the one or more per-object feature values associated with the one or more cross-variant polygenic risk data objects;

generate one or more inferred sub-conditions for the target medical condition based at least in part on the mapping to the polygenic clustering space; and initiate the performance of one or more prediction-based actions based at least in part on the one or more inferred sub-conditions.

10. The apparatus of claim 9, wherein a cross-variant polygenic risk data object of the plurality of cross-variant polygenic risk data objects comprises a genetic risk profile for an individual of the plurality of individuals.

11. The apparatus of claim 10, wherein the genetic risk profile comprises the one or more per-variant genetic risk scores for the corresponding subset of modeled genetic variants with respect to (i) the individual and (ii) the target medical condition in accordance with a chromosome-based grouping of a primary set of correlated genetic variants.

12. The apparatus of claim 9, wherein the one or more clustering features are determined based at least in part on an intersectional variant set of modeled genetic variants for a cross-variant polygenic risk data object.

13. The apparatus of claim 9, wherein initiating the performance of the one or more prediction-based actions comprises:
for an inferred sub-condition, generating a per-sub-condition treatment regime based at least in part on one or more group features of a group of the plurality of individuals that are associated with the inferred sub-condition.

14. The apparatus of claim 9, wherein the functional genetic risk profile comprises the one or more per-variant genetic risk scores for the corresponding subset of modeled genetic variants with respect to (i) the individual and (ii) the target medical condition in accordance with the functional-grouping of a primary set of correlated genetic variants.

15. The apparatus of claim 9, wherein generating the one or more inferred sub-conditions is performed based at least in part on a k-means clustering routine.

16. At least one non-transitory computer-readable storage medium having computer-readable program code portions stored therein, that when executed by one or more processors, cause the one or more processors to:
   generate, based at least in part on a trained polygenic machine learning model, a set of modeled genetic variants for a plurality of individuals, wherein the trained polygenic machine learning model is trained based at least in part on a plurality of training genetic sequences, the plurality of training genetic sequences comprising genetic sequences associated with the plurality of individuals;
   generate a plurality of cross-variant polygenic risk data objects for the plurality of individuals in relation to a target medical condition, wherein a cross-variant polygenic risk data object of the plurality of cross-variant polygenic risk data objects is (i) associated with a subset of modeled genetic variants including those modeled genetic variants of the set of modeled genetic variants whose p-values with respect to the target medical condition associated with the cross-variant polygenic risk data object fall below a threshold value, (ii) generated based at least in part on one or more per-variant genetic risk scores associated with the subset of modeled genetic variants, and (iii) comprises a functional genetic risk profile for an individual of the plurality of individuals, wherein (1) the functional genetic risk profile is based at least in part on a functional grouping of the set of modeled genetic variants, and (2) the functional grouping designates a common bodily function affected by those modeled genetic variants of the functional grouping, and wherein a per-variant genetic risk score of the one or more per-variant genetic risk scores is generated based at least in part on a per-variant risk probability for the target medical condition and a per-variant allele count for the target medical condition;
   for one or more cross-variant polygenic risk data objects of the plurality of cross-variant polygenic risk data objects, generate one or more per-object feature values corresponding to one or more clustering features, wherein the one or more clustering features are determined based at least in part on the subset of modeled genetic variants of the plurality of cross-variant polygenic risk data objects;
   generate a polygenic clustering space based at least in part on the one or more per-object feature values for the one or more cross-variant polygenic risk data objects of the plurality or cross-variant polygenic risk data objects, the polygenic clustering space comprising a plurality of clustering features each describing per-variant genetic risk scores for a genetic variant of a plurality of genetic variants;
   map one or more of the plurality of cross-variant polygenic risk data objects to the one or more clustering features of the polygenic clustering space based at least in part on the one or more per-object feature values associated with the one or more cross-variant polygenic risk data objects;
   generate one or more inferred sub-conditions for the target medical condition based at least in part on the mapping to the polygenic clustering space; and
   initiate the performance of one or more prediction-based actions based at least in part on the one or more inferred sub-conditions.

17. The at least one non-transitory computer-readable storage medium of claim 16, wherein the plurality of cross-variant polygenic risk data objects comprises a genetic risk profile for an individual of the plurality of individuals.

18. The at least one non-transitory computer-readable storage medium of claim 17, wherein the genetic risk profile comprises the one or more per-variant genetic risk scores for the corresponding subset of modeled genetic variants with respect to (i) the individual and (ii) the target medical condition in accordance with a chromosome-based grouping of a primary set of correlated genetic variants.

* * * * *